United States Patent
Guo et al.

(10) Patent No.: US 9,856,247 B2
(45) Date of Patent: Jan. 2, 2018

(54) 4-METHYL-DIHYDROPYRIMIDINES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Lei Guo, Shanghai (CN); Xianfeng Lin, Shanghai (CN); Haixia Liu, Shanghai (CN); Zongxing Qiu, Shanghai (CN); Hong Sheng, Shanghai (CN); Guozhi Tang, Shanghai (CN); Guolong Wu, Shanghai (CN); Weixing Zhang, Shanghai (CN); Wei Zhu, Shanghai (CN)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 14/839,376

(22) Filed: Aug. 28, 2015

(65) Prior Publication Data
US 2016/0052921 A1 Feb. 25, 2016
US 2017/0334898 A9 Nov. 23, 2017

Related U.S. Application Data

(63) Continuation of application No. 13/851,542, filed on Mar. 27, 2013, now abandoned.

(60) Provisional application No. PCT/CN2012/073388, filed on Mar. 31, 2012.

(30) Foreign Application Priority Data

Mar. 31, 2012 (WO) ................ PCT/CN2012/073388
Feb. 8, 2013 (WO) ................ PCT/CN2013/071575

(51) Int. Cl.
C07D 417/14 (2006.01)
C07D 417/04 (2006.01)
C07D 413/14 (2006.01)
C07D 405/14 (2006.01)
C07D 401/14 (2006.01)

(52) U.S. Cl.
CPC ......... C07D 417/14 (2013.01); C07D 401/14 (2013.01); C07D 405/14 (2013.01); C07D 413/14 (2013.01); C07D 417/04 (2013.01)

(58) Field of Classification Search
CPC .. C07D 417/14; C07D 417/04; C07D 413/14; C07D 405/14; C07D 401/14
See application file for complete search history.

(56) References Cited

U.S. PATENT DOCUMENTS

| 4,822,798 | A | 4/1989 | Stoltefuss et al. |
| 5,250,531 | A | 10/1993 | Cooper |
| 6,218,538 | B1 | 4/2001 | Downs et al. |
| 6,436,943 | B1 | 8/2002 | Stoltefuss et al. |
| 6,503,913 | B1 | 1/2003 | Goldmann et al. |
| 6,696,451 | B1 | 2/2004 | Stoltefuss et al. |
| 7,074,784 | B2 * | 7/2006 | Goldmann ........... C07D 401/04 514/227.8 |
| 7,157,461 | B2 | 1/2007 | Murugesan et al. |
| 8,106,196 | B2 | 1/2012 | Li et al. |
| 8,168,642 | B2 | 5/2012 | Li et al. |
| 8,236,797 | B2 | 8/2012 | Goldmann et al. |
| 8,329,902 | B2 | 12/2012 | Li et al. |
| 2003/0187028 | A1 | 10/2003 | Brands et al. |
| 2005/0059687 | A1 | 3/2005 | Makings et al. |
| 2007/0112015 | A1 | 5/2007 | Hurt et al. |
| 2008/0125427 | A1 | 5/2008 | Sehon et al. |
| 2010/0004268 | A1 | 1/2010 | Li et al. |
| 2010/0056569 | A1 | 3/2010 | Nan et al. |
| 2010/0087448 | A1 | 4/2010 | Li et al. |
| 2011/0021771 | A1 | 1/2011 | Mallais et al. |
| 2012/0149695 | A1 | 6/2012 | Li et al. |
| 2012/0263646 | A1 | 10/2012 | Catoen et al. |
| 2015/0005295 | A1 | 1/2015 | Vandyck et al. |
| 2015/0031687 | A1 | 1/2015 | Guo et al. |

FOREIGN PATENT DOCUMENTS

| CN | 101575314 A | 11/2009 |
| EP | 2 135 866 A1 | 12/2009 |
| EP | 2 135 866 A4 | 12/2009 |
| JP | 2002-512244 | 10/1999 |
| JP | 2002-508780 | 3/2002 |

(Continued)

OTHER PUBLICATIONS

HPV-prevention, 2016, http://www.hpv.com.au/can-hpv-be-prevented.aspx.*
RN1092453-30-4, 2009, registry record.*
RN1078164-85-8, 2008, registry record.*
Bourne et al., "Small-molecule effectors of hepatitis B virus capsid assembly give insight into virus life cycle" J Virol. 82(20):10262-70 (2008).
Brezillon et al., "Antiviral activity of Bay 41-4109 on hepatitis B virus in humanized Alb-uPA/SCID mice" PLoSONE 6(12 SUPPL 1-6):e25096 (Dec. 2011).
Office Action received in U.S. Appl. No. 14/022,519, mailed Jun. 4, 2015.
Deres et al., "Inhibition of hepatitis B virus replication by drug-induced depletion of nucleocapsids" Science 299(5608):893-6 (2003).
Feld et al., "The phenylpropenamide derivative AT-130 blocks HBV replication at the level of viral RNA packaging" Antiviral Res 76:168-177 (2007).

(Continued)

Primary Examiner — Sun Jae Yoo
(74) Attorney, Agent, or Firm — Jonathan Duffield

(57) ABSTRACT

The invention provides novel compounds having the general formula:

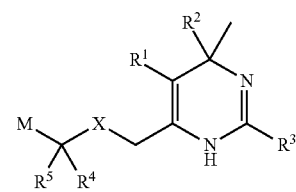

wherein $R^1$, $R^2$, $R^3$, $R^4$, $R^5$, M and X are as described herein, compositions including the compounds and methods of using the compounds.

18 Claims, 4 Drawing Sheets

(56) References Cited

FOREIGN PATENT DOCUMENTS

| | | |
|---|---|---|
| JP | 2003-526639 | 10/2003 |
| JP | 2015-508402 | 1/2015 |
| WO | 99/01438 | 1/1999 |
| WO | 99/01438 A1 | 1/1999 |
| WO | 99/54329 A1 | 10/1999 |
| WO | 00/58302 | 6/2000 |
| WO | 00/58302 | 10/2000 |
| WO | 01/45712 | 6/2001 |
| WO | 01/45712 A1 | 6/2001 |
| WO | 01/68639 | 9/2001 |
| WO | 01/68639 A1 | 9/2001 |
| WO | 01/68640 A1 | 9/2001 |
| WO | 01/68641 | 9/2001 |
| WO | 01/68641 A1 | 9/2001 |
| WO | 01/68642 | 9/2001 |
| WO | 01/68642 A1 | 9/2001 |
| WO | 01/68647 | 9/2001 |
| WO | 01/68647 A1 | 9/2001 |
| WO | 2006/033995 A2 | 3/2006 |
| WO | 2006/033995 A3 | 3/2006 |
| WO | 2007/014023 A1 | 2/2007 |
| WO | 2008/154818 | 12/2008 |
| WO | 2008/154818 A1 | 12/2008 |
| WO | 2008/154819 | 12/2008 |
| WO | 2008/154819 A1 | 12/2008 |
| WO | 2008/154820 | 12/2008 |
| WO | 2008/154820 A1 | 12/2008 |
| WO | 2010/069147 A1 | 6/2010 |
| WO | 2013/019967 A1 | 2/2013 |
| WO | 2013/144129 | 10/2013 |
| WO | 2014/029193 | 2/2014 |

OTHER PUBLICATIONS

Gentile et al., "Vertical transmission of hepatitis B virus: challenges and solutions" International Journal of Women's Health 6:605-611 ( 2014).

Halegoua-De Marzio et al., "Then and now: The progress in hepatitis B treatment over" World Journal of Gastroenterology 20(2):401-413 (Jan. 14, 2014).

Li et al., "Phase diagrams map the properties of antiviral agents directed against hepatitis B virus core assembly" Antimicrob Agents Chemother. 57(3):1505-8 ( 2013).

Stray et al., "A heteroaryldihydropyrimidine activates and can misdirect hepatitis B virus capsid assembly" Proc Natl Acad Sci U S A. 102(23):8138-43 (Jun. 2005).

Stray et al., "BAY 41-4109 has multiple effects on Hepatitis B virus capsid assembly" J Mol Recognit. 19(6):542-8 ( 2006).

Wang et al., "In vitro inhibition of HBV replication by a novel compound, GLS4, and its efficacy against adefovir-dipivoxil-resistant HBV mutations" Antivir Ther. 17(5):793-803 ( 2012).

Zhu et al., "2,4-Diaryl-4,6,7,8-tetrahydroquinazolin-5(1H)-one derivatives as anti-HBV agents targeting at capsid assembly" Bioorg Med Chem Lett 20:299-301 ( 2010).

Zlotnick et al., "A small molecule inhibits and misdirects assembly of hepatitis B virus capsids" J Virol 76(10):4848-4854 (May 2002).

* cited by examiner

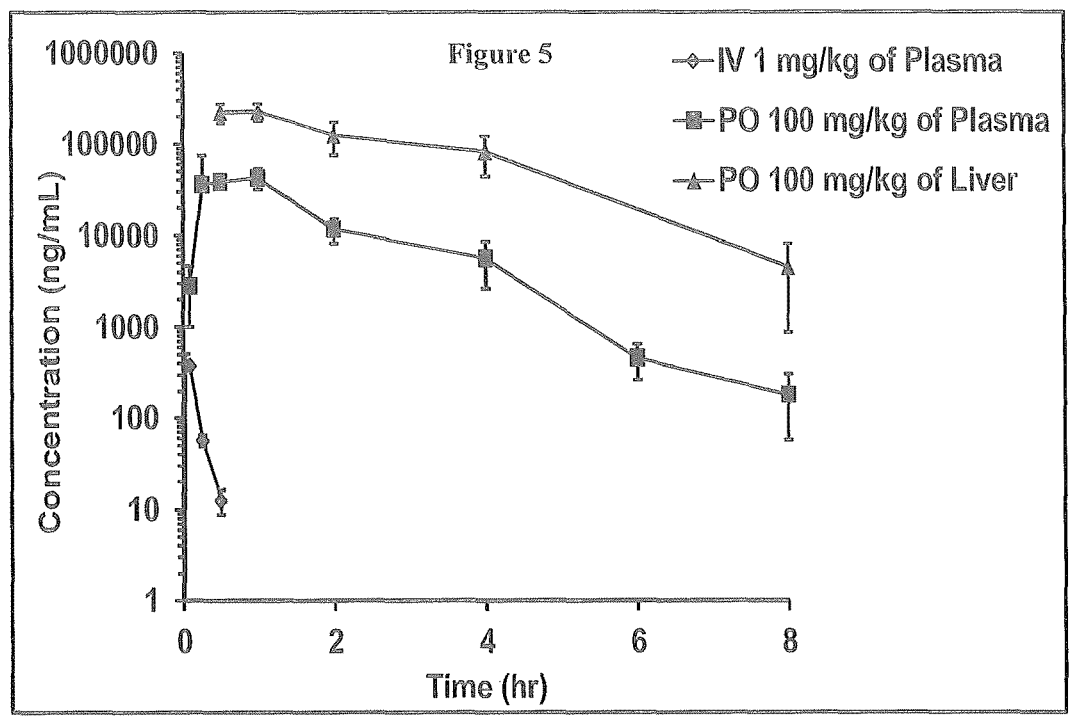
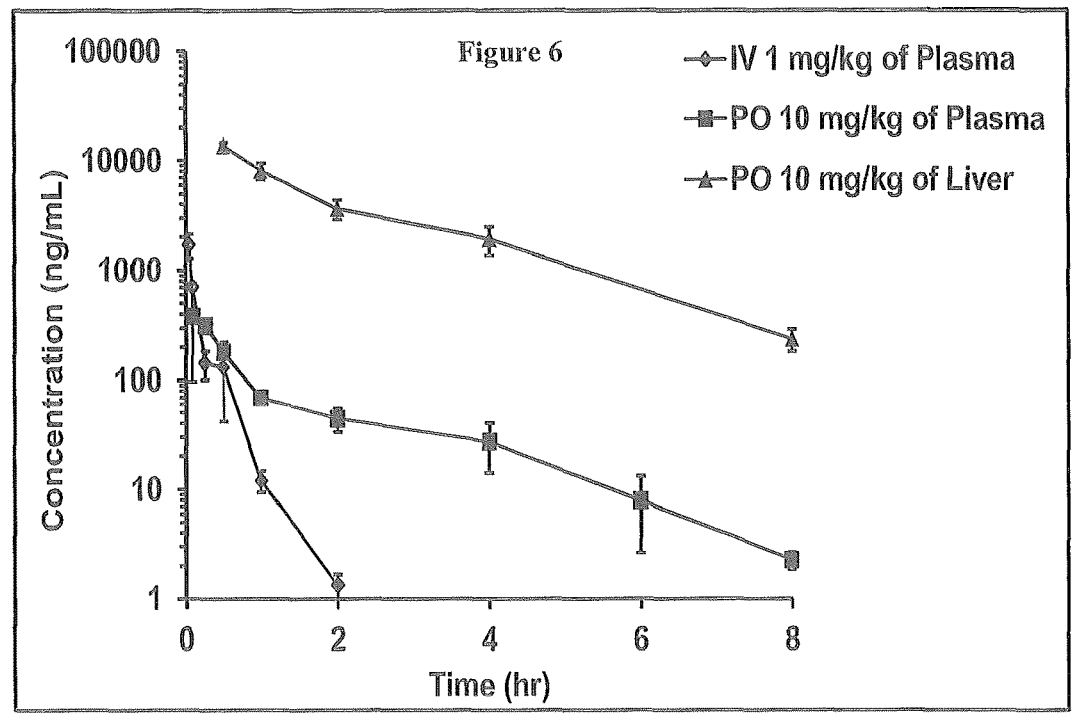

4-METHYL-DIHYDROPYRIMIDINES FOR THE TREATMENT AND PROPHYLAXIS OF HEPATITIS B VIRUS INFECTION

CROSS-REFERENCE TO PRIOR APPLICATIONS

This application is a continuation of U.S. patent application Ser. No. 13/851,542, filed on Mar. 27, 2013, which claims the benefit of priority under 35 U.S.C. §119(a) to PCT/CN2012/073388 filed Mar. 31, 2012, and PCT/CN2013/071575 filed Feb. 8, 2013, the contents of which is herein incorporated by reference in its entirety.

FIELD OF THE INVENTION

The present invention relates to organic compounds useful for therapy and/or prophylaxis in a human, and in particular to Hepatitis B virus (HBV) inhibitors by targeting on HBV capsid useful for treating HBV infection.

HBV is a species of the hepadnaviridae family of viruses. HBV is a serious public health problem worldwide, with more than 400 million people especially in Asia-pacific regions chronically infected by this small enveloped DNA virus. Although most individuals seem to resolve the infection following acute symptoms, 15-40% of HBV patients will finally develop clinical diseases during their lifespan, most notably, hepatitis, liver cirrhosis, and hepatocellular carcinoma. Every year 500,000 to 1 million people die from the end stage of liver diseases caused by HBV infection.

HBV lifecycle begins with the binding of the "Dane" particle with an unidentified receptor on the surface of hepatocyte. Following entry, viral genome is delivered into nucleus where a covalently closed circular DNA (cccDNA) is formed through DNA repair of viral relaxed circular DNA. Unlike the mechanisms of most other DNA viruses, HBV cccDNA replicates through the retrotranscription of a 1.1-genome unit-length RNA copy (pregenomic RNA). Viral pregenomic RNA interacts with other two viral components, capsid protein and polymerase, as well as some host factors, to form capsid particles where viral DNA replication occurs. Most copies of the encapsidated genome then efficiently associate with the envelope proteins for virion assembly and secretion; a minority of these genomes are shunted to the nucleus, where they are converted to cccDNA.

Currently, there are two types of anti-HBV agents on the market, nucleoside (tide) analogs targeting viral polymerase (lamivudine, adefovir, tenofovir, telbivudine and entecavir) and interferon modulating host immune functions. Mutations in the primary sequence of the polymerase that confer resistance to lamivudine and adefovir have been identified clinically and underlie a rebound of serum virus titers that 70% of treated patients experience within 3 years of the start of lamivudine therapy. Although resistance to telbivudine, adefovir, and entecavir occurs more rarely, it has been recorded. Interferon alpha is the other major therapy available for hepatitis B, but it is limited by a poor long-term response and debilitating side effects. Some viral genotypes do not show good responses to interferon therapy. Now, the standard of clinic cure of HBV infection is the loss and/or seroconversion of HBsAg. The majority (around or more than 90%) of treated patients fail to achieve this goal. This drawback is mainly due to the presence of a stable pool of viral cccDNA in nucleus that doesn't replicate itself, therefore, shows no accessibility to nucleoside (tide) analogs.

Hence, there is certainly a medical need for treatments with improved characteristics, and for a diversity of approaches in the development of therapies for HBV infection.

HBV capsid protein plays essential roles in HBV replication. HBV has an icosahedral core comprising of 240 copies of the capsid (or core) protein. The predominant biological function of capsid protein is to act as a structural protein to encapsidate pre-genomic RNA and form immature capsid particles in the cytoplasm. This step is prerequisite for viral DNA replication. The HBV capsid spontaneously self-assembles from many copies of core dimers present in the cytoplasm. It has been shown that the formation of a trimeric nucleus and the subsequent elongation reactions occur by adding one dimeric subunit at a time until it is complete. Besides this function, capsid protein regulates viral DNA synthesis through different phosphorylation status of its C-terminal phosphorylation sites. When a near full-length relaxed circular DNA is formed through reverse-transcription of viral pregenomic RNA, an immature capsid becomes a mature capsid. On one hand, capsid protein might facilitate the nuclear translocation of viral relaxed circular genome by means of the nuclear localization signals located in the Arginine-rich domain of the C-terminal region of capsid protein. In nucleus, as a component of viral cccDNA minichromosome, capsid protein could play a structural and regulatory role in the functionality of cccDNA minichromosomes. Capsid protein also interacts with viral large envelope protein in endoplasmic reticulum and triggers the release of intact viral particles from hepatocytes.

There have been a couple of capsid related anti-HBV inhibitors reported. For example, phenylpropenamide derivatives, including compounds named AT-61 and AT-130 (Feld J. et al. *Antiviral Research* 2007, 168-177), and a class of thiazolidin-4-ones from Valeant R&D (WO2006/033995), have been shown to inhibit pgRNA packaging. A recent study suggested that phenylpropenamides are, in fact, accelerators of HBV capsid assembly, and their actions result in the formation of empty capsids. These very interesting results illustrate the importance of the kinetic pathway in successful virus assembly.

Heteroaryldihydropyrimidines or HAP, including compounds named Bay 41-4109, Bay 38-7690 and Bay 39-5493, were discovered in a tissue culture-based screening (Deres K. et al. *Science* 2003, 893). These HAP analogs act as synthetic allosteric activators and are able to induce aberrant capsid formation that leads to degradation of the core protein. HAP analogs also reorganized core protein from preassembled capsids into noncapsid polymers, presumably by interaction of HAP with dimers freed during capsid 'breathing', the transitory breaking of individual intersubunit bonds. Bay 41-4109 was administered to HBV infected transgenic mouse or humanized mouse models and demonstrated in vivo efficacy with HBV DNA reduction (Deres K. et al. *Science* 2003, 893; Brezillon N. et al. *PLoS ONE* 2011, e25096.). It was also shown that bis-ANS, a small molecule that acts as a molecular 'wedge' and interferes with normal capsid-protein geometry and capsid formation (Zlotnick A. et al. *J. Virol.* 2002, 4848-4854).

SUMMARY OF THE INVENTION

Objects of the present invention are novel compounds of formula I, their manufacture, medicaments based on a compound in accordance with the invention and their production as well as the use of compounds of formula I for the treatment or prophylaxis of HBV infection.

* Drug exposure in liver is not available due to instability of Bay 41-4109 in liver homogenate.

Figure 3:
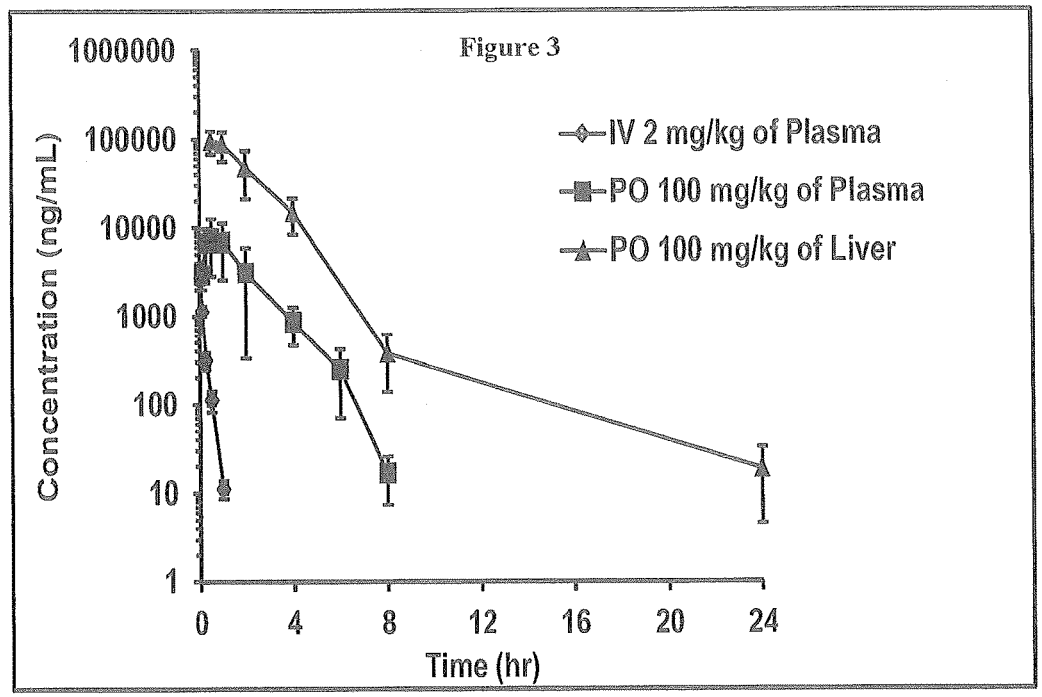
Figure 4:
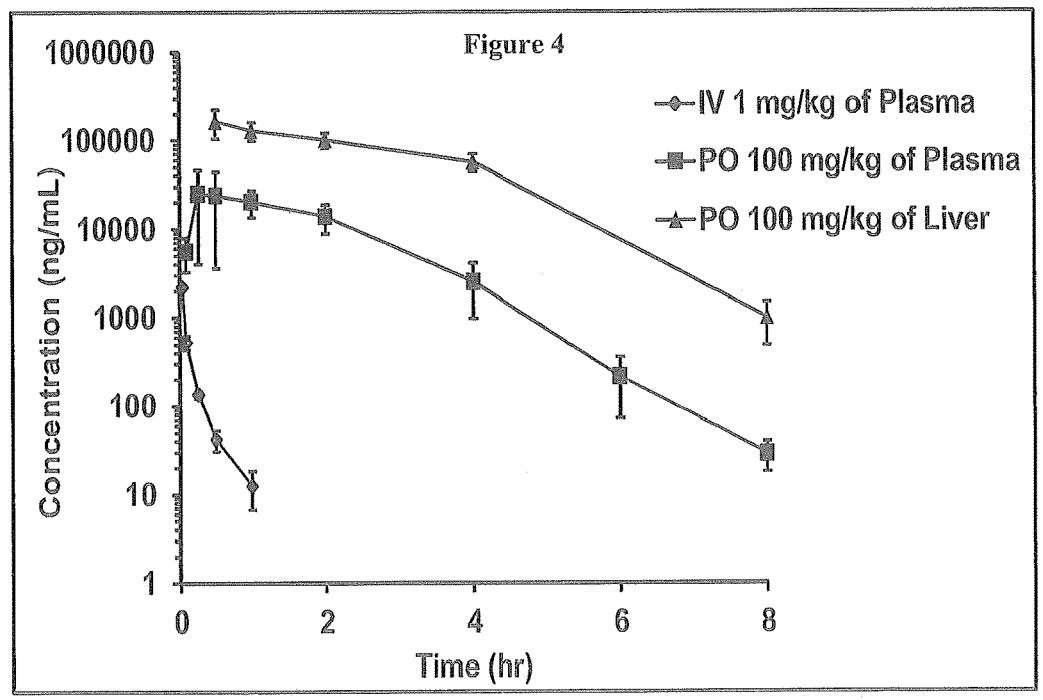

FIG. 3. Mean+SD Plasma and Tissue Concentration-Time Curve of Example 6 in Male ICR Mice Following Intravenous and Oral Administration FIG. 4. Mean+SD Plasma and Tissue Concentration-Time Curve of Example 11 in Male ICR Mice Following Intravenous and Oral Administration FIG. 5. Mean+SD Plasma and Tissue Concentration-Time Curve of Example 13 in Male ICR Mice Following Intravenous and Oral Administration FIG. 6. Mean+SD Plasma and Tissue Concentration-Time Curve of Example 19 in Male ICR Mice Following Intravenous and Oral Administration FIG. 7. X-ray structure of compound XXVII

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl, tert-butyl.

The term "cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular cycloalkyl groups are cyclopropyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, isopropoxy, n-butoxy, i-butoxy, 2-butoxy, t-butoxy and the like. Particular $C_{1-6}$alkoxy groups are methoxy and ethoxy and more particularly methoxy.

The term "$C_{2-6}$alkoxy" alone or in combination signifies a group $C_{2-6}$alkyl-O—, wherein the "$C_{2-6}$alkyl" alone or in combination signifies a saturated, linear- or branched chain alkyl group containing 2 to 6, particularly 2 to 4 carbon atoms; for example ethoxy, propoxy, isopropoxy, n-butoxy, i-butoxy, 2-butoxy, t-butoxy and the like.

The term "$C_{1-2}$alkoxy" alone or in combination refers to methoxy or ethoxy.

The term "$C_yH_{2y}$" alone or in combination signifies a saturated, linear- or branched chain alkyl group containing 1 to 6, particularly 1 to 4 carbon atoms.

The term "amino", alone or in combination, refers to primary (—$NH_2$), secondary (—NH—) or tertiary amino

The term "carbonyl" alone or in combination refers to the group —C(O)—.

The term "carboxy" alone or in combination refers to the group —COOH.

The term "cyano" alone or in combination refers to the group —CN.

The term "halogen" means fluorine, chlorine, bromine or iodine. Halogen is particularly fluorine or chlorine, more particularly fluorine.

The term "hydroxy" alone or in combination refers to the group —OH.

The term "sulfonyl" alone or in combination refers to the group —$S(O)_2$—.

The term "morpholinyl" alone or in combination refers to the group (i). When morpholine is formed between either of $R^4$ or $R^5$ and $R^7$ along with the atoms to which they are attached it represents the group (ii):

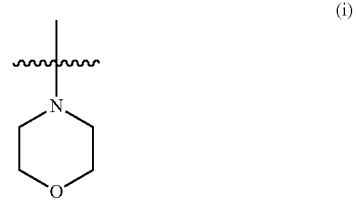

(i)

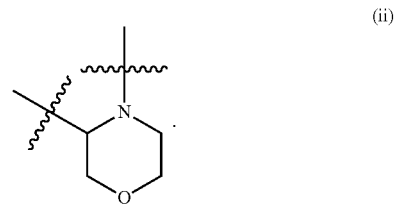

(ii)

The term "pyrrolidinyl" alone or in combination refers to the group (iii). When pyrrolidinyl is formed between either of $R^4$ or $R^5$ and $R^7$ along with the atoms to which they are attached it represents the group (iv):

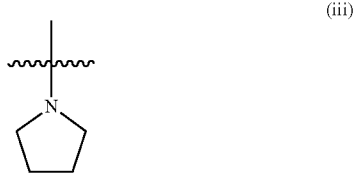

(iii)

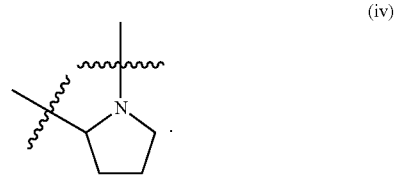

(iv)

The term "piperidinyl" alone or in combination refers to the group (v). When piperidinyl is formed between either of $R^4$ or $R^5$ and $R^7$ along with the atoms to which they are attached it represents the group (vi):

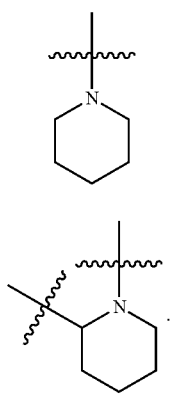

The term "tautomers isomers" refers to constitutional isomers of organic compounds that readily interconvert by a chemical reaction called tautomerization. This reaction commonly results in the formal migration of a hydrogen atom or proton, accompanied by a switch of a single bond and adjacent double bond. For example, compounds of general formular (I)

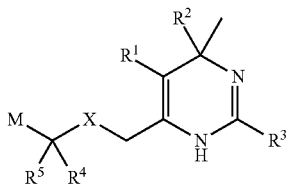

and its tautomers isomer

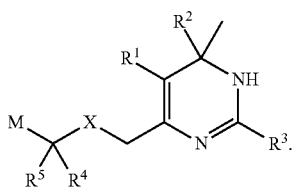

The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al., Organic Process Research & Development 2000, 4, 427-435; or in Ansel, H., et. al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of Hepatitis B Virus

The present invention provides (i) novel compounds having the general formula I:

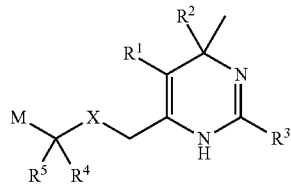

wherein
$R^1$ is $C_{1-2}$alkoxycarbonyl or cyano;
$R^2$ is phenyl, which is substituted by halogen;
$R^3$ is thiazolyl, thienyl, imidazolyl, isoxazolyl or pyridinyl; which is unsubstituted or substituted by halogen or $C_{1-6}$alkyl;
X is oxygen or $-NR^7$;
$R^4$ and $R^5$ are independently selected from hydrogen, $C_{1-6}$alkyl and trifluoro$C_{1-6}$alkyl; or
$R^4$ and $R^5$, together with the carbon atom to which they are attached, form a 3 to 7 membered cycloalkyl; or
when X is $-NR^7$, one of $R^4$ and $R^5$ is hydrogen or $C_{1-6}$alkyl, and the other of $R^4$ and $R^5$ along with $R^7$ and the atoms to which $R^4$ or $R^5$ and $R^7$ are attached form a pyrrolidinyl, morpholinyl or piperidinyl ring, which ring is unsubstituted or substituted by fluoro;
M is $C_{1-6}$alkoxycarbonyl, carboxy, di$C_{1-6}$alkylamino $C_{2-6}$alkoxycarbonyl, aminocarbonyl, $C_{1-6}$alkylaminocarbonyl, di$C_{1-6}$alkylaminocarbonyl, $C_{1-6}$alkylsulfonylaminocarbonyl, 2-thiazolylaminocarbonyl, hydroxy-$C_yH_{2y}-$,

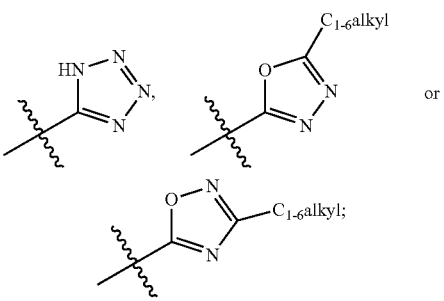

R[7] is $C_{1-6}$alkyl or trifluoro$C_{1-6}$alkyl;
y is 1-6;
or pharmaceutically acceptable salts, or tautomerism isomers thereof.

Another embodiment of present invention is (ii) a compound of formula I, wherein
R[1] is $C_{1-2}$alkoxycarbonyl or cyano;
R[2] is phenyl, which is once or twice substituted by halogen;
R[3] is 2-thiazolyl, which is unsubstituted or once substituted by $C_{1-6}$alkyl or halogen; or 2-thienyl or 2-pyridinyl, which is once substituted by halogen; or 2-imidazolyl, which is once substituted by $C_{1-6}$alkyl; or 3-isoxazolyl, which is unsubstituted or once substituted by $C_{1-6}$alkyl;
X is oxygen or —NR[7];
R[4] and R[5] are independently selected from hydrogen, $C_{1-6}$alkyl and trifluoro$C_{1-6}$alkyl; or
R[4] and R[5], together with the carbon atom to which they are attached, form a 3 to 7 membered cycloalkyl; or
when X is —NR[7], one of R[4] and R[5] is hydrogen or $C_{1-6}$alkyl, and the other of R[4] and R[5] along with R[7] and the atoms to which R[4] or R[5] and R[7] are attached form a morpholinyl; or pyrrolidinyl or piperidinyl, which is substituted by fluoro;
M is $C_{1-6}$alkoxycarbonyl, carboxy, di$C_{1-6}$alkylamino-$C_{2-6}$alkoxycarbonyl, aminocarbonyl, $C_{1-6}$alkylaminocarbonyl, di$C_{1-6}$alkylaminocarbonyl, $C_{1-6}$alkylsulfonylaminocarbonyl, 2-thiazolylaminocarbonyl, hydroxy-$C_yH_{2y}$—,

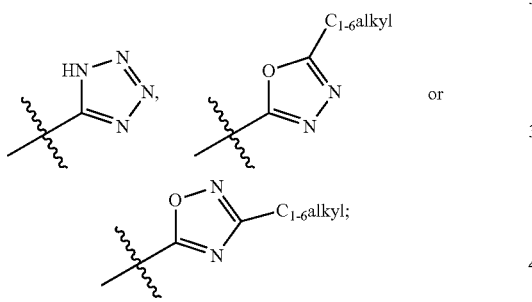

R[7] is $C_{1-6}$alkyl or trifluoro$C_{1-6}$alkyl;
y is 1-6;
or pharmaceutically acceptable salts, or tautomerism isomers thereof.

Further embodiment of present invention is (iii) a compound of formula I, wherein
R[1] is methoxycarbonyl, ethoxycarbonyl or cyano;
R[2] is phenyl substituted once or twice by fluoro;
R[3] is

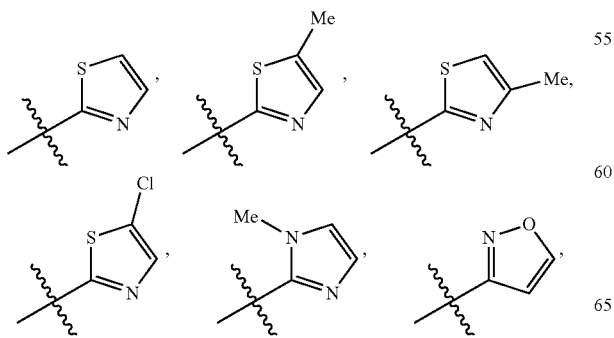

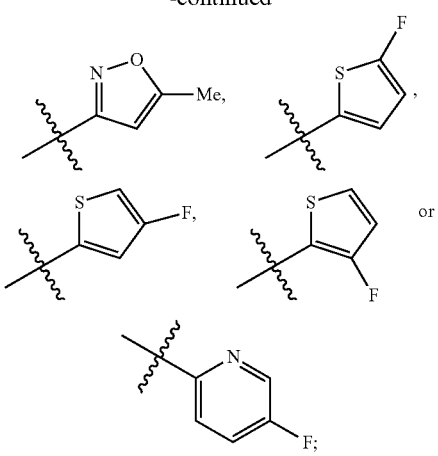

X is oxygen or —NR[7];
R[4] and R[5] are independently selected from hydrogen, methyl and trifluoromethyl; or
R[4] and R[5] together with the carbon atom to which they are attached form cyclopropyl; or when X is —NR[7], one of R[4] and R[5] is hydrogen or methyl, and the other of R[4] and R[5] along with R[7] and the atoms to which R[4] or R[5] and R[7] are attached form:

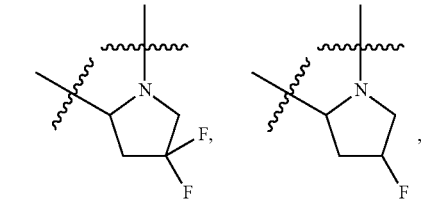

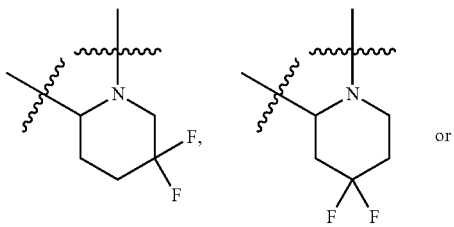

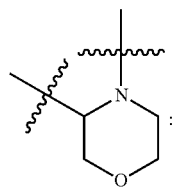

M is methoxycarbonyl, carboxy, dimethylaminoethoxycarbonyl, aminocarbonyl, dimethylaminocarbonyl, methylaminocarbonyl, methylsulfonylaminocarbonyl, 2-thiazolylaminocarbonyl, hydroxymethyl, hydroxypropyl, —C(Me)$_2$OH,

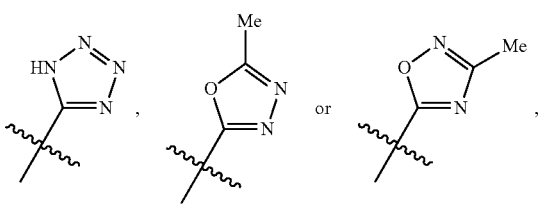 [SMILES: *c1nnn[nH]1 ; *c1nnc(C)o1 ; *c1nc(C)no1]

R⁷ is methyl or trifluoroethyl;
or pharmaceutically acceptable salts, or tautomerism isomers thereof.

Another embodiment of present invention is (iv) a compound of formula I or a pharmaceutically acceptable salt or tautomerism isomers thereof, wherein $R^1$ is $C_{1-2}$alkoxycarbonyl;
$R^2$ is phenyl which is once substituted by halogen;
$R^3$ is 2-thiazolyl;
X is oxygen;
$R^4$ and $R^5$ are independently selected from hydrogen, $C_{1-6}$alkyl and trifluoro$C_{1-6}$alkyl;
M is $C_{1-6}$alkoxycarbonyl or carboxy.

Further embodiment of present invention is (v) a compound of formula I or a pharmaceutically acceptable salt or tautomerism isomers thereof, wherein $R^1$ is methyoxycarbonyl;
$R^2$ is 4-fluorophenyl;
$R^3$ is thiazol-2-yl;
X is oxygen;
$R^4$ and $R^5$ are independently selected from hydrogen, methyl and trifluoromethyl;
M is methoxycarbonyl or carboxy.

Another embodiment of present invention is (vi) a compound of formula I or a pharmaceutically acceptable salt or tautomerism isomers thereof, wherein $R^1$ is $C_{1-2}$alkoxycarbonyl;
$R^2$ is phenyl which is once substituted by halogen;
$R^3$ is 2-thiazolyl;
X is —N—$C_{1-6}$alkyl or —N-trifluoro$C_{1-6}$alkyl;
$R^4$ is hydrogen;
$R^5$ is hydrogen;
or $R^4$ and $R^5$, together with the carbon atom to which they are attached, form a 3 to 7 membered cycloalkyl;
M is carboxy.

Further embodiment of present invention is (vii) a compound of formula I or a pharmaceutically acceptable salt or tautomerism isomers thereof, wherein $R^1$ is methoxycarbonyl;
$R^2$ is 4-fluorophenyl;
$R^3$ is thiazol-2-yl;
X is —NCH₃ or —NCH₂CF₃;
$R^4$ is hydrogen;
$R^5$ is hydrogen;
or $R^4$ and $R^5$, together with the carbon atom to which they are attached, form cyclopropyl;
M is carboxy.

Another embodiment of present invention is (viii) a compound of formula I or a pharmaceutically acceptable salt or tautomerism isomers thereof, wherein $R^1$ is $C_{1-2}$alkoxycarbonyl or cyano;
$R^2$ is phenyl which is once or twice substituted by halogen;

$R^3$ is 2-thiazolyl; or 2-pyridinyl, which is once substituted by halogen; or 2-imidazolyl, which is once substituted by $C_{1-6}$alkyl;
X is —NR⁷;
one of $R^4$ and $R^5$ is hydrogen, and the other of $R^4$ and $R^5$ along with R⁷ and the atoms to which $R^4$ or $R^5$ and R⁷ are attached form a morpholinyl;
M is $C_{1-6}$alkoxycarbonyl, carboxy or hydroxy-$C_yH_{2y}$—;
y is 1-6.

Further embodiment of present invention is (ix) a compound of formula I or a pharmaceutically acceptable salt or tautomerism isomers thereof, wherein $R^1$ is methoxycarbonyl, ethoxycarbonyl or cyano;
$R^2$ is 4-fluorophenyl or 3,4-difluorophenyl;
$R^3$ is thiazol-2-yl, 5-fluoro-pyridin-2-yl or 1-methyl-imidazolid-2-yl;
one of $R^4$ and $R^5$ along with R⁷ and the atoms to which $R^4$ or $R^5$ and R⁷ are attached form:

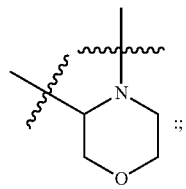 [SMILES: *C1COCCN1*]

M is methoxycarbonyl, carboxy or hydroxymethyl-.

Another embodiment of present invention is (x) a compound of formula I or a pharmaceutically acceptable salt or tautomerism isomers thereof, wherein $R^1$ is $C_{1-2}$alkoxycarbonyl or cyano;
$R^2$ is phenyl which is once or twice substituted by halogen;
$R^3$ is 2-thiazolyl, which is unsubstituted or once substituted by $C_{1-6}$alkyl or halogen; or 2-thienyl or 2-pyridinyl, which is once substituted by halogen; or 2-imidazolyl, which is once substituted by $C_{1-6}$alkyl; or 3-isoxazolyl, which is unsubstituted or once substituted by $C_{1-6}$alkyl;
X is —NR⁷;
one of $R^4$ and $R^5$ is hydrogen or $C_{1-6}$alkyl, and the other of $R^4$ and $R^5$ along with R⁷ and the atoms to which $R^4$ or $R^5$ and R⁷ are attached form a pyrrolidinyl or piperidinyl, which is substituted by fluoro;
M is $C_{1-6}$alkoxycarbonyl, carboxy, di$C_{1-6}$alkylamino $C_{2-6}$alkoxycarbonyl, aminocarbonyl, $C_{1-6}$alkylaminocarbonyl, di$C_{1-6}$alkylaminocarbonyl, $C_{1-6}$alkylsulfonylaminocarbonyl, 2-thiazolylaminocarbonyl, hydroxy-$C_yH_{2y}$—,

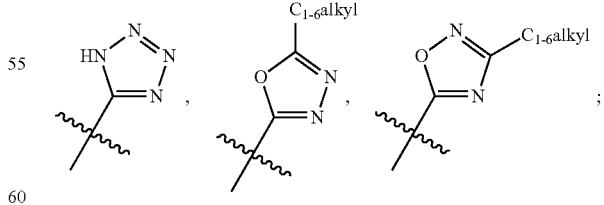

y is 1-6.

Further embodiment of present invention is (xi) a compound of formula I or a pharmaceutically acceptable salt or tautomerism isomers thereof, wherein $R^1$ is methoxycarbonyl, ethoxycarbonyl or cyano;
$R^2$ is 4-fluorophenyl or 3,4-difluorophenyl;

R³ is

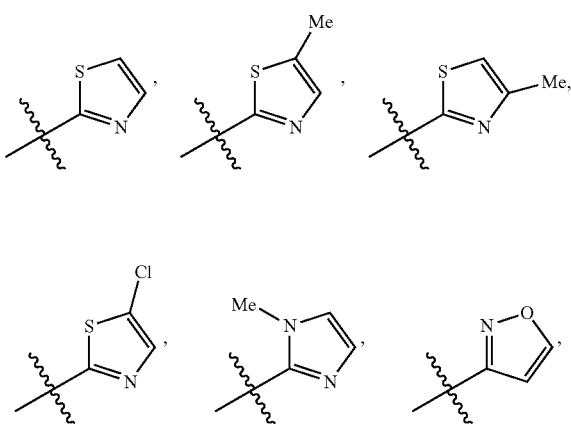

X is —NR⁷;
one of R⁴ and R⁵ is hydrogen or methyl, and the other of R⁴ and R⁵ along with R⁷ and the atoms to which R⁴ or R⁵ and R⁷ are attached form

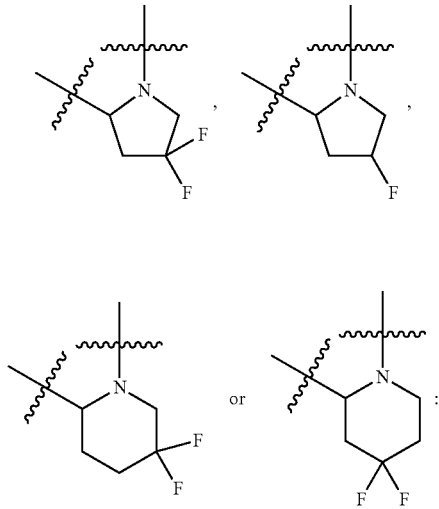

M is methoxycarbonyl, carboxy, dimethylaminoethoxycarbonyl, aminocarbonyl, dimethylaminocarbonyl, methylaminocarbonyl, methylsulfonylaminocarbonyl, 2-thiazolylaminocarbonyl, hydroxymethyl, hydroxypropyl, —C(Me)₂OH,

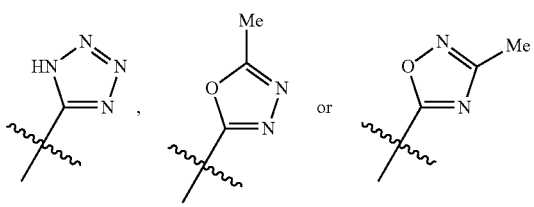

Another embodiment of present invention is (xii) a compound of formula I' or a pharmaceutically acceptable salt or tautomerism isomers thereof,

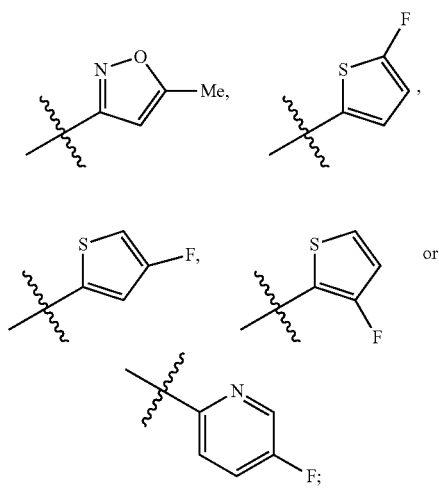

(I')

wherein

R¹ is $C_{1-2}$alkoxycarbonyl or cyano;

R² is phenyl, which is substituted by halogen;

R³ is 2-thiazolyl which is unsubstituted or substituted by $C_{1-6}$alkyl or 2-pyridinyl, which is substituted by halogen;

X is oxygen or —NR⁷;

R⁴ and R⁵ are independently selected from hydrogen, $C_{1-6}$alkyl and trifluoro$C_{1-6}$alkyl; or R⁴ and R⁵, together with the carbon atom to which they are attached, form a 3 to 7 membered cycloalkyl; or when X is —NR⁷, one of R⁴ and R⁵ is hydrogen or $C_{1-6}$alkyl, and the other of R⁴ and R⁵ along with R⁷ and the atoms to which R⁴ or R⁵ and R⁷ are attached form a morpholinyl; or pyrrolidinyl substituted by fluoro;

R⁶ is hydrogen or $C_{1-6}$alkyl;

R⁷ is $C_{1-6}$alkyl.

Further embodiment of present invention is (xiii) a compound of formula I' or a pharmaceutically acceptable salt or tautomerism isomers thereof, wherein R¹ is methoxycarbonyl or cyano;

R² is phenyl substituted once or twice by fluoro;

R³ is thiazol-2-yl, 5-methyl-thiazol-2-yl or 5-fluoro-pyridin-2-yl; or;

X is oxygen or —NR⁷;

R⁴ and R⁵ are independently selected from hydrogen, methyl and trifluoromethyl; or R⁴ and R⁵ together with the carbon atom to which they are attached form cyclopropyl; or when X is —NR⁷, one of R⁴ and R⁵ is hydrogen or methyl and the other of R⁴ and R⁵ along with R⁷ and the atoms to which R⁴ or R⁵ and R⁷ are attached form

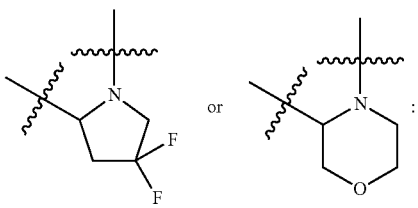 [SMILES: *C1CC(F)(F)CN1* ; *C1COCCN1*]

R⁶ is hydrogen or methyl;
R⁷ is methyl.

Still further embodiment of present invention is (xiv) a compound of formula I' or a pharmaceutically acceptable salt or tautomerism isomers thereof, wherein
R¹ is $C_{1-2}$alkoxycarbonyl;
R² is phenyl which is substituted by halogen;
R³ is 2-thiazolyl;
X is oxygen;
R⁴ and R⁵ are independently selected from hydrogen, $C_{1-6}$alkyl and trifluoro$C_{1-6}$alkyl;
R⁶ is hydrogen or $C_{1-6}$alkyl.

More further embodiment of present invention is (xv) a compound of formula I' or a pharmaceutically acceptable salt or tautomerism isomers thereof, wherein
R¹ is methyoxycarbonyl;
R² is 4-fluorophenyl;
R³ is thiazolidin-2-yl;
X is oxygen;
R⁴ and R⁵ are independently selected from hydrogen, methyl and trifluoromethyl;
R⁶ is hydrogen or methyl.

Another further embodiment of present invention is (xvi) a compound of formula I' or a pharmaceutically acceptable salt or tautomerism isomers thereof, wherein
R¹ is $C_{1-2}$alkoxycarbonyl;
R² is phenyl which is substituted by halogen;
R³ is 2-thiazolyl;
X is $NC_{1-6}$alkyl;
R⁴ and R⁵, together with the carbon atom to which they are attached, form a 3 to 7 membered cycloalkyl;
R⁶ is hydrogen.

Further embodiment of present invention is (xvii) a compound of formula I' or a pharmaceutically acceptable salt or tautomerism isomers thereof, wherein
R¹ is methoxycarbonyl;
R² is 4-fluorophenyl;
R³ is thiazolidin-2-yl;
X is —NCH₃;
R⁴ and R⁵, together with the carbon atom to which they are attached, form cyclopropyl;
R⁶ is hydrogen.

More further embodiment of present invention is (xviii) a compound of formula I' or a pharmaceutically acceptable salt or tautomerism isomers thereof, wherein
R¹ is $C_{1-2}$alkoxycarbonyl or cyano;
R² is phenyl which is substituted by halogen;
R³ is 2-thiazolyl; or 2-pyridinyl, which is substituted by halogen;
X is —NR⁷;
one of R⁴ and R⁵ is hydrogen or $C_{1-6}$alkyl, and the other of R⁴ and R⁵ along with R⁷ and the atoms to which R⁴ or R⁵ and R⁷ are attached form

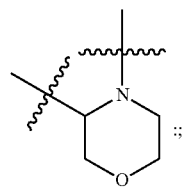 [SMILES: *C1COCCN1*]

R⁶ is hydrogen or $C_{1-6}$alkyl.

Further embodiment of present invention is (xix) a compound of formula I' or a pharmaceutically acceptable salt or tautomerism isomers thereof, wherein
R¹ is methoxycarbonyl or cyano;
R² is 4-fluorophenyl or 3,4-difluorophenyl;
R³ is thiazolidin-2-yl or 5-fluoro-pyridin-2-yl,
one of R⁴ and R⁵ is hydrogen or methyl, and the other of R⁴ and R⁵ along with R⁷ and the atoms to which R⁴ or R⁵ and R⁷ are attached form

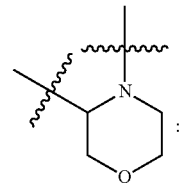 [SMILES: *C1COCCN1*]

R⁶ is hydrogen or methyl.

Still further embodiment of present invention is (xx) a compound of formula I' or a pharmaceutically acceptable salt or tautomerism isomers thereof, wherein
R¹ is $C_{1-2}$alkoxycarbonyl or cyano;
R² is phenyl which is substituted by halogen;
R³ is 2-thiazolyl which is unsubstituted or substituted by $C_{1-6}$alkyl or 2-pyridinyl, which is substituted by halogen;
X is —NR⁷;
one of R⁴ and R⁵ is hydrogen or $C_{1-6}$alkyl, and the other of R⁴ and R⁵ along with R⁷ and the atoms to which R⁴ or R⁵ and R⁷ are attached form pyrrolidinyl substituted by fluoro;
R⁶ is hydrogen or $C_{1-6}$alkyl.

Another further embodiment of present invention is (xxi) a compound of formula I' or a pharmaceutically acceptable salt or tautomerism isomers thereof, wherein
R¹ is methoxycarbonyl or cyano;
R² is 4-fluorophenyl or 3,4-difluorophenyl;
R³ is thiazol-2-yl, 5-methyl-thiazol-2-yl or 5-fluoro-pyridin-2-yl; or;
X is —NR⁷;
one of R⁴ and R⁵ is hydrogen or methyl, and the other of R⁴ and R⁵ along with R⁷ and the atoms to which R⁴ or R⁵ and R⁷ are attached form

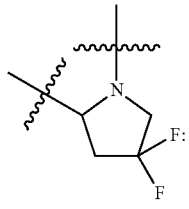

R⁶ is hydrogen or methyl.

Particular compounds of formula I, including their activity data, NMR data and MS data are summarized in the following Table 1 and 2.

TABLE 1

Structure, name and activity data of particular compounds

| Example No. | Structure | Name | HepDe19 EC50 (μM) | CC50 (μM) |
|---|---|---|---|---|
| 1 | 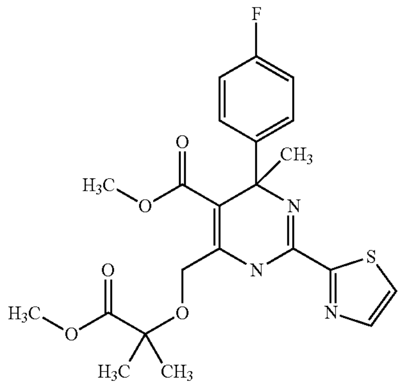 [SMILES: COC(=O)C1=C(COC(C)(C)C(=O)OC)NC(c2nccs2)=NC1(C)c1ccc(F)cc1] | 4-(4-Fluoro-phenyl)-6-(1-methoxycarbonyl-1-methyl-ethoxymethyl)-4-methyl-2-thiazol-2-yl-1,4-dihydro-pyrimidine-5-carboxylic acid methyl ester | 26.29 | >100 |
| 2 | 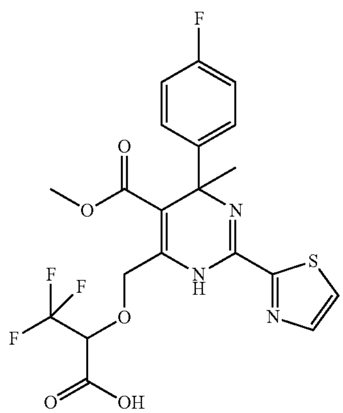 [SMILES: COC(=O)C1=C(COC(C(=O)O)C(F)(F)F)NC(c2nccs2)=NC1(C)c1ccc(F)cc1] | 6-(1-Carboxy-2,2,2-trifluoro-ethoxymethyl)-4-(4-fluoro-phenyl)-4-methyl-2-thiazol-2-yl-1,4-dihydro-pyrimidine-5-carboxylic acid methyl ester | 24.43 | >100 |
| 3 | 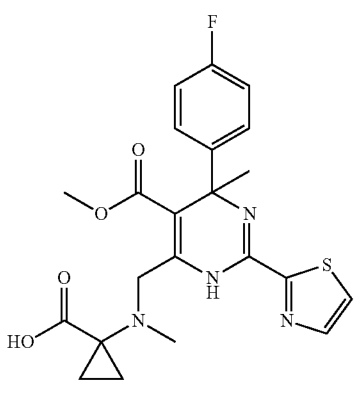 [SMILES: COC(=O)C1=C(CN(C)C2(C(=O)O)CC2)NC(c2nccs2)=NC1(C)c1ccc(F)cc1] | 6-{[(1-Carboxy-cyclopropyl)-methyl-amino]-methyl}-4-(4-fluoro-phenyl)-4-methyl-2-thiazol-2-yl-1,4-dihydro-pyrimidine-5-carboxylic acid methyl ester | 21.31 | >100 |

TABLE 1-continued

Structure, name and activity data of particular compounds

| Example No. | Structure | Name | HepDe19 EC50 (μM) | CC50 (μM) |
|---|---|---|---|---|
| 4 | 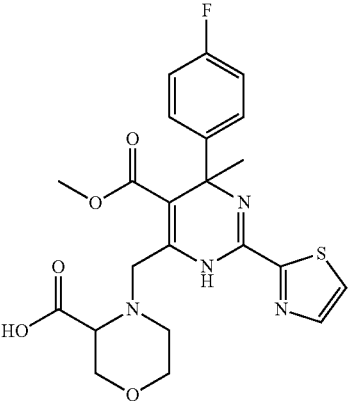 [SMILES: COC(=O)C1=C(CN2CCOCC2C(=O)O)NC(c2nccs2)=NC1(C)c1ccc(F)cc1] | 4-[6-(4-Fluoro-phenyl)-5-methoxycarbonyl-6-methyl-2-thiazol-2-yl-3,6-dihydro-pyrimidin-4-ylmethyl]-morpholine-3-carboxylic acid | 1.46 | >100 |
| 5 | 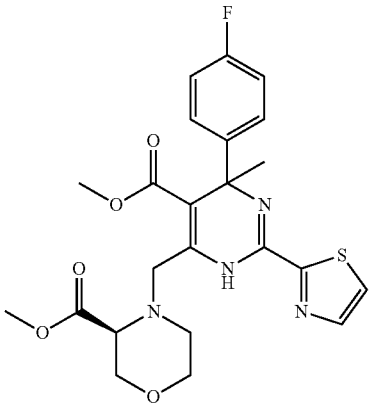 [SMILES: COC(=O)C1=C(CN2CCOC[C@H]2C(=O)OC)NC(c2nccs2)=NC1(C)c1ccc(F)cc1] | 4-[6-(4-Fluoro-phenyl)-5-methoxycarbonyl-6-methyl-2-thiazol-2-yl-3,6-dihydro-pyrimidin-4-ylmethyl]-morpholine-(S)-3-carboxylic acid methyl ester | 0.7 | >100 |
| 6 | 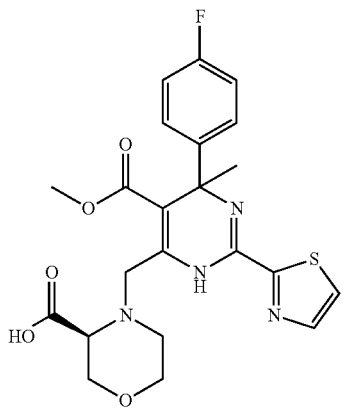 [SMILES: COC(=O)C1=C(CN2CCOC[C@H]2C(=O)O)NC(c2nccs2)=NC1(C)c1ccc(F)cc1] | 4-[6-(4-Fluoro-phenyl)-5-methoxycarbonyl-6-methyl-2-thiazol-2-yl-3,6-dihydro-pyrimidin-4-ylmethyl]-morpholine-(S)-3-carboxylic acid | 1.2 | >100 |

TABLE 1-continued

Structure, name and activity data of particular compounds

| Example No. | Structure | Name | HepDe19 EC50 (μM) | CC50 (μM) |
|---|---|---|---|---|
| 7 | 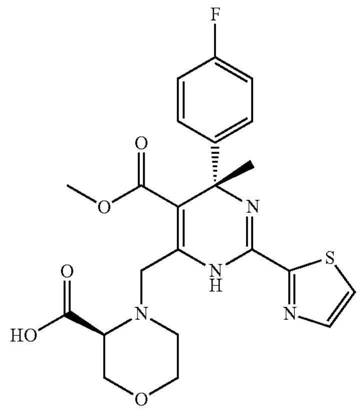 [SMILES: COC(=O)C1=C(CN2CCOC[C@H]2C(=O)O)NC(c2nccs2)=N[C@@]1(C)c1ccc(F)cc1] | (S)-4-[6-(4-Fluoro-phenyl)-5-methoxycarbonyl-6-methyl-2-thiazol-2-yl-3,6-dihydro-pyrimidin-4-ylmethyl]-morpholine-(S)-3-carboxylic acid | 0.77 | >100 |
| 8 | 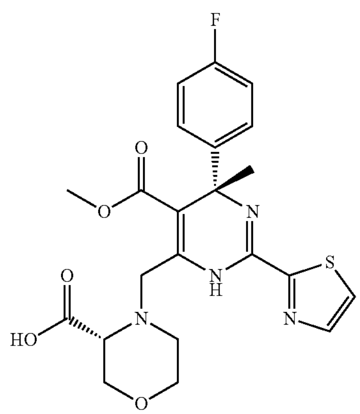 [SMILES: COC(=O)C1=C(CN2CCOC[C@@H]2C(=O)O)NC(c2nccs2)=N[C@@]1(C)c1ccc(F)cc1] | (S)-4-[6-(4-Fluoro-phenyl)-5-methoxycarbonyl-6-methyl-2-thiazol-2-yl-3,6-dihydro-pyrimidin-4-ylmethyl]-morpholine-(R)-3-carboxylic acid | 3.01 | >100 |
| 9 | 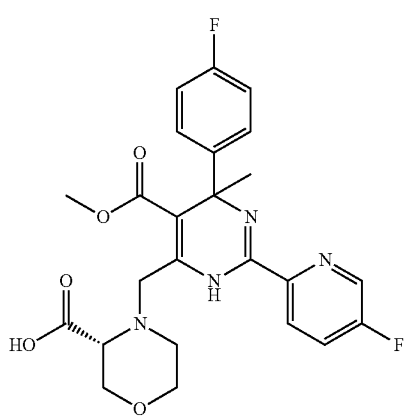 [SMILES: COC(=O)C1=C(CN2CCOC[C@@H]2C(=O)O)NC(c2ccc(F)cn2)=NC1(C)c1ccc(F)cc1] | 4-[6-(4-Fluoro-phenyl)-2-(5-fluoro-pyridin-2-yl)-5-methoxycarbonyl-6-methyl-3,6-dihydro-pyrimidin-4-ylmethyl]-morpholine-(R)-3-carboxylic acid | 4.18 | >100 |

TABLE 1-continued

Structure, name and activity data of particular compounds

| Example No. | Structure | Name | HepDe19 EC50 (μM) | CC50 (μM) |
|---|---|---|---|---|
| 10 | 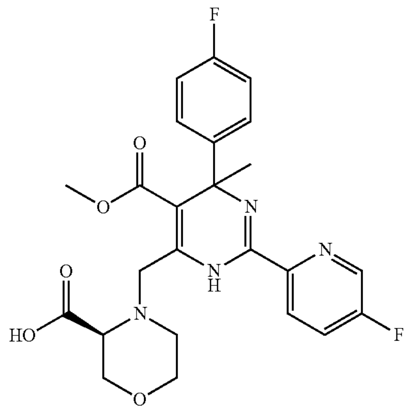 [SMILES: COC(=O)C1=C(CN2CCOC[C@H]2C(=O)O)NC(c2ccc(F)cn2)=NC1(C)c1ccc(F)cc1] | 4-[6-(4-Fluoro-phenyl)-2-(5-fluoro-pyridin-2-yl)-5-methoxycarbonyl-6-methyl-3,6-dihydro-pyrimidin-4-ylmethyl]-morpholine-(S)-3-carboxylic acid | 7.04 | >100 |
| 11 | 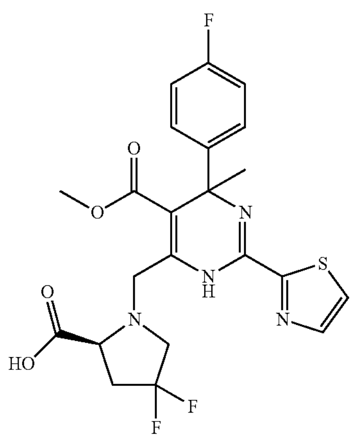 [SMILES: COC(=O)C1=C(CN2CC(F)(F)C[C@H]2C(=O)O)NC(c2nccs2)=NC1(C)c1ccc(F)cc1] | 6-(2-(S)-Carboxy-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester | 0.46 | 95.5 |
| 12 | 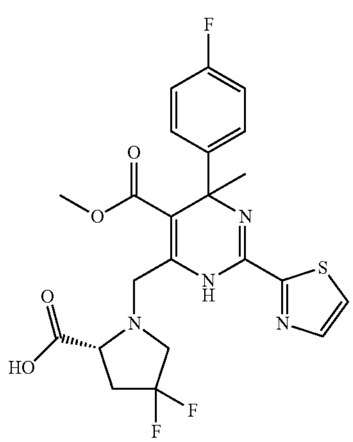 [SMILES: COC(=O)C1=C(CN2CC(F)(F)C[C@@H]2C(=O)O)NC(c2nccs2)=NC1(C)c1ccc(F)cc1] | 6-(2-(R)-Carboxy-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester | 6.59 | 82 |

TABLE 1-continued

Structure, name and activity data of particular compounds

| Example No. | Structure | Name | HepDe19 EC50 (μM) | CC50 (μM) |
|---|---|---|---|---|
| 13 | 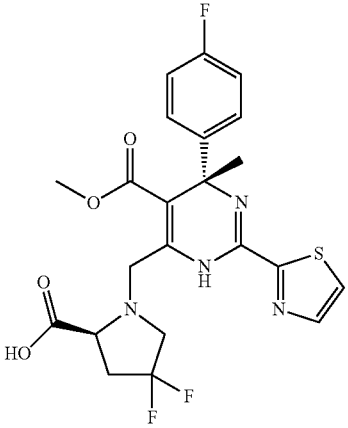 [SMILES: COC(=O)C1=C(CN2CC(F)(F)C[C@H]2C(=O)O)NC(c2nccs2)=N[C@@]1(C)c1ccc(F)cc1] | (S)-6-((S)-2-Carboxy-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester | 0.15 | >100 |
| 14 | 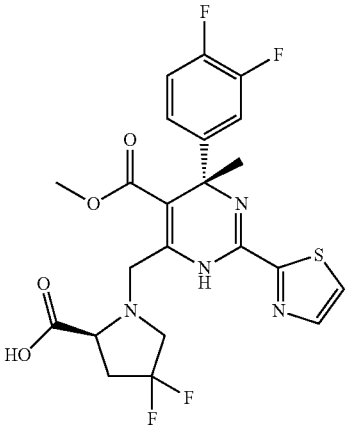 [SMILES: COC(=O)C1=C(CN2CC(F)(F)C[C@H]2C(=O)O)NC(c2nccs2)=N[C@@]1(C)c1ccc(F)c(F)c1] | (S)-6-((S)-2-Carboxy-4,4-difluoro-pyrrolidin-1-ylmethyl)-4-(3,4-difluoro-phenyl)-4-methyl-2-thiazol-2-yl-1,4-dihydro-pyrimidine-5-carboxylic acid methyl ester | 0.2 | >100 |
| 15 | 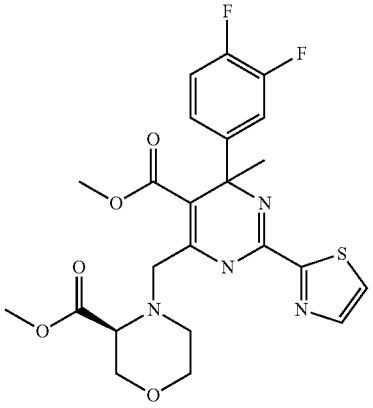 [SMILES: COC(=O)C1=C(CN2CCOC[C@H]2C(=O)OC)NC(c2nccs2)=NC1(C)c1ccc(F)c(F)c1] | 4-[(S)-6-(3,4-Difluoro-phenyl)-5-methoxycarbonyl-6-methyl-2-thiazol-2-yl-3,6-dihydro-pyrimidin-4-ylmethyl]-morpholine-3-carboxylic acid methyl ester | 0.56 | >100 |

TABLE 1-continued

Structure, name and activity data of particular compounds

| Example No. | Structure | Name | HepDe19 EC50 (µM) | CC50 (µM) |
|---|---|---|---|---|
| 16 | 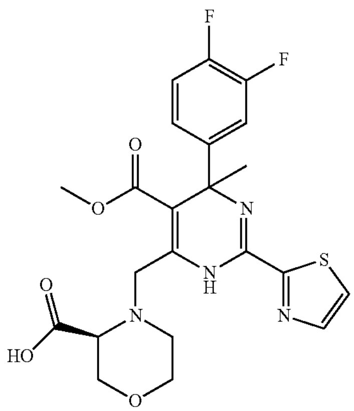 [SMILES: COC(=O)C1=C(CN2CCOC[C@H]2C(=O)O)NC(c2nccs2)=NC1(C)c1ccc(F)c(F)c1] | 4-[6-(3,4-Difluoro-phenyl)-5-methoxycarbonyl-6-methyl-2-thiazol-2-yl-3,6-dihydro-pyrimidin-4-ylmethyl]-morpholine-3-carboxylic acid | 0.25 | >100 |
| 17 | 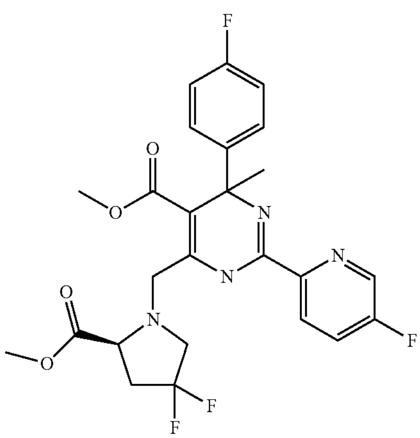 [SMILES: COC(=O)C1=C(CN2CC(F)(F)C[C@H]2C(=O)OC)NC(c2ccc(F)cn2)=NC1(C)c1ccc(F)cc1] | 6-(4,4-Difluoro-2-methoxycarbonyl-pyrrolidin-1-ylmethyl)-4-(4-fluoro-phenyl)-2-(5-fluoro-pyridin-2-yl)-4-methyl-1,4-dihydro-pyrimidine-5-carboxylic acid methyl ester | 0.59 | 90 |
| 18 | 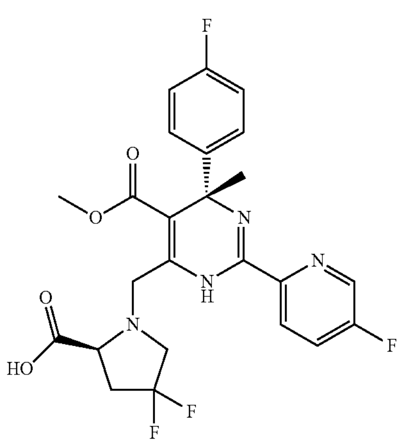 [SMILES: COC(=O)C1=C(CN2CC(F)(F)C[C@H]2C(=O)O)NC(c2ccc(F)cn2)=N[C@@]1(C)c1ccc(F)cc1] | 6-(2-Carboxy-4,4-difluoro-pyrrolidin-1-ylmethyl)-4-(4-fluoro-phenyl)-2-(5-fluoro-pyridin-2-yl)-4-methyl-1,4-dihydro-pyrimidine-5-carboxylic acid methyl ester | 0.57 | 25 |

TABLE 1-continued

Structure, name and activity data of particular compounds

| Example No. | Structure | Name | HepDe19 EC50 (μM) | CC50 (μM) |
|---|---|---|---|---|
| 19 | 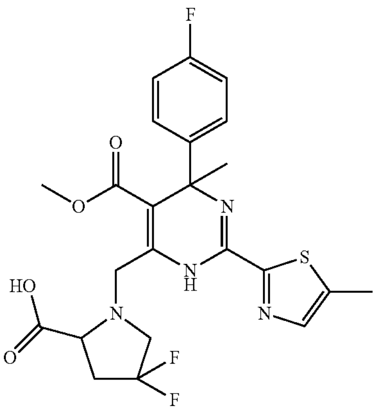 [SMILES: COC(=O)C1=C(CN2CC(F)(F)CC2C(=O)O)NC(c2ncc(C)s2)=NC1(C)c1ccc(F)cc1] | 6-(2-Carboxy-4,4-difluoro-pyrrolidin-1-ylmethyl)-4-(4-fluoro-phenyl)-4-methyl-2-(5-methyl-thiazol-2-yl)-1,4-dihydro-pyrimidine-5-carboxylic acid methyl ester | 16.7 | >100 |
| 20 | 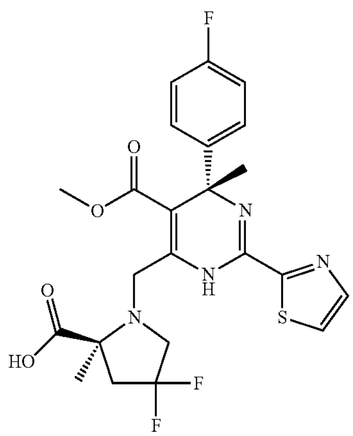 [SMILES: COC(=O)C1=C(CN2CC(F)(F)C[C@@]2(C)C(=O)O)NC(c2nccs2)=N[C@@]1(C)c1ccc(F)cc1] | (S)-6-((S)-2-Carboxy-4,4-difluoro-2-methyl-pyrrolidin-1-ylmethyl)-4-(4-fluoro-phenyl)-4-methyl-2-thiazol-2-yl-1,4-dihydro-pyrimidine-5-carboxylic acid methyl ester | 2.8 | >100 |
| 21 | 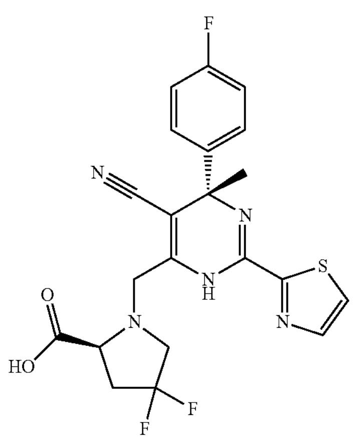 [SMILES: C[C@@]1(c2ccc(F)cc2)N=C(c2nccs2)NC(CN2CC(F)(F)C[C@H]2C(=O)O)=C1C#N] | (S)-1-[(S)-5-Cyano-6-(4-fluoro-phenyl)-6-methyl-2-thiazol-2-yl-3,6-dihydro-pyrimidin-4-ylmethyl]-4,4-difluoro-pyrrolidine-2-carboxylic acid | 21 | >100 |

TABLE 1-continued

Structure, name and activity data of particular compounds

| Example No. | Structure | Name | HepDe19 EC50 (μM) | CC50 (μM) |
|---|---|---|---|---|
| 22 | 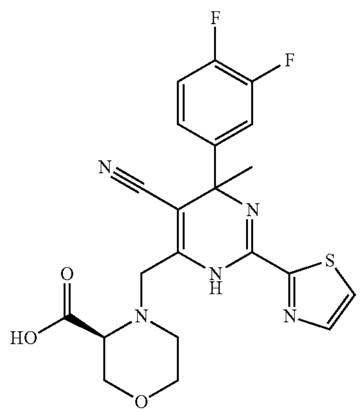 [SMILES: CC1(c2ccc(F)c(F)c2)N=C(c2nccs2)NC(CN2CCOC[C@H]2C(=O)O)=C1C#N] | (S)-4-[5-Cyano-6-(3,4-difluoro-phenyl)-6-methyl-2-thiazol-2-yl-3,6-dihydro-pyrimidin-4-ylmethyl]-morpholine-3-carboxylic acid | 20.4 | >100 |
| 23 | 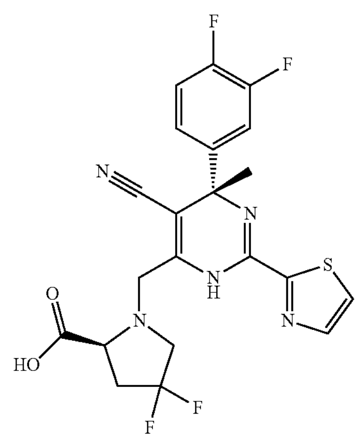 [SMILES: C[C@@]1(c2ccc(F)c(F)c2)N=C(c2nccs2)NC(CN2CC(F)(F)C[C@H]2C(=O)O)=C1C#N] | (S)-1-[(S)-5-Cyano-6-(3,4-difluoro-phenyl)-6-methyl-2-thiazol-2-yl-3,6-dihydro-pyrimidin-4-ylmethyl]-4,4-difluoro-pyrrolidine-2-carboxylic acid | 7 | >100 |
| 24 | 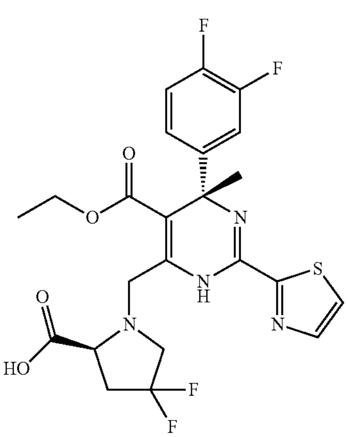 [SMILES: CCOC(=O)C1=C(CN2CC(F)(F)C[C@H]2C(=O)O)NC(c2nccs2)=N[C@@]1(C)c1ccc(F)c(F)c1] | (S)-6-((S)-2-Carboxy-4,4-difluoro-pyrrolidin-1-ylmethyl)-4-(3,4-difluoro-phenyl)-4-methyl-2-thiazol-2-yl-1,4-dihydro-pyrimidine-5-carboxylic acid ethyl ester | 0.8 | 100 |

TABLE 1-continued

Structure, name and activity data of particular compounds

| Example No. | Structure | Name | HepDe19 EC50 (μM) | CC50 (μM) |
|---|---|---|---|---|
| 25 | 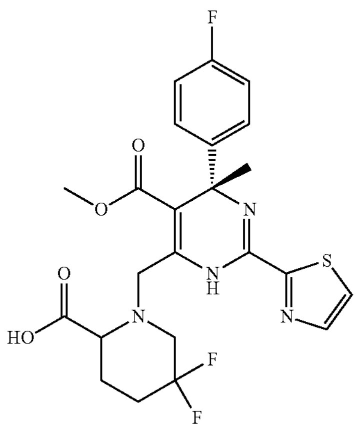 [SMILES: COC(=O)C1=C(CN2CC(F)(F)CCC2C(=O)O)NC(c2nccs2)=N[C@@]1(C)c1ccc(F)cc1] | (S)-6-(2-Carboxy-5,5-difluoro-piperidin-1-ylmethyl)-4-(4-fluoro-phenyl)-4-methyl-2-thiazol-2-yl-1,4-dihydro-pyrimidine-5-carboxylic acid methyl ester | 1.09 | 100 |
| 26 | 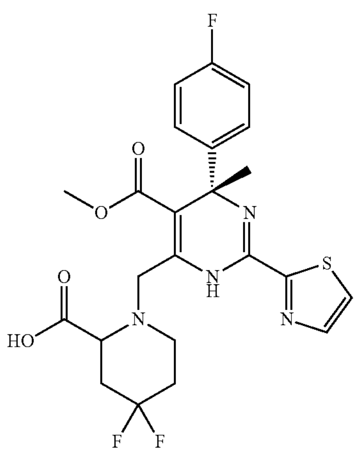 [SMILES: COC(=O)C1=C(CN2CCC(F)(F)CC2C(=O)O)NC(c2nccs2)=N[C@@]1(C)c1ccc(F)cc1] | (S)-6-(2-Carboxy-4,4-difluoro-piperidin-1-ylmethyl)4-(4-fluoro-phenyl)-4-methyl-2-thiazol-2-yl-1,4-dihydro-pyrimidine-5-carboxylic acid methyl ester | 1.97 | 100 |
| 27 | 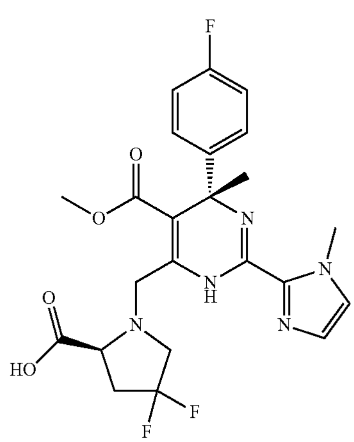 [SMILES: COC(=O)C1=C(CN2CC(F)(F)C[C@H]2C(=O)O)NC(c2nccn2C)=N[C@@]1(C)c1ccc(F)cc1] | (S)-6-((S)-2-Carboxy-4,4-difluoro-pyrrolidin-1-ylmethyl)-4-(4-fluoro-phenyl)-4-methyl-2-(1-methyl-1H-imidazol-2-yl)-1,4-dihydro-pyrimidine-5-carboxylic acid methyl ester | 2.72 | 55.8 |

TABLE 1-continued

Structure, name and activity data of particular compounds

| Example No. | Structure | Name | HepDe19 EC50 (μM) | CC50 (μM) |
|---|---|---|---|---|
| 28 | 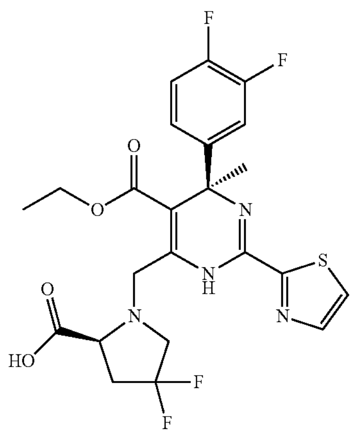 [SMILES: CCOC(=O)C1=C(CN2CC(F)(F)C[C@H]2C(=O)O)NC(c2nccs2)=N[C@]1(C)c1ccc(F)c(F)c1] | (R)-6-((S)-2-Carboxy-4,4-difluoro-pyrrolidin-1-ylmethyl)-4-(3,4-difluoro-phenyl)-4-methyl-2-thiazol-2-yl-1,4-dihydro-pyrimidine-5-carboxylic acid ethyl ester | 7.48 | 100 |
| 29 | 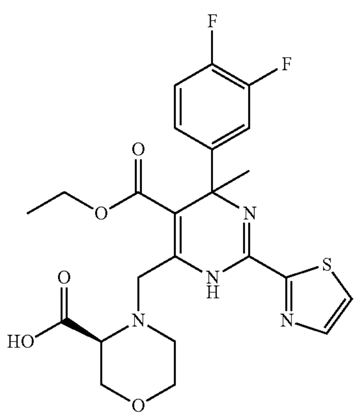 [SMILES: CCOC(=O)C1=C(CN2CCOC[C@H]2C(=O)O)NC(c2nccs2)=NC1(C)c1ccc(F)c(F)c1] | (S)-4-[6-(3,4-Difluoro-phenyl)-5-ethoxycarbonyl-6-methyl-2-thiazol-2-yl-3,6-dihydro-pyrimidin-4-ylmethyl]-morpholine-3-carboxylic acid | 3.98 | 100 |
| 30 | 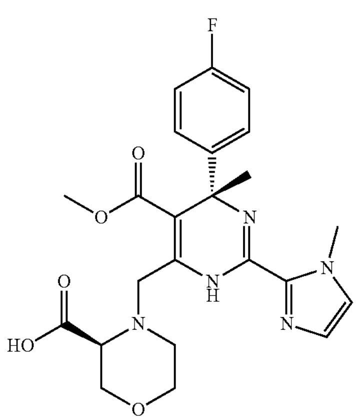 [SMILES: COC(=O)C1=C(CN2CCOC[C@H]2C(=O)O)NC(c2nccn2C)=N[C@@]1(C)c1ccc(F)cc1] | (S)-4-[(S)-6-(4-Fluoro-phenyl)-5-methoxycarbonyl-6-methyl-2-(1-methyl-1H-imidazol-2-yl)-3,6-dihydro-pyrimidin-4-ylmethyl]-morpholine-3-carboxylic acid | 6.77 | 100 |

TABLE 1-continued

Structure, name and activity data of particular compounds

| Example No. | Structure | Name | HepDe19 EC50 (µM) | CC50 (µM) |
|---|---|---|---|---|
| 31 | 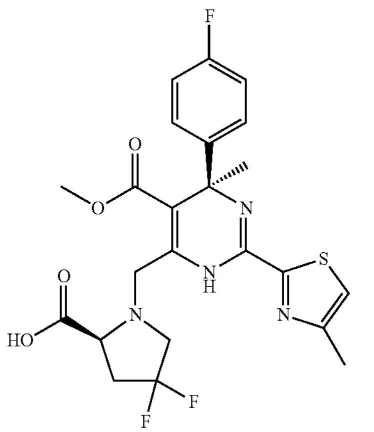 [SMILES: COC(=O)C1=C(CN2CC(F)(F)C[C@H]2C(=O)O)NC(c2nc(C)cs2)=N[C@]1(C)c1ccc(F)cc1] | (R)-6-((S)-2-Carboxy-4,4-difluoro-pyrrolidin-1-ylmethyl)-4-(4-fluoro-phenyl)-4-methyl-2-(4-methyl-thiazol-2-yl)-1,4-dihydro-pyrimidine-5-carboxylic acid methyl ester | 1.67 | 100 |
| 32 | 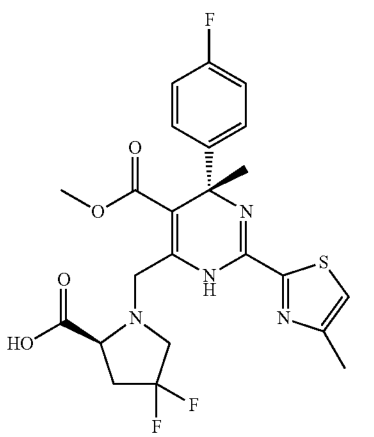 [SMILES: COC(=O)C1=C(CN2CC(F)(F)C[C@H]2C(=O)O)NC(c2nc(C)cs2)=N[C@@]1(C)c1ccc(F)cc1] | (S)-6-((S)-2-Carboxy-4,4-difluoro-pyrrolidin-1-ylmethyl)-4-(4-fluoro-phenyl)-4-methyl-2-(4-methyl-thiazol-2-yl)-1,4-dihydro-pyrimidine-5-carboxylic acid methyl ester | 0.13 | 75 |
| 33 | 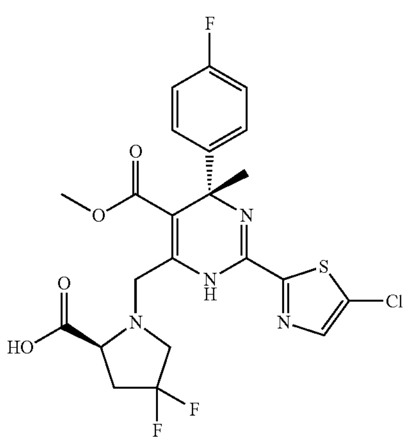 [SMILES: COC(=O)C1=C(CN2CC(F)(F)C[C@H]2C(=O)O)NC(c2ncc(Cl)s2)=N[C@@]1(C)c1ccc(F)cc1] | (S)-6-((S)-2-Carboxy-4,4-difluoro-pyrrolidin-1-ylmethyl)-2-(5-chloro-thiazol-2-yl)-4-(4-fluoro-phenyl)-4-methyl-1,4-dihydro-pyrimidine-5-carboxylic acid methyl ester | 2.07 | 80 |

TABLE 1-continued

Structure, name and activity data of particular compounds

| Example No. | Structure | Name | HepDe19 EC50 (μM) | CC50 (μM) |
|---|---|---|---|---|
| 34 | 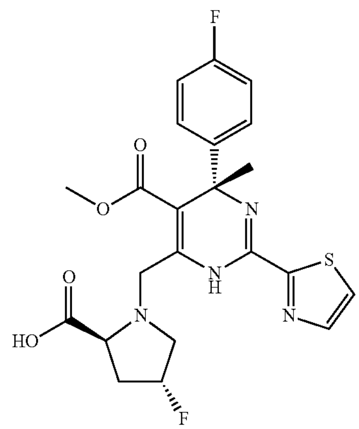 [SMILES: COC(=O)C1=C(CN2C[C@H](F)C[C@H]2C(=O)O)NC(c2nccs2)=N[C@@]1(C)c1ccc(F)cc1] | (S)-6-(2S,4R)-2-Carboxy-4-fluoro-pyrrolidin-1-ylmethyl)-4-(4-fluoro-phenyl)-4-methyl-2-thiazol-2-yl-1,4-dihydro-pyrimidine-5-carboxylic acid methyl ester | 2.84 | 100 |
| 35 | 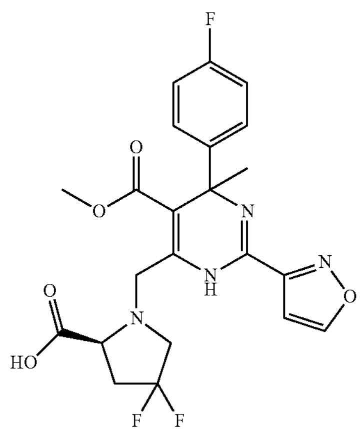 [SMILES: COC(=O)C1=C(CN2CC(F)(F)C[C@H]2C(=O)O)NC(c2ccon2)=NC1(C)c1ccc(F)cc1] | 6-((S)-2-Carboxy-4,4-difluoro-pyrrolidin-1-ylmethyl)-4-(4-fluoro-phenyl)-2-isoxazol-3-yl-4-methyl-1,4-dihydro-pyrimidine-5-carboxylic acid methyl ester | 15 | 100 |
| 36 | 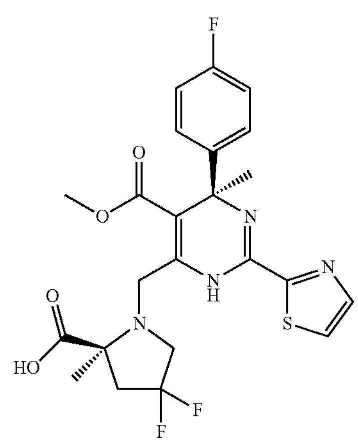 [SMILES: COC(=O)C1=C(CN2CC(F)(F)C[C@@]2(C)C(=O)O)NC(c2nccs2)=N[C@]1(C)c1ccc(F)cc1] | (R)-6-((S)-2-Carboxy-4,4-difluoro-2-methyl-pyrrolidin-1-ylmethyl)-4-(4-fluoro-phenyl)-4-methyl-2-thiazol-2-yl-1,4-dihydro-pyrimidine-5-carboxylic acid methyl ester | 7.49 | 100 |

TABLE 1-continued

Structure, name and activity data of particular compounds

| Example No. | Structure | Name | HepDe19 EC50 (μM) | CC50 (μM) |
|---|---|---|---|---|
| 37 | 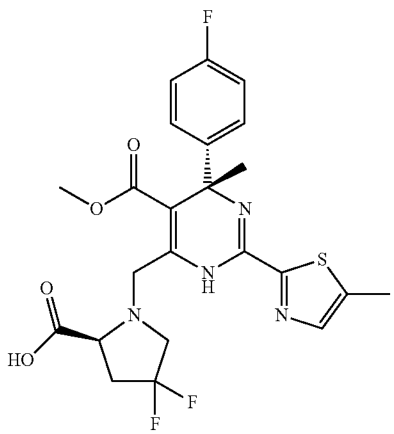 | (S)-6-((S)-2-Carboxy-4,4-difluoro-pyrrolidin-1-ylmethyl)-4-(4-fluoro-phenyl)-methyl-2-(5-methyl-thiazol-2-yl)-1,4-dihydro-pyrimidine-5-carboxylic acid methyl ester | 0.47 | 85 |
| 38 | 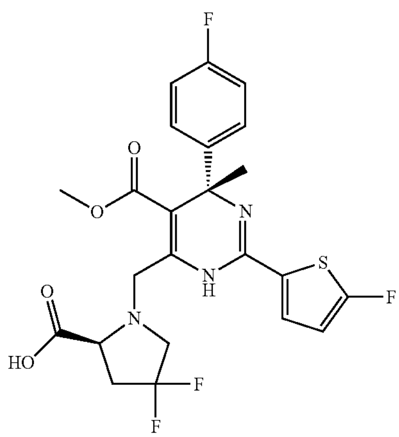 [SMILES: COC(=O)C1=C(CN2CC(F)(F)C[C@H]2C(=O)O)NC(c2ccc(F)s2)=N[C@@]1(C)c1ccc(F)cc1] | (S)-6-((S)-2-Carboxy-4,4-difluoro-pyrrolidin-1-ylmethyl)-4-(4-fluoro-phenyl)-2-(5-fluoro-thiophen-2-yl)-4-methyl-1,4-dihydro-pyrimidine-5-carboxylic acid methyl ester | 2.03 | |
| 39 | 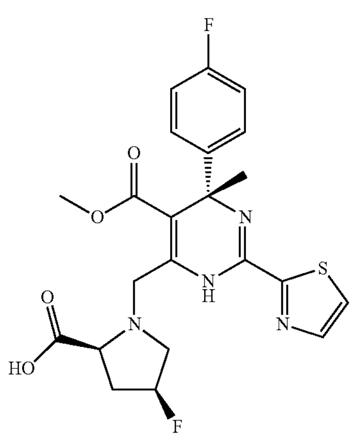 [SMILES: COC(=O)C1=C(CN2C[C@@H](F)C[C@H]2C(=O)O)NC(c2nccs2)=N[C@@]1(C)c1ccc(F)cc1] | (S)-6-((2S,4S)-2-Carboxy-4-fluoro-pyrrolidin-1-ylmethyl)-4-(4-fluoro-phenyl)-4-methyl-2-thiazol-2-yl-1,4-dihydro-pyrimidine-5-carboxylic acid methyl ester | 10.5 | 100 |

TABLE 1-continued

Structure, name and activity data of particular compounds

| Example No. | Structure | Name | HepDe19 EC50 (µM) | CC50 (µM) |
|---|---|---|---|---|
| 40 | 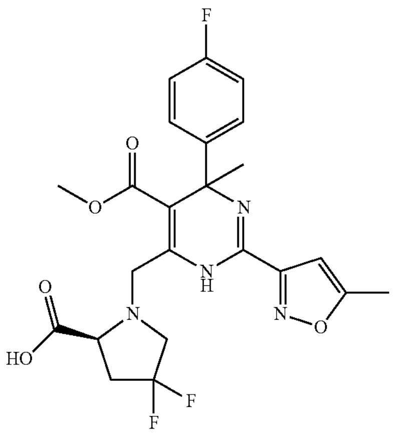 [SMILES: COC(=O)C1=C(CN2CC(F)(F)C[C@H]2C(=O)O)NC(c2cc(C)on2)=NC1(C)c1ccc(F)cc1] | 6-((S)-2-Carboxy-4,4-difluoro-pyrrolidin-1-ylmethyl)-4-(4-fluoro-phenyl)-4-methyl-2-(5-methyl-isoxazol-3-yl)-1,4-dihydro-pyrimidine-5-carboxylic acid methyl ester | 5.39 | 100 |
| 41 | 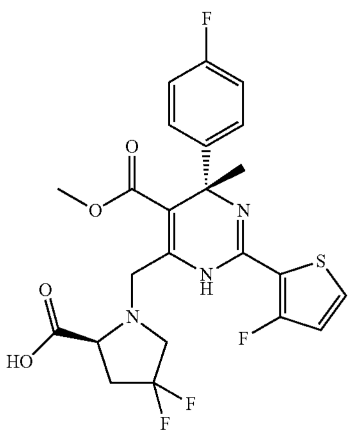 [SMILES: COC(=O)C1=C(CN2CC(F)(F)C[C@H]2C(=O)O)NC(c2sccc2F)=N[C@@]1(C)c1ccc(F)cc1] | (S)-6-((S)-2-Carboxy-4,4-difluoro-pyrrolidin-1-ylmethyl)-4-(4-fluoro-phenyl)-2-(3-fluoro-thiophen-2-yl)-4-methyl-1,4-dihydro-pyrimidine-5-carboxylic acid methyl ester | 0.285 | 100 |
| 42 | 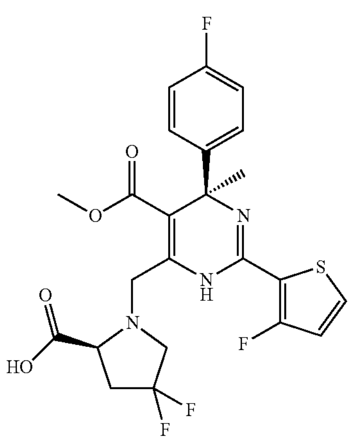 [SMILES: COC(=O)C1=C(CN2CC(F)(F)C[C@H]2C(=O)O)NC(c2sccc2F)=N[C@]1(C)c1ccc(F)cc1] | (R)-6-((S)-2-Carboxy-4,4-difluoro-pyrrolidin-1-ylmethyl)-4-(4-fluoro-phenyl)-2-(3-fluoro-thiophen-2-yl)-4-methyl-1,4-dihydro-pyrimidine-5-carboxylic acid methyl ester | 6.81 | 100 |

TABLE 1-continued

Structure, name and activity data of particular compounds

| Example No. | Structure | Name | HepDe19 EC50 (μM) | CC50 (μM) |
|---|---|---|---|---|
| 43 | 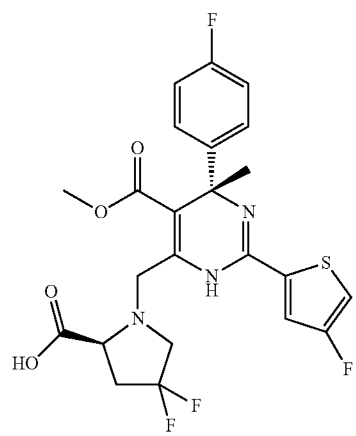 [SMILES: COC(=O)C1=C(CN2CC(F)(F)C[C@H]2C(=O)O)NC(c2cc(F)cs2)=N[C@@]1(C)c1ccc(F)cc1] | (S)-6-((S)-2-Carboxy-4,4-difluoro-pyrrolidin-1-ylmethyl)-4-(4-fluoro-phenyl)-2-(4-fluoro-thiophen-2-yl)-4-methyl-1,4-dihydro-pyrimidine-5-carboxylic acid methyl ester | 0.131 | 100 |
| 44 | 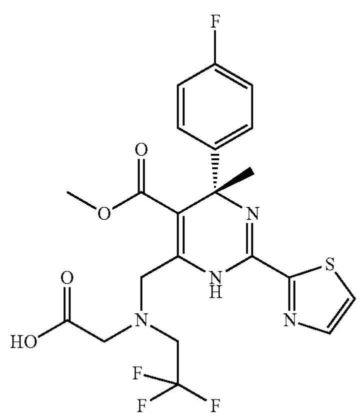 [SMILES: COC(=O)C1=C(CN(CC(=O)O)CC(F)(F)F)NC(c2nccs2)=N[C@@]1(C)c1ccc(F)cc1] | (S)-6-{[Carboxymethyl-(2,2,2-trifluoro-ethyl)-amino]-methyl}-4-(4-fluoro-phenyl)-4-methyl-2-thiazol-2-yl-1,4-dihydro-pyrimidine-5-carboxylic acid methyl ester | 21.5 | 100 |
| 45 | 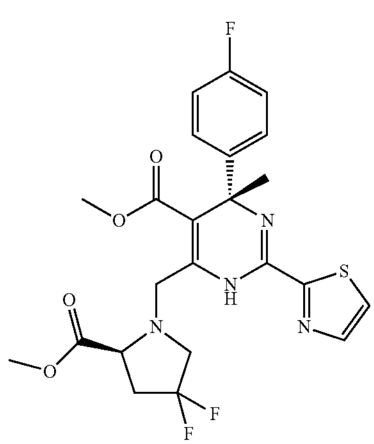 [SMILES: COC(=O)C1=C(CN2CC(F)(F)C[C@H]2C(=O)OC)NC(c2nccs2)=N[C@@]1(C)c1ccc(F)cc1] | (S)-6-((S)-4,4-Difluoro-2-methoxycarbonyl-pyrrolidin-1-ylmethyl)-4-(4-fluoro-phenyl)-4-methyl-2-thiazol-2-yl-1,4-dihydro-pyrimidine-5-carboxylic acid methyl ester | 0.783 | 100 |

TABLE 1-continued

Structure, name and activity data of particular compounds

| Example No. | Structure | Name | HepDe19 EC50 (μM) | CC50 (μM) |
|---|---|---|---|---|
| 46 | 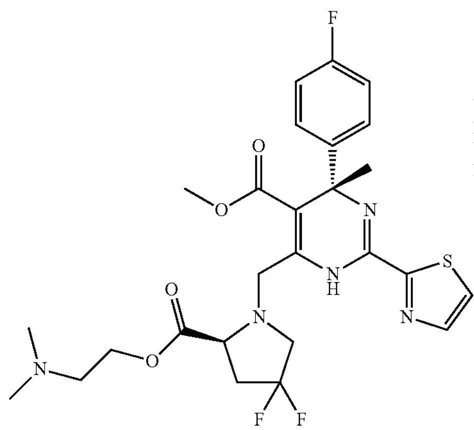 [SMILES: COC(=O)C1=C(CN2CC(F)(F)C[C@H]2C(=O)OCCN(C)C)NC(c2nccs2)=N[C@@]1(C)c1ccc(F)cc1] | (S)-6-[(S)-2-(2-Dimethylamino-ethoxycarbonyl)-4,4-difluoro-pyrrolidin-1-ylmethyl]-4-(4-fluoro-phenyl)-4-methyl-2-thiazol-2-yl-1,4-dihydro-pyrimidine-5-carboxylic acid methyl ester | 2.13 | 100 |
| 47 | 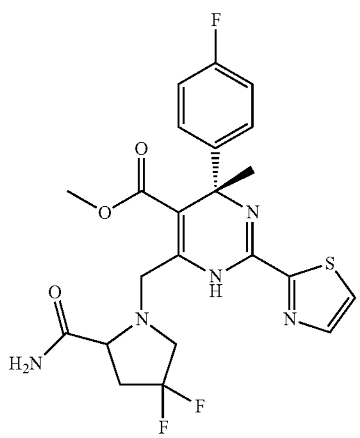 [SMILES: COC(=O)C1=C(CN2CC(F)(F)CC2C(N)=O)NC(c2nccs2)=N[C@@]1(C)c1ccc(F)cc1] | (S)-6-(2-Carbamoyl-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester | 0.048 | 100 |
| 48 | 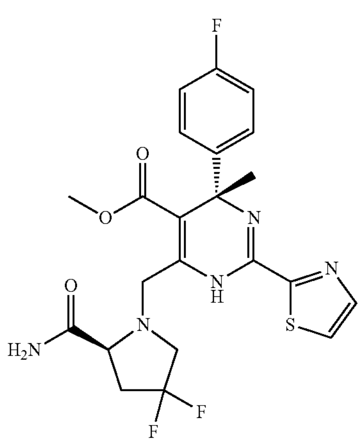 [SMILES: COC(=O)C1=C(CN2CC(F)(F)C[C@H]2C(N)=O)NC(c2nccs2)=N[C@@]1(C)c1ccc(F)cc1] | (S)-6-((S)-2-Carbamoyl-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester | 0.08 | 100 |

TABLE 1-continued

Structure, name and activity data of particular compounds

| Example No. | Structure | Name | HepDe19 EC50 (μM) | CC50 (μM) |
|---|---|---|---|---|
| 49 | 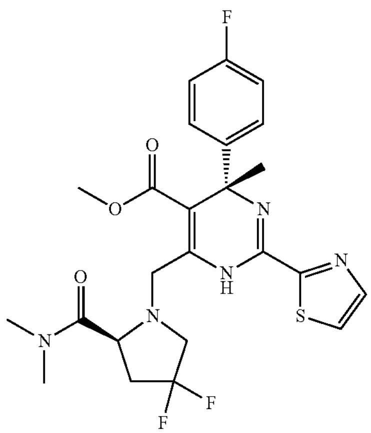 [SMILES: COC(=O)C1=C(CN2CC(F)(F)C[C@H]2C(=O)N(C)C)NC(c2nccs2)=N[C@@]1(C)c1ccc(F)cc1] | (S)-6-((S)-2-Dimethylcarbamoyl-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester | 0.29 | 100 |
| 50 | 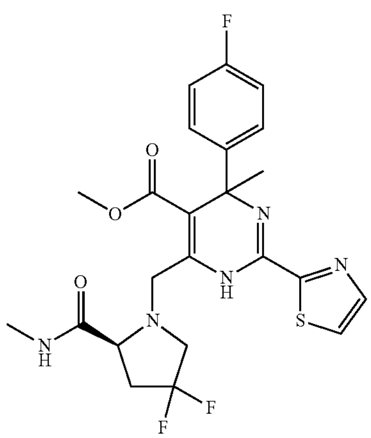 [SMILES: CNC(=O)[C@@H]1CC(F)(F)CN1CC1=C(C(=O)OC)C(C)(c2ccc(F)cc2)N=C(c2nccs2)N1] | 6-((S)-4,4-Difluoro-2-methylcarbamoyl-pyrrolidin-1-ylmethyl)-4-(4-fluoro-phenyl)-4-methyl-2-thiazol-2-yl-1,4-dihydro-pyrimidine-5-carboxylic acid methyl ester | 0.606 | 100 |
| 51 | 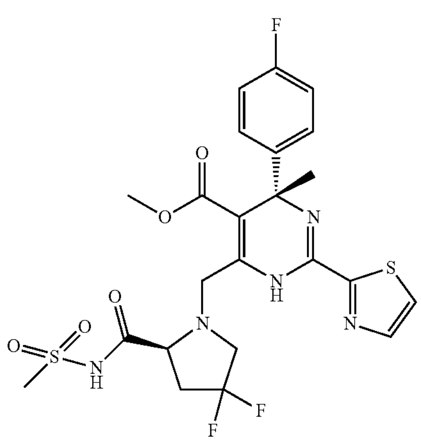 [SMILES: COC(=O)C1=C(CN2CC(F)(F)C[C@H]2C(=O)NS(C)(=O)=O)NC(c2nccs2)=N[C@@]1(C)c1ccc(F)cc1] | (S)-6-((S)-4,4-Difluoro-2-methanesulfonyl-aminocarbonyl-pyrrolidin-1-ylmethyl)-4-(4-fluoro-phenyl)-4-methyl-2-thiazol-2-yl-1,4-dihydro-pyrimidine-5-carboxylic acid methyl ester | 18.16 | 90 |

TABLE 1-continued

Structure, name and activity data of particular compounds

| Example No. | Structure | Name | HepDe19 EC50 (µM) | CC50 (µM) |
|---|---|---|---|---|
| 52 | 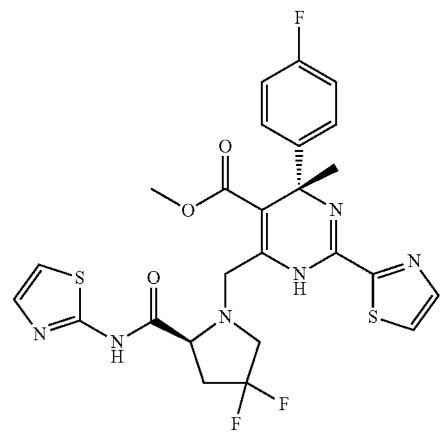 [SMILES: COC(=O)C1=C(CN2CC(F)(F)C[C@H]2C(=O)Nc2nccs2)NC(c2nccs2)=N[C@@]1(C)c1ccc(F)cc1] | (S)-6-[(S)-4,4-Difluoro-2-(thiazol-2-ylcarbamoyl)-pyrrolidin-1-ylmethyl]-4-(4-fluoro-phenyl)-4-methyl-2-thiazol-2-yl-1,4-dihydro-pyrimidine-5-carboxylic acid methyl ester | 5.426 | 4.07 |
| 53 | 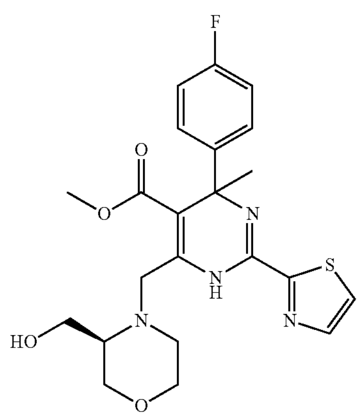 [SMILES: COC(=O)C1=C(CN2CCOC[C@H]2CO)NC(c2nccs2)=NC1(C)c1ccc(F)cc1] | 4-(4-Fluoro-phenyl)-6-((R)-3-hydroxymethyl-morpholin-4-ylmethyl)-4-methyl-2-thiazol-2-yl-1,4-dihydro-pyrimidine-5-carboxylic acid methyl ester | 1.75 | 100 |
| 54 | 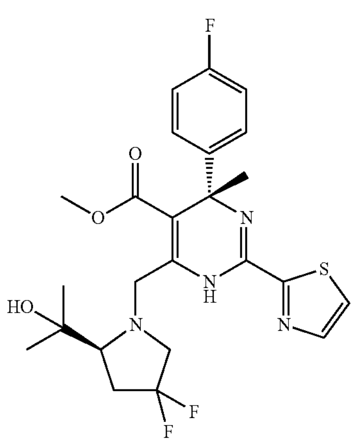 [SMILES: COC(=O)C1=C(CN2CC(F)(F)C[C@H]2C(C)(C)O)NC(c2nccs2)=N[C@@]1(C)c1ccc(F)cc1] | (S)-6-[(S)-4,4-Difluoro-2-(1-hydroxy-1-methyl-ethyl)-pyrrolidin-1-ylmethyl]-4-(4-fluoro-phenyl)-4-methyl-2-thiazol-2-yl-1,4-dihydro-pyrimidine-5-carboxylic acid methyl ester | 0.7 | 50.4 |

TABLE 1-continued

Structure, name and activity data of particular compounds

| Example No. | Structure | Name | HepDe19 EC50 (μM) | CC50 (μM) |
|---|---|---|---|---|
| 55 | 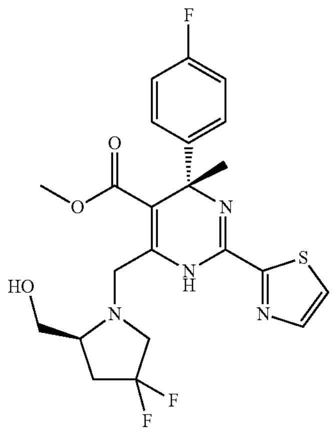 [SMILES: COC(=O)C1=C(CN2CC(F)(F)C[C@H]2CO)NC(c2nccs2)=N[C@@]1(C)c1ccc(F)cc1] | (S)-6-((S)-4,4-Difluoro-2-hydroxymethyl-pyrrolidin-1-ylmethyl)-4-(4-fluoro-phenyl)-4-methyl-2-thiazol-2-yl-1,4-dihydro-pyrimidine-5-carboxylic acid methyl ester | 0.067 | 100 |
| 56 | 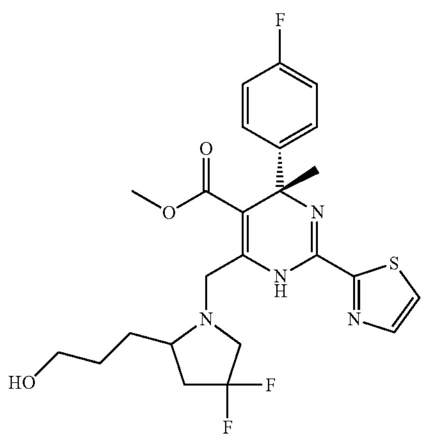 | (S)-6-[4,4-Difluoro-2-(3-hydroxy-propyl)-pyrrolidin-1-ylmethyl]-4-(4-fluoro-phenyl)-4-methyl-2-thiazol-2-yl-1,4-dihydro-pyrimidine-5-carboxylic acid methyl ester | 0.66 | 90 |
| 57 | 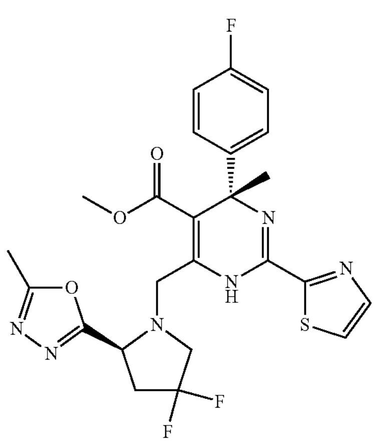 [SMILES: COC(=O)C1=C(CN2CC(F)(F)C[C@H]2c2nnc(C)o2)NC(c2nccs2)=N[C@@]1(C)c1ccc(F)cc1] | (S)-6-[(S)-4,4-Difluoro-2-(5-methyl-[1,3,4]oxadiazol-2-yl)-pyrrolidin-1-ylmethyl]-4-(4-fluoro-phenyl)-4-methyl-2-thiazol-2-yl-1,4-dihydro-pyrimidine-5-carboxylic acid methyl ester | 1.558 | 100 |

TABLE 1-continued

Structure, name and activity data of particular compounds

| Example No. | Structure | Name | HepDe19 EC50 (μM) | CC50 (μM) |
|---|---|---|---|---|
| 58 | 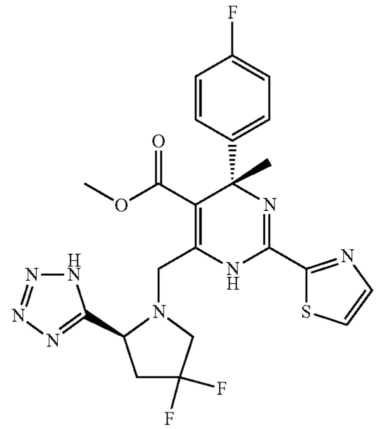 [SMILES: COC(=O)C1=C(CN2CC(F)(F)C[C@H]2c2nnn[nH]2)NC(c2nccs2)=N[C@@]1(C)c1ccc(F)cc1] | (S)-6-[(S)-4,4-Difluoro-2-(1H-tetrazol-5-yl)-pyrrolidin-1-ylmethyl]-4-(4-fluoro-phenyl)-4-methyl-2-thiazol-2-yl-1,4-dihydro-pyrimidine-5-carboxylic acid methyl ester | 1.017 | 100 |
| 59 | 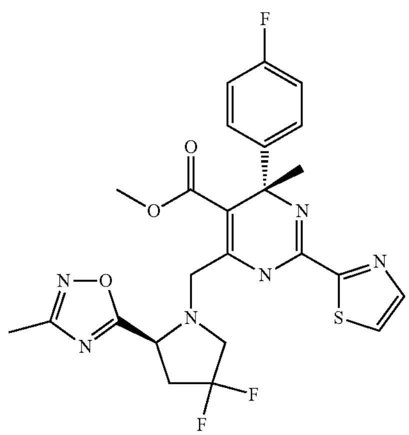 [SMILES: COC(=O)C1=C(CN2CC(F)(F)C[C@H]2c2nc(C)no2)NC(c2nccs2)=N[C@@]1(C)c1ccc(F)cc1] | (S)-6-[(S)-4,4-Difluoro-2-(3-methyl-[1,2,4]oxadiazol-5-yl)-pyrrolidin-1-ylmethyl]-4-(4-fluoro-phenyl)-4-methyl-2-thiazol-2-yl-1,4-dihydro-pyrimidine-5-carboxylic acid methyl ester | 1.238 | 65.3 |

TABLE 2

NMR and MS data of particular compounds

| Example No. | 1H NMR data | MW |
|---|---|---|
| 1 | 1H NMR (MeOD-$d_4$, 400 MHz), 7.95 (d, 1H, J = 3.2 Hz), 7.75 (d, 1H, J = 3.2 Hz), 7.49-7.45 (m, 2H), 7.04 (t, 2H, J = 8.8 Hz), 4.71-4.62 (m, 2H), 3.80 (s, 3H), 3.43 (s, 3H), 1.92 (s, 3H), 1.57 (s, 6H). | MS: calc'd 462 (MH+), exp 462 (MH+). |
| 2 | 1H NMR (MeOD-$d_4$, 400 MHz), 7.94 (d, 1H, J = 2.8 Hz), 7.93 (d, 1H, J = 2.8 Hz), 7.53-7.49 (m, 2H), 7.07-7.03 (m, 2H), 4.85-4.78 (m, 2H), 4.40-4.37 (m, 1H), 3.44 (s, 3H), 1.94 (s, 3H). | MS: calc'd 488 (MH+), exp 488 (MH+). |
| 3 | 1H NMR (MeOD-$d_4$, 400 MHz), 8.12 (d, 1H, J = 3.2 Hz), 8.06 (d, 1H, J = 3.2 Hz), 7.63-7.60 (m, 2H), 7.15 (t, 2H, J = 8.8 Hz), 4.30 (s, 2H), 3.51 (s, 3H), 2.79 (s, 3H), 2.10 (s, 3H), 1.52-1.51 (m, 2H), 1.38-1.37 (m, 2H). | MS: calc'd 459 (MH+), exp 459 (MH+). |
| 4 | 1H NMR (CD3OD, 500 MHz) δ 8.10 (d, 1H), 8.03 (d, 1H), 7.64-7.61 (m, 2H), 7.15-7.12 (m, 2H), 4.32-4.31 (m, 2H), 4.18-4.14 (m, 2H), 3.99-3.72 (m, 3H), 3.51-3.49 (m, 4H), 3.02 (m, 1H), 2.11 (d, 3H). | LC-MS: calc'd 475 (MH+), exp 475 (MH+). |
| 5 | 1H NMR (MeOD-d4, 400 MHz), 7.95 (d, 1H, J = 3.2 Hz), 7.74 (d, 1H, J = 3.2 Hz), 7.48-7.45 (m, 2H), 7.03 (t, 2H, J = 8.8 Hz), 4.05-3.87 (m, 4H), 3.78-3.71 (m, 5H), 3.49-3.45 (m, 1H), 3.42 (s, 3H), 3.14-3.07 (m, 1H), 2.52-2.42 (m, 1H), 1.99 (s, 3H). | MS: calc'd (MH+) 489 exp (MH+) 489. |

TABLE 2-continued

NMR and MS data of particular compounds

| Example No. | 1H NMR data | MW |
|---|---|---|
| 6 | 1H NMR (MeOD-d4, 400 MHz), 7.95 (d, 1H, J = 3.2 Hz), 7.74 (d, 1H, J = 3.2 Hz), 7.48-7.45 (m, 2H), 7.03 (t, 2H, J = 8.8 Hz), 4.35-4.21 (m, 2H), 4.17-4.05 (m, 2H), 3.96-3.84 (m, 2H), 3.75-3.70 (m, 1H), 3.58-3.47 (m, 4H), 2.97-2.89 (m, 1H), 1.99 (s, 3H). | MS: calc'd (MH+) 475 exp (MH+) 475. |
| 7 | 1H NMR (MeOD-d4, 400 MHz), 8.07 (d, 1H, J = 3.2 Hz), 7.97 (d, 1H, J = 3.2 Hz), 7.62-7.59 (m, 2H), 7.13 (t, 2H, J = 8.8 Hz), 4.31 (s, 2H), 4.17-4.05 (m, 2H), 3.96-3.84 (m, 3H), 3.62-3.55 (m, 1H), 3.51 (s, 3H), 3.03-2.99 (m, 1H), 2.09 (s, 3H). | MS: calc'd (MH+) 475 exp (MH+) 475. |
| 8 | 1H NMR (MeOD-d4, 400 MHz), 8.07 (d, 1H, J = 3.2 Hz), 7.97 (d, 1H, J = 3.2 Hz), 7.62-7.59 (m, 2H), 7.13 (t, 2H, J = 8.8 Hz), 4.28 (dd, 2H, J1 = 33.4 Hz, J2 = 16.4 Hz), 4.17-4.05 (m, 2H), 3.96-3.84 (m, 3H), 3.62-3.50 (m, 4H), 3.03-2.99 (m, 1H), 2.09 (s, 3H). | MS: calc'd (MH+) 475 exp (MH+) 475. |
| 9 | 1H NMR (MeOD-d4, 400 MHz), 8.60 (d, 1H, J = 2.8 Hz), 8.53-8.50 (m, 1H), 7.80-7.78 (m, 1H), 7.59-7.56 (m, 2H), 7.11-7.07 (m, 2H), 4.11-4.01 (m, 3H), 3.99-3.97 (m, 1H), 3.88-3.84 (m, 1H), 3.82-3.80 (m, 1H), 3.59-3.56 (m, 1H), 3.49 (s, 3H), 3.44-3.38 (m, 1H), 2.89-2.80 (m, 1H), 2.05 (s, 3H). | MS: calc'd (MH+) 487 exp (MH+) 487. |
| 10 | 1H NMR (MeOD-d4, 400 MHz), 8.60 (d, 1H, J = 2.8 Hz), 8.55-8.53 (m, 1H), 7.83-7.79 (m, 1H), 7.60-7.57 (m, 2H), 7.13-7.08 (m, 2H), 4.17-4.08 (m, 3H), 4.01-3.97 (m, 1H), 3.91-3.84 (m, 1H), 3.82-3.80 (m, 1H), 3.60-3.58 (m, 1H), 3.50 (s, 3H), 3.44-3.38 (m, 1H), 2.89-2.80 (m, 1H), 2.06 (s, 3H). | MS: calc'd (MH+) 487 exp (MH+) 487. |
| 11 | 1H NMR (CD3OD, 500 MHz) δ 8.15-8.15 (m, 2H), 7.67-7.62 (m, 2H), 7.19-7.14 (m, 2H), 4.16-3.90 (m, 3H), 3.65-3.61 (m, 1H), 3.51 (d, 3H), 3.25-3.20 (m, 1H), 2.86-2.82 (m, 1H), 2.63-2.61 (m, 1H), 2.15 (d, 3H). | LC-MS: calc'd 495 (MH+), exp 495 (MH+). |
| 12 | 1H NMR (CD3OD, 500 MHz) δ 7.96 (s, 1H), 7.77 (s, 1H), 7.52 (d, 2H), 7.06 (d, 2H), 4.00-3.95 (m, 3H), 3.63-3.61 (m, 1H), 3.46 (s, 3H), 3.20-3.18 (m, 1H), 2.79 (m, 1H), 2.67 (m, 1H), 1.95 (s, 3H). | LC-MS: calc'd 495 (MH+), exp 495 (MH+). |
| 13 | 1H NMR (MeOD-d4, 400 MHz), 8.21 (s, 2H), 7.67-7.65 (m, 2H), 7.21-7.17 (m, 2H,), 4.16 (d, 1H, J = 15.6 Hz), 4.02 (t, 1H, J = 8.0 Hz), 3.93 (d, 1H, J = 15.6 Hz), 3.72-3.61 (m, 1H), 3.53 (s, 3H), 3.29-3.19 (m, 1H), 2.91-2.78 (m, 1H), 2.59-2.55 (m, 1H), 2.17 (s, 3H). | MS: calc'd (MH+) 495 exp (MH+) 495. |
| 14 | 1H NMR (MeOD-d4, 400 MHz), 8.11 (d, 1H, J = 3.2 Hz), 8.04 (d, 1H, J = 3.2 Hz), 7.55-7.49 (m, 1H), 7.40-7.38 (m, 1H), 7.34-7.29 (m, 1H,), 4.15 (d, 1H, J = 15.6 Hz), 4.02-3.98(m, 2H), 3.74-3.61 (m, 1H), 3.53 (s, 3H), 3.30-3.23 (m, 1H), 2.91-2.78 (m, 1H), 2.65-2.49 (m, 1H), 2.08 (s, 3H). | MS: calc'd (MH+) 513.1, exp (MH+) 513.1 |
| 15 | 1H NMR (MeOD-d4, 400 MHz), 8.17 (d, 1H, J = 3.2 Hz), 8.10 (d, 1H, J = 3.2 Hz), 7.62-7.53 (m, 1H), 7.45-7.39 (m, 1H), 7.37-7.25 (m, 1H,), 4.25-4.18 (m, 2H), 4.10-4.06(m, 2H), 3.96-3.94 (m, 1H), 3.89-3.86 (m, 2H), 3.84 (s, 3H), 3.55 (s, 3H), 3.50-3.40 (m, 1H), 2.90-2.87 (m, 1H), 2.08 (s, 3H). | MS: calc'd (MH+) 507, exp (MH+) 507. |
| 16 | 1H NMR (MeOD-d4, 400 MHz), 8.06 (d, 1H, J = 3.2 Hz), 7.95 (d, 1H, J = 3.2 Hz), 7.53-7.51 (m, 1H), 7.40-7.37 (m, 1H), 7.31-7.25 (m, 1H,), 4.39-4.28 (m, 2H), 4.15-4.12 (m, 2H), 3.58-3.50 (m, 4H), 3.05-3.01 (m, 1H), 2.05 (s, 3H). | MS: calc'd (MH+) 493 exp (MH+) 493. |
| 17 | 1H NMR (MeOD-d4, 400 MHz), 8.80 (d, 1H, J = 2.8 Hz), 8.43-8.40 (m, 1H), 8.01-7.98 (m, 1H), 7.70-7.66 (m, 2H), 7.24-7.18 (m, 2H), 4.16-3.94 (m, 3H), 3.84-3.83 (m, 3H), 3.61-3.55 (m, 4H), 3.22-3.18 (m, 1H), 2.91-2.78 (m, 1H), 3.61-3.48 (m, 1H), 2.24-2.21 (m, 3H). | MS: calc'd (MH+) 521 exp (MH+) 521 |
| 18 | 1H NMR (MeOD-d4, 400 MHz), 8.77 (d, 1H, J = 2.8 Hz), 8.46-8.42 (m, 1H), 8.00-7.95 (m, 1H), 7.70-7.66 (m, 2H), 7.23-7.19 (m, 2H), 4.16 (d, 1H, J = 16 Hz), 3.98 (t, 1H, J = 8.8 Hz), 3.88 (d, 1H, J = 16 Hz), 3.60-3.56 (m, 4H), 3.28-3.15 (m, 1H), 2.93-1.79 (m, 1H), 2.58-44 (m, 1H), 2.21 (s, 3H). | MS: calc'd (MH+) 507 exp (MH+) 507. |
| 19 | $^1$H NMR (400 MHz, MeOH-d4) 7.87 (s, 1 H), 7.47-7.51 (m, 2 H), 7.01-7.06 (m, 2 H), 3.92-4.30 (m, 2 H), 3.49 (s, 3 H), 3.40 (m, 2H), 2.35-2.90 (m, 3 H), 2.36 (s, 3H), 1.85 (s, 3 H). | MS: calc'd (MH+) 509 exp (MH+) 509. |

TABLE 2-continued

NMR and MS data of particular compounds

| Example No. | 1H NMR data | MW |
|---|---|---|
| 20 | $^1$H NMR (400 MHz, MeOH-d4) 8.02-8.18 (m, 2 H), 7.54-7.65 (m, 2 H), 7.08-7.20 (m, 2 H), 3.88-4.14 (m, 2 H), 3.49 (s, 3 H), 2.75-2.90 (m, 2 H), 2.41-2.57 (m, 2 H), 2.09 (s, 3 H), 1.56 (s, 3 H). | MS: calc'd (MH+) 509 exp (MH+) 509. |
| 21 | 1H NMR (MeOD-d4, 400 MHz), 7.98 (d, 1H, J = 3.2 Hz), 7.81 (d, 1H, J = 3.2 Hz), 7.57-7.53 (m, 2H), 7.14 (t, 2H, J = 8.8 Hz), 3.92-3.74 (m, 3H), 3.49-3.41 (m, 1H), 3.18-3.08 (m, 1H), 2.81-2.69 (m, 1H), 2.55-2.49 (m, 1H), 1.89 (s, 3H). | MS: calc'd (M++H) 462, exp (M++H) 462. |
| 22 | 1H NMR (MeOD-d4, 400 MHz), 8.03 (d, 1H, J = 3.2 Hz), 7.88 (d, 1H, J = 3.2 Hz), 7.45-7.42 (m, 1H), 7.36-7.30 (m, 2H), 4.16-4.01(m, 4H), 3.96-3.82 (m, 3H), 3.43-3.37 (m, 1H), 2.93-2.86 (m, 1H), 1.92 (s, 3H). | MS: calc'd (MH+) 460 exp (MH+) 460. |
| 23 | 1H NMR (MeOD-d4, 400 MHz), 7.98 (d, 1H, J = 3.2 Hz), 7.81 (d, 1H, J = 3.2 Hz), 7.44-7.39 (m, 1H), 7.35-7.27 (m, 2H), 3.92-3.74 (m, 3H), 3.49-3.41 (m, 1H), 3.18-3.08 (m, 1H), 2.81-2.69 (m, 1H), 2.52-2.46 (m, 1H), 1.86 (s, 3H). | MS: calc'd (MH+) 480 exp (MH+) 480. |
| 24 | $^1$H NMR (MeOD-d$_4$, 400 MHz), 7.95 (d, J = 3.01 Hz, 1 H), 7.73 (d, J = 3.26 Hz, 1 H), 7.37 (ddd, J = 12.17, 7.78, 1.88 Hz, 1 H), 7.28 (br. s., 1 H), 7.17-7.26 (m, 1 H), 3.85-4.06 (m, 4 H) 3.69 (t, J = 8.16 Hz, 1 H) 3.48-3.61 (m, 1 H) 2.99-3.18 (m, 1 H) 2.61-2.78 (m, 1 H) 2.39-2.58 (m, 1 H) 1.89 (s, 3 H)1.04 (t, J = 7.03 Hz, 3 H). | MS: calc'd (MH+) 527 exp (MH+) 527. |
| 25 | $^1$H NMR (MeOD-d$_4$, 400 MHz), 8.25 (s, 2 H), 7.58-7.75 (m, 2 H), 7.19 (t, J = 8.66 Hz, 2 H), 3.93-4.19 (m, 2 H), 3.75 (d, J = 1.25 Hz, 1 H), 3.53 (s, 3 H), 3.35-3.46 (m, 1 H), 2.88-3.10 (m, 1 H), 1.85-2.41 (m, 7 H). | MS: calc'd (MH+) 509 exp (MH+) 509. |
| 26 | $^1$H NMR (MeOD-d$_4$, 400 MHz), 7.97 (d, J = 3.01 Hz, 1 H), 7.72 (d, J = 3.01 Hz, 1 H), 7.49 (dd, J = 8.66, 5.40 Hz, 2 H), 7.04 (t, J = 8.78 Hz, 2 H), 3.72-3.87 (m, 2 H), 3.44 (s, 3 H), 3.25-3.31 (m, 1 H), 3.14 (d, J = 12.05 Hz, 1 H), 2.47-2.60 (m, 1 H), 1.97-2.41 (m, 4 H), 1.89 (s, 3 H). | MS: calc'd (MH+) 509 exp (MH+) 509. |
| 27 | $^1$H NMR (MeOD-d$_4$, 400 MHz), 7.53 (dd, J = 8.66, 5.40 Hz, 2 H), 7.19 (s, 1 H), 6.98-7.11 (m, 3 H), 3.77-3.96 (m, 5 H), 3.51-3.65 (m, 2 H), 3.46(s, 3 H), 3.01 (td, J = 15.12, 11.42 Hz, 1 H), 2.64 (qd, J = 12.84, 8.16 Hz, 1 H), 2.32-2.50 (m, 1 H), 1.84-2.00 (m, 3 H). | MS: calc'd (MH+) 492 exp (MH+) 492. |
| 28 | $^1$H NMR (MeOD-d$_4$, 400 MHz), 7.95 (d, J = 3.01 Hz, 1 H), 7.72 (d, J = 3.26 Hz, 1 H), 7.36 (ddd, J = 12.30, 7.78, 2.26 Hz, 1 H), 7.27 (br. s., 1 H), 7.21(dd, J = 10.29, 8.28 Hz, 1 H), 3.80-4.02 (m, 4 H), 3.44-3.58 (m, 2 H), 2.87 (td, J = 15.56, 11.04 Hz, 1 H), 2.54-2.73 (m, 1 H), 2.35-2.52 (m, 1 H), 1.89 (s, 3 H), 1.03 (t, J = 7.03 Hz, 3 H). | MS: calc'd (MH+) 527 exp (MH+) 527. |
| 29 | $^1$H NMR (MeOD-d$_4$, 400 MHz), 8.10 (d, J = 2.76 Hz, 1 H), 7.99-8.06 (m, 1 H), 7.52-7.63 (m, 1 H), 7.44 (d, J = 7.03 Hz, 1 H), 7.22-7.38 (m, 1 H), 5.36 (t, J = 4.64 Hz, 1 H), 4.30-4.54 (m, 2 H), 4.09-4.22 (m, 3 H), 3.86-4.06 (m, 4 H), 3.55-3.73 (m, 1 H), 1.98-2.15 (m, 3 H), 0.92 (t, J = 6.78 Hz, 3 H). | MS: calc'd (MH+) 507 exp (MH+) 507. |
| 30 | $^1$H NMR (MeOD-d$_4$, 400 MHz), 7.52 (dd, J = 8.66, 5.40 Hz, 2 H), 7.21 (s, 1 H), 6.98-7.11 (m, 3 H), 3.72-4.06 (m, 10 H) 3.48 (s, 3 H), 3.12-3.23 (m, 1 H), 2.61 (ddd, J = 11.54, 8.16, 3.14 Hz, 1 H), 1.93 (s, 3 H). | MS: calc'd (MH+) 472 exp (MH+) 472. |
| 31 | $^1$H NMR (CDCl$_3$, 400 MHz), 7.47-7.59 (m, 2 H), 7.18 (s, 1 H), 7.01-7.12 (m, 2 H), 4.12 (d, J = 14.56 Hz, 1 H), 3.98 (dd, J = 9.79, 6.02 Hz, 1 H), 3.61 (d, J = 14.31 Hz, 1 H), 3.53 (d, J = 10.54 Hz, 1 H), 3.47 (s, 3 H), 3.12 (br. s., 1 H), 2.71-2.90 (m, 1 H), 2.50-2.67 (m, 1 H), 2.46 (s, 3 H), 1.98-2.07 (m, 3 H). | MS: calc'd (MH+) 509 exp (MH+) 509. |
| 32 | $^1$H NMR (CDCl$_3$, 400 MHz), 7.49-7.61 (m, 2 H), 7.17 (s, 1 H), 7.05-7.13 (m, 2 H), 4.14 (d, J = 14.31 Hz, 1 H), 3.92 (dd, J = 9.66, 6.15 Hz, 1 H), 3.49-3.58 (m, 2 H), 3.47 (s, 3 H), 3.18-3.33 (m, 1 H), 2.81 (dd, J = 14.68, 9.66 Hz, 1 H), 2.57 (dd, J = 12.30, 6.02 Hz, 1 H), 2.46 (s, 3 H), 2.01 (s, 3 H). | MS: calc'd (MH+) 509 exp (MH+) 509. |
| 33 | $^1$H NMR (CDCl$_3$, 400 MHz), 7.71 (s, 1 H), 7.41-7.58 (m, 2 H), 7.00-7.17 (m, 2 H), 4.12-4.21 (m, 1 H), 3.93-4.03 (m, 1 H), 3.70-3.78 (m, 1 H), 3.54 (s, 4 H), 3.15-3.30 (m, 1 H), 2.75-2.90 (m, 1 H), 2.52-2.69 (m, 1 H), 2.15 (s, 3 H). | MS: calc'd (MH+) 529 exp (MH+) 529. |

TABLE 2-continued

NMR and MS data of particular compounds

| Example No. | 1H NMR data | MW |
|---|---|---|
| 34 | ¹H NMR (MeOD-d₄, 400 MHz), 7.93-8.01 (m, 1 H), 7.79-7.89 (m, 1 H), 7.55-7.67 (m, 2 H), 7.06-7.17 (m, 2 H), 5.45-5.58 (m, 1 H), 5.31-5.45 (m, 1 H), 3.81-4.12 (m, 2 H), 3.48 (s, 3 H), 2.70-2.94 (m, 2 H), 2.31-2.55 (m, 2 H), 1.96-2.10 (m, 3 H). | MS: calc'd (MH+) 477 exp (MH+) 477. |
| 35 | ¹H NMR (MeOD-d₄, 400 MHz), 8.80-8.87 (m, 1 H), 7.48-7.59 (m, 2 H), 7.10 (s, 3 H), 3.77-4.10 (m, 3 H), 3.48-3.62 (m, 1 H), 3.46 (d, J = 4.27 Hz, 3 H), 3.00-3.23 (m, 1 H), 2.70-2.87 (m, 1 H), 2.42-2.64 (m, 1 H), 1.98 (d, J = 3.51 Hz, 3 H). | MS: calc'd (MH+) 479 exp (MH+) 479. |
| 36 | ¹H NMR (MeOD-d₄, 400 MHz), 8.14-8.17 (m, 1 H), 8.10-8.13 (m, 1 H), 7.58-7.65 (m, 2 H), 7.11-7.19 (m, 2 H), 3.99-4.06 (m, 2 H), 3.52 (s, 4 H), 3.35-3.38 (m, 1 H), 2.75-2.89 (m, 1 H), 2.41-2.56 (m, 1 H), 2.12 (s, 3 H), 1.56 (s, 3 H). | MS: calc'd (MH+) 509 exp (MH+) 509. |
| 37 | ¹H NMR (MeOD-d₄, 400 MHz), 7.62 (s, 1H), 7.50 (dd, J = 5.40, 8.66 Hz, 2H), 7.05 (t, J = 8.78 Hz, 2H), 3.90 (d, J = 5.77 Hz, 2H), 3.65 (t, J = 8.28 Hz, 1H), 3.39-3.58 (m, 7H), 3.05 (d, J = 11.54 Hz, 1H), 2.68 (dd, J = 7.91, 13.18 Hz, 1H), 2.48-2.58 (m, 4H). | MS: calc'd (MH+) 509 exp (MH+)509. |
| 38 | ¹H NMR (MeOD-d₄, 400 MHz), 7.62 (t, J = 3.9 Hz, 1 H), 7.46 (dd, J = 8.7, 5.4 Hz, 2 H), 7.02 (t, J = 8.8 Hz, 2 H), 6.59 (dd, J = 4.3, 1.8 Hz, 1 H), 3.86 (d, J = 14.3 Hz, 2 H), 3.75 (t, J = 6.5 Hz, 1 H), 3.41-3.62 (m, 6 H), 3.06 (q, J = 7.3 Hz, 2 H), 2.61 (dd, J = 16.1, 7.5 Hz, 1 H), 2.26-2.45 (m, 1 H). | MS: calc'd (MH+)512 exp (MH+) 512. |
| 39 | ¹H NMR (MeOD-d₄, 400 MHz), 7.96 (d, J = 3.0 Hz, 1 H), 7.85 (d, J = 3.3 Hz, 1 H), 7.65 (dd, J = 8.8, 5.3 Hz, 2 H), 7.13 (t, J = 8.8 Hz, 2 H), 5.29-5.52 (m, 1 H), 4.62 (d, J = 14.1 Hz, 1 H), 4.39 (d, J = 9.5 Hz, 1 H), 4.08-4.27 (m, 2 H), 3.44-3.69 (m, 5 H), 2.54-2.97 (m, 3 H). | MS: calc'd (MH+)477 exp (MH+) 477. |
| 40 | ¹H NMR (MeOD-d₄, 400 MHz), 7.51 (dd, J = 8.2, 5.4 Hz, 2 H), 7.06 (q, J = 8.8 Hz, 2 H), 6.61 (d, J = 4.0 Hz, 1 H), 3.72-3.96 (m, 2 H), 3.40-3.63 (m, 6 H), 2.82-3.12 (m, 2 H), 2.57-2.76 (m, 1 H), 2.35-2.52 ppm (m, 5 H). | MS: calc'd (MH+) 493 exp (MH+) 493. |
| 41 | ¹H NMR (CDCl₃, 400 MHz), 7.53 (m, 2H), 7.43 (m, 1H), 7.08 (m, 2H), 6.85 (d, 1H, J = 5.6 Hz), 4.08 (d, 1H, J = 14.2 Hz), 3.86 (1H, m), 3.57 (d, 1H, J = 14.2 Hz), 3.50 (1H, m), 3.45 (3H, s), 3.20 (1H, m), 2.77 (1H, m), 2.54 (1H, m), 1.97 (3H, s). | MS: calc'd (MH+) 512 exp (MH+) 512. |
| 42 | ¹H NMR (CDCl₃, 400 MHz), 7.52 (m, 2H), 7.42 (m, 1H), 7.06 (m, 2H), 6.84 (d, 1H, J = 5.6 Hz), 4.05 (d, 1H, J = 14.2 Hz), 3.91 (m, 1H), 3.64 (d, 1H, J = 14.2 Hz), 3.47 (m, 1H), 3.45 (3H, s), 3.10 (m, 1H), 2.78 (m, 1H), 2.55 (m, 1H), 1.98 (s, 3H). | MS: calc'd (MH+) 512 exp (MH+) 512. |
| 43 | ¹H NMR (CDCl₃, 400 MHz), 7.70 (s, 1H), 7.45 (m, 2H), 7.00 (m, 3H), 4.07 (d, 1H, J = 15.0 Hz), 3.72 (m, 1H), 3.55 (s, 3H), 3.54-3.34 (m, 2H), 3.07 (m, 1H), 2.68 (m, 1H), 2.32 (m, 1H), 2.01 (s, 3H). | MS: calc'd (MH+) 512 exp (MH+) 512. |
| 44 | ¹H NMR (MeOD-d₄, 400 MHz), 7.95 (d, J = 3.26 Hz, 1 H), 7.75 (d, J = 3.26 Hz, 1 H), 7.44-7.54 (m, 2 H), 7.05 (t, J = 8.78 Hz, 2 H), 3.90-4.09 (m, 2H), 3.63 (s, 2 H), 3.45 (s, 3 H), 1.91 (s, 3 H). | MS: calc'd (MH+) 501 exp (MH+) 501. |
| 45 | ¹H NMR (MeOD-d₄, 400 MHz), 8.23 (d, J = 0.75 Hz, 2 H), 7.61-7.70 (m, 2 H), 7.19 (t, J = 8.66 Hz, 2 H), 4.06-4.16 (m, 1 H), 4.02 (t, J = 8.03 Hz, 1H), 3.92 (d, J = 15.81 Hz, 1 H), 3.82 (s, 3 H), 3.59 (d, J = 10.79 Hz, 1 H), 3.53 (s, 3 H), 3.12-3.28 (m, 1 H), 2.72-2.89 (m, 1 H), 2.43-2.61 (m, 1 H), 2.16 (s, 3 H). | MS: calc'd (MH+) 509 exp (MH+) 509. |
| 46 | ¹H NMR (MeOD-d₄, 400 MHz), 7.94 (d, J = 3.01 Hz, 1 H), 7.74 (d, J = 3.01 Hz, 1 H), 7.49 (br. s., 2 H), 7.05 (t, J = 8.78 Hz, 2 H), 4.33 (t, J = 5.65 Hz, 2 H), 3.94 (s, 3 H), 3.42-3.56 (m, 5 H), 2.66-2.82 (m, 4 H), 2.33 (s, 6 H), 1.90 (s, 3 H). | MS: calc'd (MH+) 566 exp (MH+) 566. |
| 47 | ¹H NMR (MeOD-d₄, 400 MHz), 7.95 (br. s., 1 H) 7.69-7.84 (m, 1 H) 7.61 (dd, J = 8.28, 5.52 Hz, 1 H) 7.48 (dd, J = 8.03, 5.52 Hz, 1 H) 6.99-7.17(m, 2 H) 3.39-3.88 (m, 6 H) 2.91-3.30 (m, 2 H) 2.62-2.86 (m, 1 H) 2.22-2.53 (m, 1 H) 1.81-2.02 (m, 3 H). | MS: calc'd (MH+) 494 exp (MH+) 494. |

TABLE 2-continued

NMR and MS data of particular compounds

| Example No. | 1H NMR data | MW |
|---|---|---|
| 48 | ¹H NMR(MeOD-d₄, 400 MHz), 8.13-8.00 (m, 1 H) 7.98-7.82 (m, 1 H) 7.59 (br. s., 2 H) 7.13 (s, 2 H) 3.96-3.82 (m, 1 H) 3.80-3.64 (m, 2 H) 3.62-3.44 (m, 4 H) 3.24-3.07 (m, 1 H) 2.84-2.66 (m, 1 H) 2.49-2.26 (m, 1 H) 2.02 (s, 3 H). | MS: calc'd (MH+) 494 exp (MH+) 494.1. |
| 49 | ¹H NMR(MeOD-d₄, 400 MHz), 8.10-7.98 (m, 1 H) 7.94-7.76 (m, 1 H) 7.62-7.43 (m, 2 H) 7.10 (s, 2 H) 4.27 (s, 1 H) 3.95 (s, 1 H) 3.76-3.53 (m, 2 H) 3.47 (s, 3 H) 3.09 (s, 4 H) 3.00 (s, 3 H) 2.91-2.75 (m, 1 H) 2.43-2.21 (m, 1 H) 1.97 (s, 3 H). | MS: calc'd (MH+) 522 exp (MH+) 522.0. |
| 50 | ¹H NMR(MeOD-d₄, 400 MHz), 8.05-7.89 (m, 1 H) 7.87-7.69 (m, 1 H) 7.66-7.33 (m, 2 H) 7.07 (br. s., 2 H) 3.92-3.59 (m, 3 H) 3.57-3.39 (m, 4 H) 3.27-2.95 (m, 1 H) 2.90-2.58 (m, 4 H) 2.39-2.23 (m, 1 H) 2.02-1.77 (m, 3 H). | MS: calc'd (MH+) 508 exp (MH+) 508.2. |
| 51 | ¹H NMR(MeOD-d₄, 400 MHz), 8.14-8.03 (m, 1 H) 8.00-7.91(m, 1 H) 7.65-7.51 (m, 2 H) 7.11 (s, 2 H) 4.03-3.81 (m, 3 H) 3.63 (d, J = 11.04 Hz, 1 H) 3.50 (s, 3 H) 3.28-3.10 (m, 1 H) 291-2.73 (m, 1 H) 2.68 (s, 3 H) 2.49 (qd, J = 14.01, 7.15 Hz, 1 H) 2.06 (s, 3 H). | MS: calc'd (MH+) 572 exp (MH+) 572.2. |
| 52 | ¹H NMR(MeOD-d₄, 400 MHz), 8.00-7.84 (m, 1 H) 7.82-7.62 (m, 1 H) 7.60-7.29(m, 3 H) 7.13 (br. s., 1 H) 7.03 (br. s., 2 H) 4.10-3.76 (m, 3 H) 3.72-3.55 (m, 1 H) 3.45 (s, 3 H) 3.25-3.08 (m, 1 H) 2.95-2.73 (m, 1 H) 2.63-2.35 (m, 1 H) 1.97-1.64 (m, 3 H). | MS: calc'd (MH+) 577 exp (MH+) 577.3. |
| 53 | ¹H NMR (MeOD-d₄, 400 MHz), 7.86-8.06 (m, 2 H) 7.63 (dd, J = 8.53, 5.27 Hz, 2 H) 7.13 (t, J = 8.16 Hz, 2 H) 4.41-4.73 (m, 2 H) 4.02-4.24 (m, 2 H) 3.87-3.98 (m, 3 H) 3.72-3.65 (m, 2 H) 3.35-3.55 (m, 5 H) 2.09 (d, J = 4.52 Hz, 3 H). | MS: calc'd (MH+) 461 exp (MH+) 461. |
| 54 | ¹H NMR (CDCl₃, 400 MHz), 7.81-7.91 (m, 1 H), 7.38-7.66 (m, 3 H), 7.03 (br. s., 2 H), 4.10-4.28 (m, 1 H), 3.88-4.09 (m, 1 H), 3.45-3.59 (m, 3 H), 3.29-3.45 (m, 1 H), 3.23 (t, J = 8.41 Hz, 1 H), 2.87-3.09 (m, 1 H), 2.41 (dd, J = 14.31, 7.28 Hz, 1 H), 2.19 (s, 1 H), 1.86-2.00 (m, 3 H), 1.18-1.33 (m, 6 H). | MS: calc'd (MH+) 509 exp (MH+) 509. |
| 55 | ¹H NMR (CDCl₃, 400 MHz), 7.86 (d, 1H, J = 3.1 Hz), 7.52 (m, 3H), 7.02 (m, 2H), 4.04 (m, 1H), 3.79 (m, 2H), 3.52 (s, 3H), 3.52 (m, 2H), 3.16 (m, 1H), 3.00 (m, 1H), 2.40 (m, 1H), 1.98 (s, 3H). | MS: calc'd (MH+) 481 exp (MH+) 481. |
| 56 | ¹H NMR (MeOD-d₄, 400 MHz), 7.95 (d, J = 4.0 Hz, 1H), 7.75 (d, J = 4.0 Hz, 1H), 7.51-7.47 (m, 2H), 7.05 (t, J = 8.0 Hz, 2H), 3.96 (d, J = 16 Hz, 1H), 3.74 (d, J = 16 Hz, 1H), 3.58 (t, J = 6.0 Hz, 2H), 3.50-3.40 (m, 1H), 3.48 (s, 3H), 2.98-2.85 (m, 2H), 2.57-2.45 (m, 1H), 2.13-2.05 (m, 1H), 1.92-1.85 (m, 1H), 1.90 (s, 3H), 1.63-1.49 (m, 3H). | MS: calc'd (MH+) 509 exp (MH+) 509. |
| 57 | ¹H NMR(MeOD-d₄, 400 MHz), 7.97 (br. s., 1 H) 7.83-7.68 (m, 1 H) 7.44 (br. s., 2 H) 7.03 (br. s., 2 H) 4.55-4.37 (m, 1 H) 3.97 (d, J = 3.26 Hz, 2 H) 3.67-3.53 (m, 1 H) 3.45 (s, 3 H) 3.27-3.13(m, 1 H) 2.96-2.66 (m, 2 H) 2.36 (s, 3 H) 1.84 (s, 3 H). | MS: calc'd (MH+) 533 exp (MH+) 533.2. |
| 58 | ¹H NMR(MeOD-d₄, 400 MHz), 8.02-7.92 (m, 1 H) 7.77 (d, J = 3.01 Hz, 1 H) 7.48 (dd, J = 8.53, 5.27 Hz, 2 H) 7.05 (t, J = 8.66 Hz, 2 H) 4.50 (t, J = 8.28 Hz, 1 H) 3.72-3.57(m, 2 H) 3.41 (s, 3 H) 3.24-3.08 (m, 2 H) 2.80 (td, J = 15.75, 7.15 Hz, 2 H) 1.85 (s, 3 H). | MS: calc'd (MH+) 519 exp (MH+) 519.1. |
| 59 | ¹H NMR(MeOD-d₄, 400 MHz), 7.95 (d, J = 3.01 Hz, 1 H) 7.74 (d, J = 3.26 Hz, 1 H) 7.47 (dd, J = 8.66, 5.40 Hz, 2 H) 7.04 (t, J = 8.78 Hz, 2 H) 4.53 (t, J = 7.91 Hz, 1 H) 3.95 (d, J = 8.53 Hz, 2 H) 3.60 (d, J = 10.79 Hz, 1 H) 3.50-3.39 (m, 3 H) 3.26 (br. s., 1 H) 2.99-2.85(m, 1 H) 2.78-2.64 (m, 1 H) 2.35 (s, 3 H) 1.90-1.81 (m, 3 H). | MS: calc'd (MH+) 533 exp (MH+) 533.2. |

More particular compounds of formula I include the following:

4-[6-(4-fluoro-phenyl)-5-methoxycarbonyl-6-methyl-2-thiazol-2-yl-3,6-dihydro-pyrimidin-4-ylmethyl]-morpholine-3-carboxylic acid;
4-[6-(4-fluoro-phenyl)-5-methoxycarbonyl-6-methyl-2-thiazol-2-yl-3,6-dihydro-pyrimidin-4-ylmethyl]-morpholine-(S)-3-carboxylic acid;
(S)-4-[6-(4-fluoro-phenyl)-5-methoxycarbonyl-6-methyl-2-thiazol-2-yl-3,6-dihydro-pyrimidin-4-ylmethyl]-morpholine-(S)-3-carboxylic acid;
(S)-4-[6-(4-fluoro-phenyl)-5-methoxycarbonyl-6-methyl-2-thiazol-2-yl-3,6-dihydro-pyrimidin-4-ylmethyl]-morpholine-(R)-3-carboxylic acid;
4-[6-(4-fluoro-phenyl)-2-(5-fluoro-pyridin-2-yl)-5-methoxycarbonyl-6-methyl-3,6-dihydro-pyrimidin-4-ylmethyl]-morpholine-(R)-3-carboxylic acid;
4-[6-(4-fluoro-phenyl)-2-(5-fluoro-pyridin-2-yl)-5-methoxycarbonyl-6-methyl-3,6-dihydro-pyrimidin-4-ylmethyl]-morpholine-(S)-3-carboxylic acid;
6-(2-(S)-carboxy-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester;
6-(2-(R)-carboxy-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester;
(S)-6-((S)-2-carboxy-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester;
(S)-6-((S)-2-carboxy-4,4-difluoro-pyrrolidin-1-ylmethyl)-4-(3,4-difluoro-phenyl)-4-methyl-2-thiazol-2-yl-1,4-dihydro-pyrimidine-5-carboxylic acid methyl ester;
4-[6-(3,4-difluoro-phenyl)-5-methoxycarbonyl-6-methyl-2-thiazol-2-yl-3,6-dihydro-pyrimidin-4-ylmethyl]-morpholine-3-carboxylic acid;
6-(4,4-difluoro-2-methoxycarbonyl-pyrrolidin-1-ylmethyl)-4-(4-fluoro-phenyl)-2-(5-fluoro-pyridin-2-yl)-4-methyl-1,4-dihydro-pyrimidine-5-carboxylic acid methyl ester;
6-(2-carboxy-4,4-difluoro-pyrrolidin-1-ylmethyl)-4-(4-fluoro-phenyl)-2-(5-fluoro-pyridin-2-yl)-4-methyl-1,4-dihydro-pyrimidine-5-carboxylic acid methyl ester;
6-((S)-2-carboxy-4,4-difluoro-pyrrolidin-1-ylmethyl)-4-(4-fluoro-phenyl)-4-methyl-2-(5-methyl-thiazol-2-yl)-1,4-dihydro-pyrimidine-5-carboxylic acid methyl ester;
6-(2-carboxy-4,4-difluoro-2-methyl-pyrrolidin-1-ylmethyl)-4-(4-fluoro-phenyl)-4-methyl-2-thiazol-2-yl-1,4-dihydro-pyrimidine-5-carboxylic acid methyl ester;
(S)-1-[(S)-5-cyano-6-(3,4-difluoro-phenyl)-6-methyl-2-thiazol-2-yl-3,6-dihydro-pyrimidin-4-ylmethyl]-4,4-difluoro-pyrrolidine-2-carboxylic acid;
(S)-6-((S)-2-Carboxy-4,4-difluoro-pyrrolidin-1-ylmethyl)-4-(3,4-difluoro-phenyl)-4-methyl-2-thiazol-2-yl-1,4-dihydro-pyrimidine-5-carboxylic acid ethyl ester;
(S)-6-(2-Carboxy-5,5-difluoro-piperidin-1-ylmethyl)-4-(4-fluoro-phenyl)-4-methyl-2-thiazol-2-yl-1,4-dihydro-pyrimidine-5-carboxylic acid methyl ester;
(S)-6-(2-Carboxy-4,4-difluoro-piperidin-1-ylmethyl)-4-(4-fluoro-phenyl)-4-methyl-2-thiazol-2-yl-1,4-dihydro-pyrimidine-5-carboxylic acid methyl ester;
(S)-6-((S)-2-Carboxy-4,4-difluoro-pyrrolidin-1-ylmethyl)-4-(4-fluoro-phenyl)-4-methyl-2-(1-methyl-1H-imidazol-2-yl)-1,4-dihydro-pyrimidine-5-carboxylic acid methyl ester;
(S)-6-((S)-2-Carboxy-4,4-difluoro-pyrrolidin-1-ylmethyl)-4-(4-fluoro-phenyl)-4-methyl-2-(4-methyl-thiazol-2-yl)-1,4-dihydro-pyrimidine-5-carboxylic acid methyl ester;
(S)-6-((S)-2-Carboxy-4,4-difluoro-pyrrolidin-1-ylmethyl)-2-(5-chloro-thiazol-2-yl)-4-(4-fluoro-phenyl)-4-methyl-1,4-dihydro-pyrimidine-5-carboxylic acid methyl ester;
(S)-6-((S)-2-Carboxy-4,4-difluoro-pyrrolidin-1-ylmethyl)-4-(4-fluoro-phenyl)-4-methyl-2-(5-methyl-thiazol-2-yl)-1,4-dihydro-pyrimidine-5-carboxylic acid methyl ester;
(S)-6-((S)-2-Carboxy-4,4-difluoro-pyrrolidin-1-ylmethyl)-4-(4-fluoro-phenyl)-2-(5-fluoro-thiophen-2-yl)-4-methyl-1,4-dihydro-pyrimidine-5-carboxylic acid methyl ester;
(S)-6-((S)-2-Carboxy-4,4-difluoro-pyrrolidin-1-ylmethyl)-4-(4-fluoro-phenyl)-2-(3-fluoro-thiophen-2-yl)-4-methyl-1,4-dihydro-pyrimidine-5-carboxylic acid methyl ester;
(S)-6-((S)-2-Carboxy-4,4-difluoro-pyrrolidin-1-ylmethyl)-4-(4-fluoro-phenyl)-2-(4-fluoro-thiophen-2-yl)-4-methyl-1,4-dihydro-pyrimidine-5-carboxylic acid methyl ester;
(S)-6-((S)-4,4-Difluoro-2-methoxycarbonyl-pyrrolidin-1-ylmethyl)-4-(4-fluoro-phenyl)-4-methyl-2-thiazol-2-yl-1,4-dihydro-pyrimidine-5-carboxylic acid methyl ester;
(S)-6-(2-Carbamoyl-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester;
(S)-6-((S)-2-Dimethylcarbamoyl-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester;
(S)-6-[(S)-4,4-Difluoro-2-(thiazol-2-ylcarbamoyl)-pyrrolidin-1-ylmethyl]-4-(4-fluoro-phenyl)-4-methyl-2-thiazol-2-yl-1,4-dihydro-pyrimidine-5-carboxylic acid methyl ester;
(S)-6-[(S)-4,4-Difluoro-2-(1-hydroxy-1-methyl-ethyl)-pyrrolidin-1-ylmethyl]-4-(4-fluoro-phenyl)-4-methyl-2-thiazol-2-yl-1,4-dihydro-pyrimidine-5-carboxylic acid methyl ester;
(S)-6-((S)-4,4-Difluoro-2-hydroxymethyl-pyrrolidin-1-ylmethyl)-4-(4-fluoro-phenyl)-4-methyl-2-thiazol-2-yl-1,4-dihydro-pyrimidine-5-carboxylic acid methyl ester;
(S)-6-[(S)-4,4-Difluoro-2-(5-methyl-[1,3,4]oxadiazol-2-yl)-pyrrolidin-1-ylmethyl]-4-(4-fluoro-phenyl)-4-methyl-2-thiazol-2-yl-1,4-dihydro-pyrimidine-5-carboxylic acid methyl ester;
(S)-6-[(S)-4,4-Difluoro-2-(1H-tetrazol-5-yl)-pyrrolidin-1-ylmethyl]-4-(4-fluoro-phenyl)-4-methyl-2-thiazol-2-yl-1,4-dihydro-pyrimidine-5-carboxylic acid methyl ester; and
(S)-6-[(S)-4,4-Difluoro-2-(3-methyl-[1,2,4]oxadiazol-5-yl)-pyrrolidin-1-ylmethyl]-4-(4-fluoro-phenyl)-4-methyl-2-thiazol-2-yl-1,4-dihydro-pyrimidine-5-carboxylic acid methyl ester.

It is very important for a drug to have a moderate or low clearance, as this often lead to a good oral bioavailability and high exposure in target organ. Reducing the clearance of a compound or drug could then potentially reduce drastically the daily dose required for efficacy and therefore give a much better safety profile as well. From the examples below, it has been found a marked increase of metabolic stability and liver exposure of 4-methyldihydropyrimidines of current invention.

4-Hydrogen-dihydropyrimidines such as Bay 41-4109 can be oxidized to pyrimidine product XLVI when treated with human, rat or mouse liver microsomes. In this experiment, pooled liver microsomes (20 mg/ml) from human, male Wister rat and male CD-1 mouse were obtained from BD Bioscience (Franklin Lakes, N.J. USA). Incubation reaction mixtures contained a final concentration of 0.1M sodium phosphate buffer (pH 7.4), 0.5 mg/ml microsomal protein, 5 μM of the tested compounds and 1 mM NADPH in a total volume of 400 μl. The incubations were done for 60 minutes and 300 μl of the mixtures was transferred to 150 μl of ice cold methanol to terminate reactions. After vortexes for 3 minutes and centrifuged at 4000 rpm at 4° C. for 10 minutes, the clear supernatant was used directly for analysis. The samples were analyzed by Applied Biosystems API 3200 Q TRAP LC/MS/MS system using electrospray ionization mode.

Figure 1:
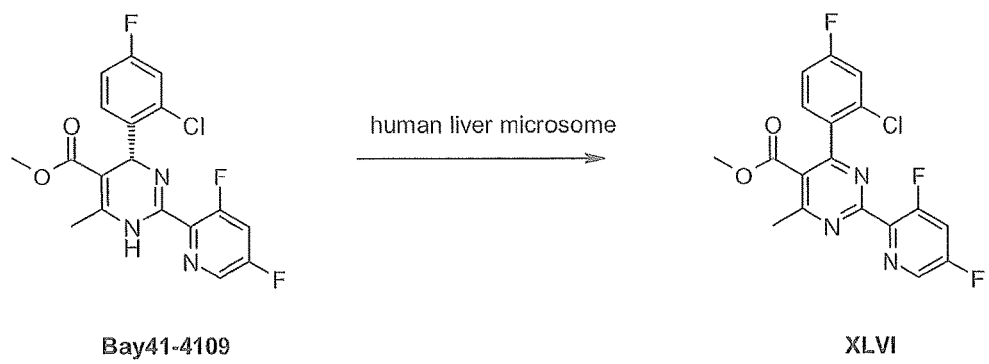
FIG. 1. Bay 41-4109 was converted to XLVI in human liver microsomes.
Figure 2:
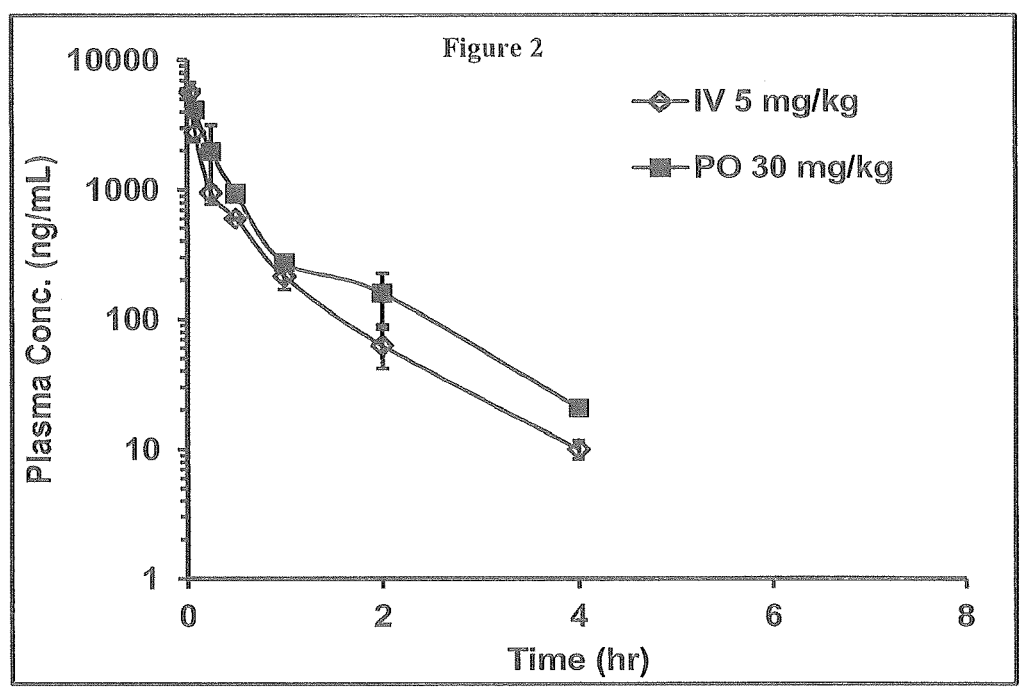
FIG. 2. Mean±SD Plasma Concentration-Time Curve of Bay41-4109 in Male ICR Mice Following Intravenous and Oral Administration*

Pyrimidine product XLVI was the major metabolite in the in vitro clearance tests (FIG. 1), and it was inactive to HBV DNA reduction in HepDE19 cell based assays with $EC_{50}$ value above 100 μM. On the other hand, the 4-methyl-dihydropyrimidines series in this invention do not have the aromatization issues of the core structure.

HBV viruses infect hepatocyte cells and replicate in the liver. To have effective viral suppression, it is important for an anti-HBV drug to have sufficient exposure in the target organ. The following findings highlight increased metabolic stability and high liver exposure of 4-methyldihydropyrimidine analogs in this invention.

In this experiment, fresh mouse liver sample was homogenized by adding saline (1 g liver tissue: 5 mL saline) immediately after collection. After centrifuging for 10 minutes at 14000 rpm, the pooled supernatant was used to prepare liver homogenate solutions. The effective compounds concentrations in liver homogenate were 100, 300, and 1000 ng/mL. Then, they were incubated at rt. After incubation time of 0, 15 and 30 minutes, 180 μl aliquots of MeOH was added into 20 μl of homogenate, respectively. All these samples were vortex mixed for 5 minutes at 1500 rpm and centrifuged for 10 minutes at 14000 rpm. The supernatants were transferred into a 96-well plate for LC-MS/MS analysis. The results were summarized and showed in Table 3.

TABLE 3

The percentage of Bay 41-4109 and Example 13 remaining in mouse liver homogenate.

| Compound | Concentration (ng/mL) | Peak Area* | Incubation Time (min) | Percentage to 0 min |
|---|---|---|---|---|
| Bay41-4109 | 100 | 9263 | 15 | 1.84% |
|  |  | 504715 | 0 | 100% |
|  | 300 | N.D. | 30 | 0% |
|  |  | 1363649 | 0 | 100% |
|  | 1000 | 7868 | 30 | 0.16% |
|  |  | 93431 | 15 | 1.90% |
|  |  | 4930207 | 0 | 100% |
| Example 13 | 100 | 58644 | 15 | 119% |
|  |  | 49480 | 0 | 100% |
|  | 300 | 120162 | 30 | 108% |
|  |  | 111014 | 0 | 100% |
|  | 1000 | 368388 | 30 | 86.0% |
|  |  | 375366 | 15 | 87.6% |
|  |  | 428458 | 0 | 100% |

*the data directly calculated by LC/MS/MS, the relative standard variation is at 20%.
** not detected By comparing the peak area of individual samples at 15 and 30 min to the one at 0 min from same concentration level, the stability of Bay41-4109 and Example 13 in CD-1 mouse liver homogenate was evaluated.

It can be obviously concluded that Bay41-4109 is not stable in liver homogenate treated with saline. About 2% of compound was detected after 15 minutes room temperature incubation, at three different concentration levels. In samples incubated for 30 minutes, only 0.16% can be found (at 1000 ng/mL. Not detected in 100 ng/mL and 300 ng/mL samples due to instrument sensitivity).

It can be concluded that Example 13 is stable in in liver homogenate treated with saline.

The in vivo DMPK of selected compounds were evaluated in male ICR mice following intravenous (or i.v.) or oral (or p.o.) administration. In single dose pharmacokinetics (SDPK) studies, compounds were dissolved in 6% Solutol solution (Solutol:Ethanol, 1:1, v/v), and 94% 0.9% saline for i.v. dose. For p.o. administration, compounds were mixed with 0.89% microcrystalline cellulose and 0.11% carboxymethyl cellulose sodium water solution, or 1% RC591 as suspensions. The single dose exposure levels of Bay 41-4109, Example 6, Example 11, Example 13 and Example 19 in mouse plasma and/or liver are shown as FIG. 2-6.

Synthesis

The compounds of the present invention can be prepared by any conventional means. Suitable processes for synthesizing these compounds as well as their starting materials are provided in the schemes below and in the examples. All substituents, in particular, $R^1$ to $R^5$, M and X are as defined above unless otherwise indicated. Furthermore, and unless explicitly otherwise stated, all reactions, reaction conditions, abbreviations and symbols have the meanings well known to a person of ordinary skill in organic chemistry.

General synthetic scheme for
4-methyl-5-ester-6-methyl-dihydropyrimidine based analogues Intermediate-1 (Scheme 1)

One category of the compounds described herein relates to 4-methyl-5-ester-6-methyl-dihydropyrimidine based analogues with the formula Intermediate-1 wherein $R^8$ is $C_{1-6}$alkyl.

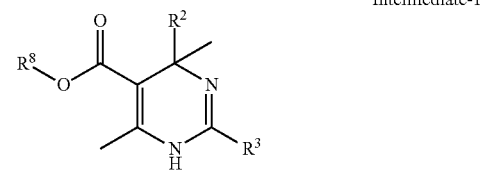

Intermediate-1

Compound of interest Intermediate-1 can be prepared according to the general synthesis method shown in Scheme 1.

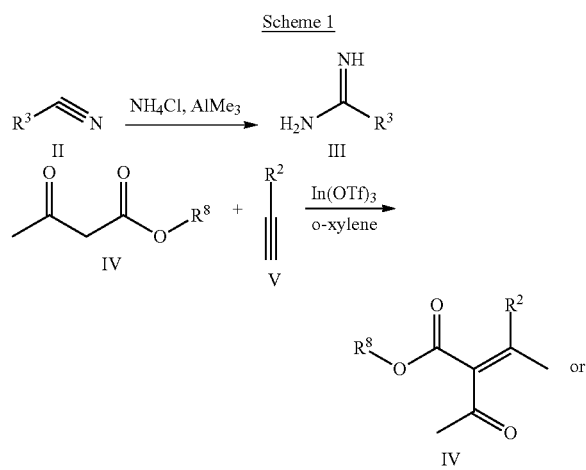

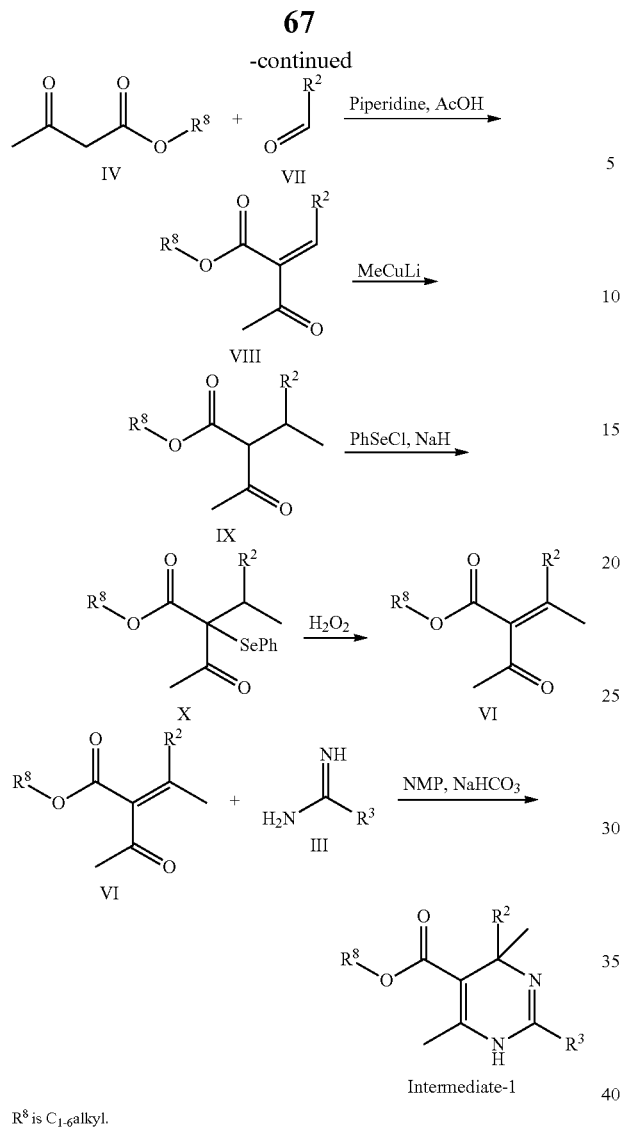

$R^8$ is $C_{1-6}$alkyl.

formed by adding sodium hydride into the solution of ketone IX in THF, then phenylselenyl chloride is added and stirred at rt for 1 hour. After the mixture is treated with pentene, ether and saturated sodium bicarbonate, the organic layer is treated with $H_2O_2$ solution (30%) and stirred at rt for 1 hour.

Analogs with general structure Intermediate-1 can be prepared by the condensation reaction of α,β-unsaturated ketone VI with amidine III. The reaction is typically carried out by adding a solution of VI in NMP dropwisely into a mixture of amidine III and $NaHCO_3$ in NMP at 120° C., after addition the mixture is stirred at 120° C. for half an hour before workup.

General synthetic scheme for 4-methyl-5-cyano-6-nitrogen-substituted-2,4-dihydro-pyrimidine based analogues Intermediate-3 (Scheme-2)

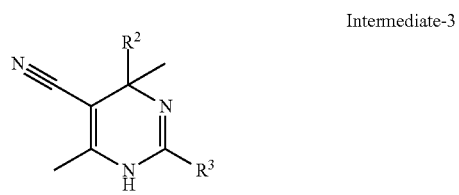

Intermediate-3

Compounds of interest Intermediate-3 can be prepared according to the general synthesis method shown in Scheme 2.

Amidine III can be prepared from commercial available nitrile II, ammonium chloride and trimethyl aluminum. The reaction is typically performed by adding trimethyl aluminum to the mixture of ammonium chloride in toluene at 0° C. After 30 minutes, nitrile II is added into the flask and the reaction mixture is stirred at 80° C. overnight.

The indium triflate catalyzed condensation reaction of commercial available ester IV and ethynyl-benzene V gives α,β-unsaturated ketone VI. The reaction is typically performed in o-xylene at 120° C. for 2 h.

As an alternative method to synthesize tetra-substituted α,β-unsaturated ketone VI, especially when $R^8$ is tert-butyl group. Ketone VIII can be prepared by condensation of ester IV with substituted benzaldehyde VII. The reaction is typically performed in ethanol with catalytic quantity of piperidine and acetic acid at rt overnight.

Ketone IX can be prepared by 1,4-Michael addition of methyl group to the α,β-unsaturated ketone VIII. The reaction is typically performed by adding methyl lithium solution to cuprous iodide in THF solution at 0° C. and stirred for 1 hour at 0° C., then the solution of VIII in THF is added into the mixture at −78° C. and stirred for 1 hour at −78° C.

α,β-Unsaturated ketone VI can be prepared by oxidative elimination of ketone IX. The reaction is typically per-

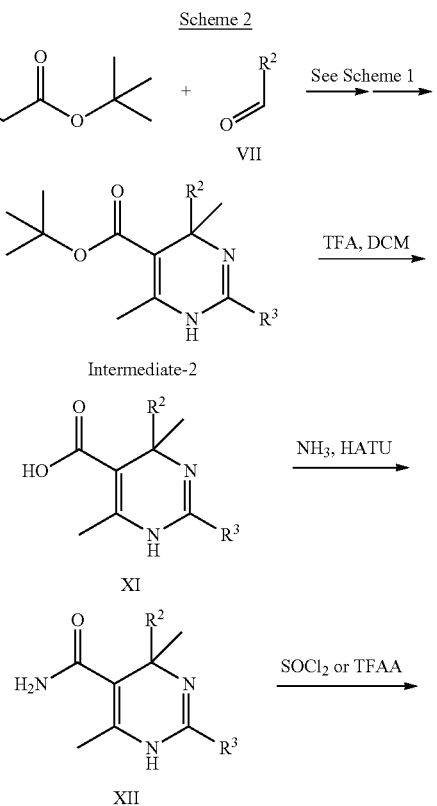

-continued

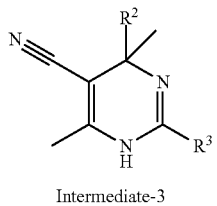

Intermediate-3

Compound XI can be obtained by the deprotection of Intermediate-2. The reaction is typically performed in DCM with TFA at rt for 2 hours.

Compound XII can be obtained by coupling reaction from XI with ammonia. The reaction is typically performed in DCM with HATU and ammonia of dioxane solution at rt for 1 hour.

Cyano compound Intermediate-3 can be obtained by dehydrate reaction from compound XII. The reaction is typically performed in 1,2-dichloroethane with thionyl chloride or trifluoroacetic anhydride under refluxing for 1 hour.

General synthetic scheme for 4-methyl-5-ester or cyano-6-aminoalkyl-dihydropyrimidine based analogues Ia (Scheme 3)

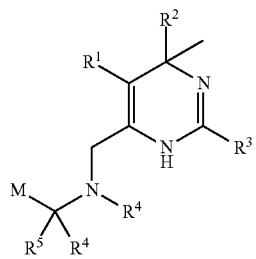

Ia

Compounds of interest Ia can be prepared according to the general synthesis method shown in Scheme 3.

Scheme 3

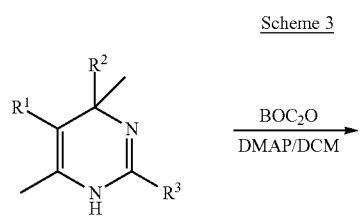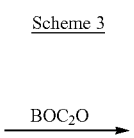

Intermediate-1 or Intermediate-3

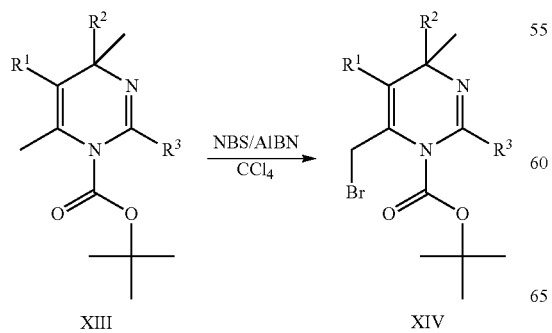

XIII              XIV

-continued

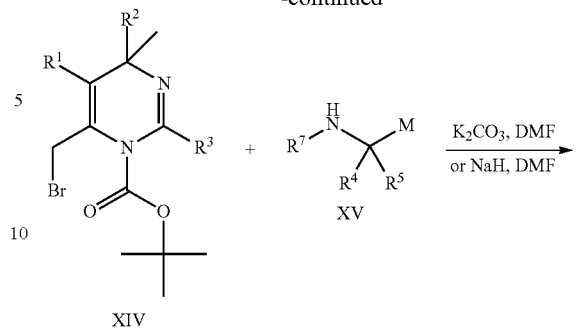

XIV

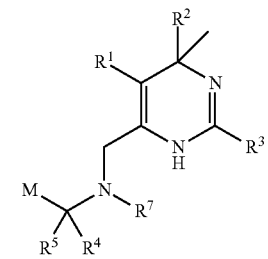

XVI

The Boc-protected compound XIII can be obtained by treatment of ester Intermediate-1 or cyano Intermediate-3 with di-tert-butyldicarbonate and DMAP as base in an inert organic solvent such as DCM, typically at rt for 24 hours.

The compound XIV can be obtained by the bromination of compound XIII. The reaction is typically performed in tetrachloromethane with NBS and AIBN as catalyst at 80° C. for 2 hours.

The amino substituted intermediate XVI can be obtained through substitution reaction of compound XIV with XV. The reaction can be carried out with a suitable organic base such as N,N-diisopropylethylamine, inorganic base such as NaH, Na$_2$CO$_3$, or t-BuOK in an inert organic solvent such as DCM, THF or DMF at rt or 50° C. for 1-10 hours.

Compound Ia can be obtained from the deprotection of XVI treated with TFA in DCM or HCl in MeOH as deprotective agent at rt.

General synthetic scheme for 4-methyl-5-ester or cyano-6-alkoxymethyl-dihydropyrimidine based analogue Ib (Scheme 4)

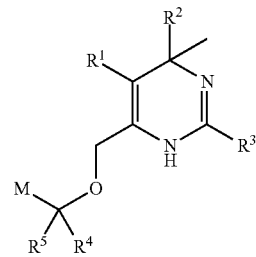

Ib

Compound of interest Ib can be prepared according to the general synthesis method shown in Scheme 4.

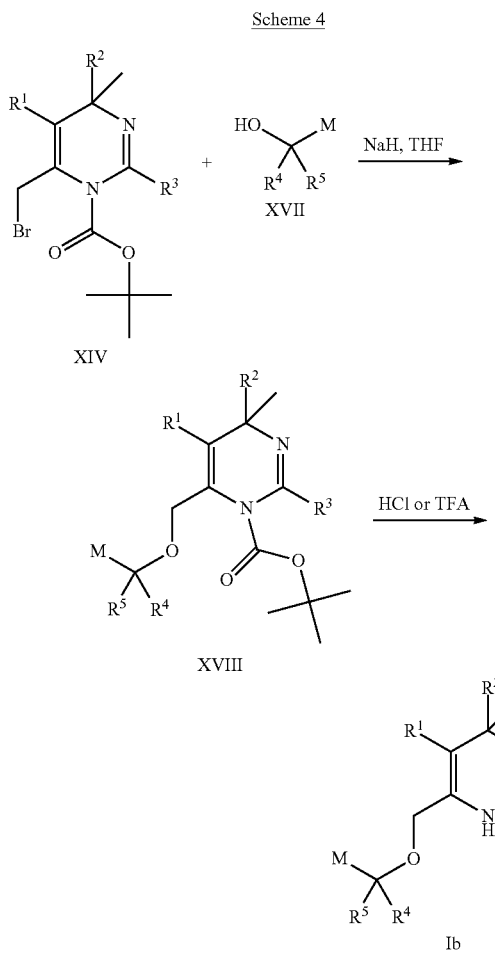

Compound XVIII can be obtained by substitution reaction of compound XIV with alcohol XVII. The reaction is typically performed by adding NaH to the solution of alcohol XVII in anhydrous THF at rt, then bromide XIV is added into the flask and the mixture is stirred at rt for 3 hours.

Compound Ib can be obtained by treating XVIII with TFA in DCM or HCl in MeOH at rt.

This invention also relates to a process for the preparation of a compound of formula I comprising the reaction of
(a) a compound of formula (A)

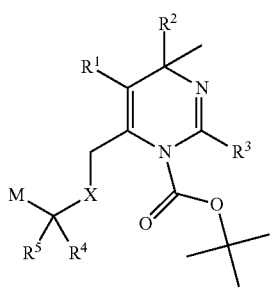

in the presence of an acid;
wherein $R^1$ to $R^5$, M and X are defined above unless otherwise indicated.

In step (a), the acid can be for example TFA or HCl.

Pharmaceutical Compositions and Administration

The invention also relates to a compound of formula I for use as therapeutically active substance.

A compound of formula (I) when manufactured according to the above process is also an object of the invention.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular human being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to the suppression of serum HBV DNA levels, or HBeAg seroconversion to HBeAb, or HBsAg loss, or normalization of alanine aminotransferase levels and improvement in liver histology. For example, such amount may be below the amount that is toxic to normal cells, or the human as a whole.

In one example, the pharmaceutically effective amount of the compound of the invention administered parenterally per dose will be in the range of about 0.01 to 100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc.

Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 mg to 1000 mg of the compound of the invention compounded with about 90 mg to 30 mg anhydrous lactose, about 5 mg to 40 mg sodium croscarmellose, about 5 mg to 30 mg polyvinylpyrrolidone (PVP) K30, and about 1 mg to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Indications and Methods of Treatment

The compounds of the invention can inhibit HBV's de novo DNA synthesis and reduce HBV DNA levels. Accordingly, the compounds of the invention are useful for the treatment or prophylaxis of HBV infection.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method of treating or prophylaxising HBV infection in a human in need of such treatment, wherein the method comprises administering to said human a therapeutically effective amount of a compound of Formula I, a stereoisomer, tautomer, prodrug or pharmaceutically acceptable salt thereof.

Combination Therapy

The compounds of the invention can be used together with interferon, pegylated interferons, Lamivudine, Adefovir dipivoxil, Entecavir, Telbivudine, and Tenofovir disoproxil for the treatment or prophylaxis of HBV.

EXAMPLES

The invention will be more fully understood by reference to the following examples. They should not, however, be construed as limiting the scope of the invention.

Abbreviations used herein are as follows:
AIBN: azobisisobutyronitrile
Boc: tert-butoxycarbonyl
t-BuOK: potassium tert-butoxide
Calc'd: calculated
$CC_{50}$: cytotoxic concentration 50%
$CCl_4$: tetrachloromethane
$CDCl_3$: deuterated chloroform
CCK-8: cell counting kit-8
CDI: N,N'-Carbonyldiimidazole
CMV: cytomegalovirus
d: day
DIPEA: N,N-diisopropylethylamine
DCM: dichloromethylene
DMAP: N,N'-dimethylaminopyridine
DMF: dimethylformamide
DMSO: dimethylsulfoxide
DNA: deoxyribonucleic acid
EDCI: 1-ethyl-3-(3-dimethylaminopropyl)carbodiimide
EDTA: ethylenediaminetetraacetic acid
exp: expected
EtOAc: ethyl acetate
FBS: fetal bovine serum
g: gram
$EC_{50}$: concentration required for 50% induction of acetylated tubulin
FBS: fetal bovine serum
h: hour or hours
HAP: heteroaryldihydropyrimidine
HATU: 2-(7-Aza-1H-benzotriazole-1-yl)-1,1,3,3-tetramethyluronium hexafluorophosphate
HBeAb: hepatitis B e antibody
HBeAg: hepatitis B e antigen
HBsAg: hepatitis B surface antigen
HCl: hydrogen chloride
HPLC: high performance liquid chromatography
Hz: Hertz
$In(OTf)_3$: indium (III) trifluoromethanesulfonate
IPA: isopropanol
KOH: potassium
LC/MS: liquid chromatography mass spectrometer
LiOH: lithium hydroxide
LDA: lithium diisopropylamide
MeOD-d4 or CD3OD: deuterated methanol
MeOH: methanol
mg: milligram
MHz: megahertz
min: minute or minutes
mL: milliliter
mM: milliliter
NMP: 1-methyl-piperidin-2-one
mmol: millimole NaCl: sodium chloride
NaOH: sodium hydroxide
NBS: N-bromosuccinimide
NEt$_3$: triethylamine
NMR: nuclear magnetic resonance
PBS: Phosphate buffered saline
prep-HPLC: preparative high performance liquid chromatography
RP-HPLC: reverse phase high performance liquid chromatography
rt: room temperature
SDPK: single dose pharmacokinetics
SFC: supercritical fluid chromatography
SSC: saline-sodium citrate buffer
TEA: triethylamine
TFA: trifluoroacetic acid
TFAA: trifluoroacetic acid anhydride
THF: tetrahydrofuran
μl: microliter
μM: micromole General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C$_{18}$ (5 μm, OBD™ 30×100 mm) column or SunFire™ Prep-C$_{18}$ (5 μm, OBD™ 30×100 mm) column. Waters AutoP purification System (Column: XBridge™ Prep-C$_{18}$, 30×100 mm, Sample Manager 2767, Pump 2525, Detector: Micromass ZQ and UV 2487, solvent system: acetonitrile and 0.1% ammonium hydroxide in water). For SFC chiral separation, intermediates were separated by chiral column (Daicel chiralpak IC, 5 μm, 30×250 mm) column using Mettler Toledo SFC-Multigram III system, solvent system: 95% CO$_2$ and 5% IPA (0.5% TEA in IPA), back pressure 100 bar, detection UV@ 254 nm.

LC/MS spectra of compounds were obtained using a LC/MS (Waters™ Alliance 2795-Micromass ZQ). LC/MS conditions were as follows (running time 6 min):
Acidic condition: A: 0.1% formic acid in H$_2$O; B: 0.1% formic acid in acetonitrile;
Basic condition: A: 0.01% NH$_3$.H$_2$O in H$_2$O; B: acetonitrile; Neutral condition: A: H$_2$O; B: acetonitrile.

Mass spectra (MS): generally only ions which indicate the parent mass are reported, and unless otherwise stated the mass ion quoted is the positive mass ion (M+H)'.

LC-MS/MS instrument on liver homogenate stability test: An Agilent 1290 series LC system composited of a binary pump, a degasser, a CTCPAL autosampler and a thermostatted column was applied. The Chromatographic separation was achieved on a Chromolith Performance RP-18 endcapped (3×100 mm) at room temperature.

Mass spectrometric detection was performed on an Agilent 6530 Q-TOF instrument in full scan mode with an AJS ESI interface in positive ionization mode. Data processing was performed with Agilent MassHunter Workstation Data Acquisition B.04.00 and Agilent MassHunter Workstation Qualitative Analysis B.04.00.

The microwave assisted reactions were carried out in a Biotage Initiator Sixty microwave synthesizer.

NMR Spectra were obtained using Bruker Avance 400 MHz.

All reactions involving air-sensitive reagents were performed under an argon atmosphere. Reagents were used as received from commercial suppliers without further purification unless otherwise noted.

The following examples were prepared by the general methods outlined in the schemes above. They are intended to illustrate the meaning of the present invention but should by no means represent a limitation within the meaning of the present invention.

PREPARATIVE EXAMPLES

Example 1

4-(4-Fluoro-phenyl)-6-(1-methoxycarbonyl-1-methyl-ethoxymethyl)-4-methyl-2-thiazol-2-yl-1,4-dihydro-pyrimidine-5-carboxylic acid methyl ester The title compound was prepared according to the general synthesis methods shown in Scheme 1 and Scheme 4. A detailed synthesis route is provided as shown in Scheme 5

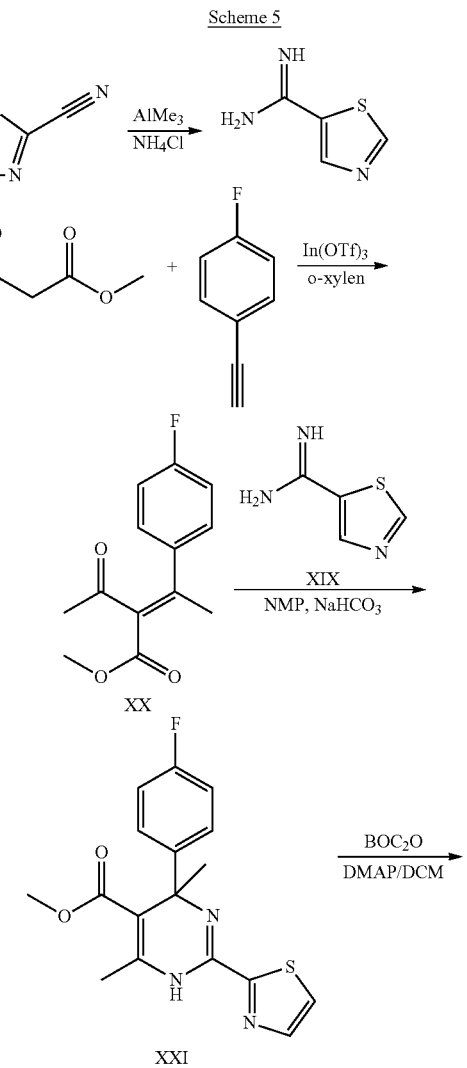

Scheme 5

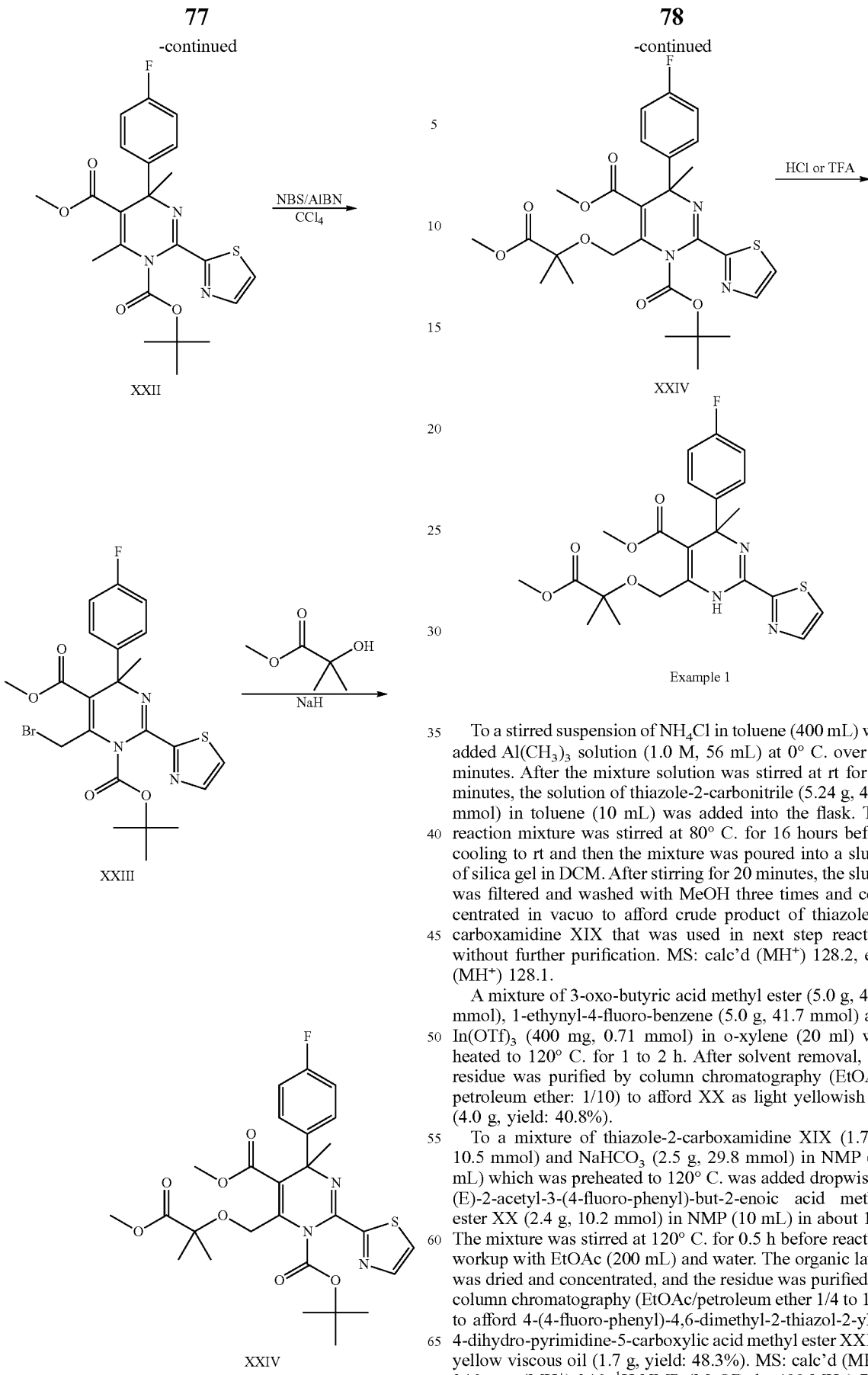

To a stirred suspension of NH₄Cl in toluene (400 mL) was added Al(CH₃)₃ solution (1.0 M, 56 mL) at 0° C. over 30 minutes. After the mixture solution was stirred at rt for 30 minutes, the solution of thiazole-2-carbonitrile (5.24 g, 47.6 mmol) in toluene (10 mL) was added into the flask. The reaction mixture was stirred at 80° C. for 16 hours before cooling to rt and then the mixture was poured into a slurry of silica gel in DCM. After stirring for 20 minutes, the slurry was filtered and washed with MeOH three times and concentrated in vacuo to afford crude product of thiazole-2-carboxamidine XIX that was used in next step reaction without further purification. MS: calc'd (MH⁺) 128.2, exp (MH⁺) 128.1.

A mixture of 3-oxo-butyric acid methyl ester (5.0 g, 43.1 mmol), 1-ethynyl-4-fluoro-benzene (5.0 g, 41.7 mmol) and In(OTf)₃ (400 mg, 0.71 mmol) in o-xylene (20 ml) was heated to 120° C. for 1 to 2 h. After solvent removal, the residue was purified by column chromatography (EtOAc/petroleum ether: 1/10) to afford XX as light yellowish oil (4.0 g, yield: 40.8%).

To a mixture of thiazole-2-carboxamidine XIX (1.7 g, 10.5 mmol) and NaHCO₃ (2.5 g, 29.8 mmol) in NMP (10 mL) which was preheated to 120° C. was added dropwisely (E)-2-acetyl-3-(4-fluoro-phenyl)-but-2-enoic acid methyl ester XX (2.4 g, 10.2 mmol) in NMP (10 mL) in about 1 h. The mixture was stirred at 120° C. for 0.5 h before reaction workup with EtOAc (200 mL) and water. The organic layer was dried and concentrated, and the residue was purified by column chromatography (EtOAc/petroleum ether 1/4 to 1/2) to afford 4-(4-fluoro-phenyl)-4,6-dimethyl-2-thiazol-2-yl-1,4-dihydro-pyrimidine-5-carboxylic acid methyl ester XXI as yellow viscous oil (1.7 g, yield: 48.3%). MS: calc'd (MH⁺) 346, exp (MH⁺) 346. ¹H NMR (MeOD-d₄, 400 MHz) 7.93

(d, 1H, J=3.2 Hz), 7.72 (d, 1H, J=3.2 Hz), 7.51-7.47 (m, 2H), 7.04 (t, 2H, J=8.8 Hz), 3.45 (s, 3H), 2.28 (s, 3H), 1.90 (s, 3H).

To a solution of XXI (1.0 g, 2.9 mmol) in DCM (20 mL) was added DMAP (0.15 g, 1.2 mmol) and Boc$_2$O (0.94 g, 4.3 mmol), and the mixture was stirred overnight. The mixture was washed with water (15 mL) and brine (15 mL). The organic layer was separated, dried over anhydrous Na$_2$SO$_4$ and concentrated, and the residue was purified by column chromatography (EtOAc/petroleum ether from 1/4 to 1/3) to afford 4-(4-fluoro-phenyl)-4,6-dimethyl-2-thiazol-2-yl-4H-pyrimidine-1,5-dicarboxylic acid 1-tert-butyl ester 5-methyl ester XXII as yellow solid (0.91 g, yield: 70.5%).

A solution of XXII (0.90 g, 2.02 mmol) and NBS (0.54 g, 3.03 mmol) in CCl$_4$ (30 mL) was heated to 50° C., then AIBN (30 mg) was added to initiate the reaction. The mixture was stirred for 2 h. The mixture was purified by column chromatography (EtOAc/petroleum ether from 1/4 to 1/3) to afford 6-bromomethyl-4-(4-fluoro-phenyl)-4-methyl-2-thiazol-2-yl-4H-pyrimidine-1,5-dicarboxylic acid 1-tert-butyl ester 5-methyl ester XXIII as yellow solid (1.03 g, yield: 97.3%).

Sodium hydride (12 mg, 0.5 mmol) was added to a solution of 2-hydroxy-2-methyl-propionic acid methyl ester (59 mg, 0.5 mmol) in THF at rt. Then the mixture was stirred at rt for 30 min. Compound XXIII (105 mg, 0.2 mmol) was added and stirred at rt overnight. Then the mixture was partitioned between water and EtOAc. The organic phase was dried, concentrated and used in the next step without further purification.

The crude product XXIV from above step was dissolved in DCM and then TFA was added. The mixture was stirred at rt for 2 hours. The solvent was removed and the residue was purified by prep-HPLC to afford Example 1 as yellow solid (40 mg, yield: 43% for 2 steps). MS: calc'd 462 (MH$^+$), exp 462 (MH$^+$). $^1$H NMR (MeOD-d$_4$, 400 MHz), 7.95 (d, 1H, J=3.2 Hz), 7.75 (d, 1H, J=3.2 Hz), 7.49-7.45 (m, 2H), 7.04 (t, 2H, J=8.8 Hz), 4.71-4.62 (m, 2H), 3.80 (s, 3H), 3.43 (s, 3H), 1.92 (s, 3H), 1.57 (s, 6H).

Example 2

6-(1-Carboxy-2,2,2-trifluoro-ethoxymethyl)-4-(4-fluoro-phenyl)-4-methyl-2-thiazol-2-yl-1,4-dihydro-pyrimidine-5-carboxylic acid methyl ester The title compound was prepared in analogy to Example 1 in Scheme 5 by using 3,3,3-trifluoro-2-hydroxy-propionic acid methyl ester instead of 2-hydroxy-2-methyl-propionic acid methyl ester, the so-obtained methyl ester was hydrolyzed by LiOH as indicated in Scheme 3. MS: calc'd 488 (MH$^+$), exp 488 (MH$^+$). $^1$H NMR (MeOD-d$_4$, 400 MHz), 7.94 (d, 1H, J=2.8 Hz), 7.93 (d, 1H, J=2.8 Hz), 7.53-7.49 (m, 2H), 7.07-7.03 (m, 2H), 4.85-4.78 (m, 2H), 4.40-4.37 (m, 1H), 3.44 (s, 3H), 1.94 (s, 3H).

Example 3

6-{[(1-Carboxy-cyclopropyl)-methyl-amino]-methyl}-4-(4-fluoro-phenyl)-4-methyl-2-thiazol-2-yl-1,4-dihydro-pyrimidine-5-carboxylic acid methyl ester The title compound was prepared according to the synthesis method shown in Scheme 1 and Scheme 3. A detailed synthesis route is provided as shown in Scheme 6.

Scheme 6

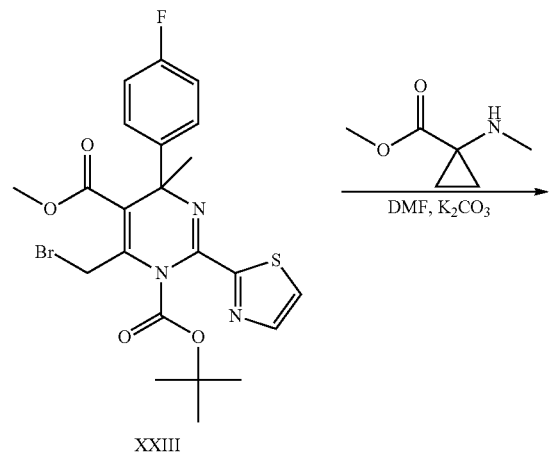

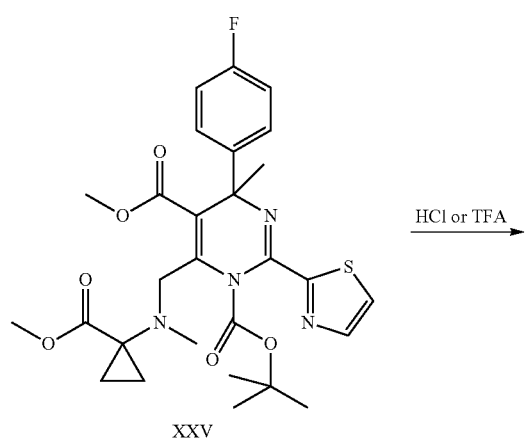

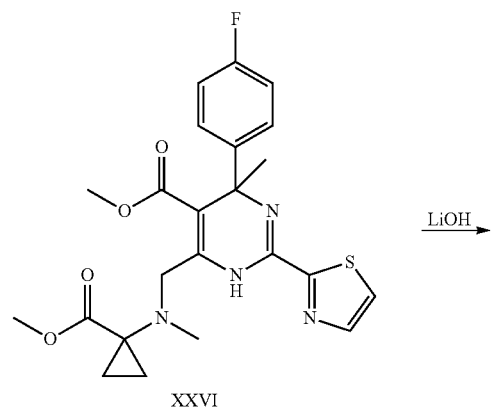

81
-continued

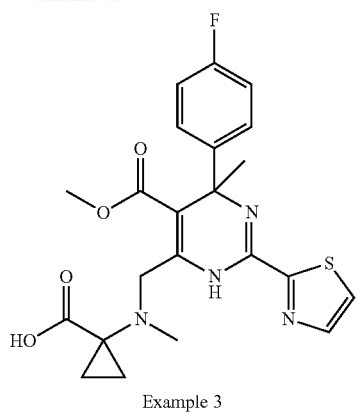

Example 3

To a solution of 6-bromomethyl-4-(4-fluoro-phenyl)-4-methyl-2-thiazol-2-yl-4H-pyrimidine-1,5-dicarboxylic acid 1-tert-butyl ester 5-methyl ester XXIII (1.00 g, 1.90 mmol) and potassium carbonate in DMF was added 1-methyl-amino-cyclopropanecarboxylic acid methyl ester (258 mg, 2.00 mmol), the mixture was stirred at 40° C. for 3 hours and LC-MS indicated that the reaction was finished. The mixture was partitioned between water and ethyl acetate. The organic phase was dried and concentrated to afford the crude product used in the next step without further purification.

The crude product XXV from above step was dissolved in DCM and then TFA was added. The mixture was stirred at rt for 2 hours. LC-MS indicated that the reaction was finished. The solvent was removed and the residue was used in the next step without further purification.

The crude product XXVI from above step was dissolved in MeOH (5 mL) and LiOH in water (2 mL) was added to the mixture. The mixture was stirred at rt for 2 h and LC-MS indicated that the reaction was finished. The solvent was removed and the mixture was adjusted to pH (3-5) with diluted hydrochloric acid. The mixture was purified by prep-HPLC to afford Example 3 as yellow solid (0.63 g, yield for 3 steps: 73%). MS: calc'd 459 (MH$^+$), exp 459 (MH$^+$). $^1$H NMR (MeOD-d$_4$, 400 MHz), 8.12 (d, 1H, J=3.2 Hz), 8.06 (d, 1H, J=3.2 Hz), 7.63-7.60 (m, 2H), 7.15 (t, 2H, J=8.8 Hz), 4.30 (s, 2H), 3.51 (s, 3H), 2.79 (s, 3H), 2.10 (s, 3H), 1.52-1.51 (m, 2H), 1.38-1.37 (m, 2H).

Example 4

4-[6-(4-Fluoro-phenyl)-5-methoxycarbonyl-6-methyl-2-thiazol-2-yl-3,6-dihydro-pyrimidin-4-ylmethyl]-morpholine-3-carboxylic acid The title compound was prepared in analogy to Example 3 in Scheme 6 by using morpholine-3-carboxylic acid methyl ester instead of 1-methylamino-cyclopropanecarboxylic acid methyl ester. LC-MS: calc'd 475 (MH$^+$), exp 475 (MH$^+$). $^1$H NMR (MeOD-d$_4$, 400 MHz) δ 8.10 (d, 1H), 8.03 (d, 1H), 7.64-7.61 (m, 2H), 7.15-7.12 (m, 2H), 4.32-4.31 (m, 2H), 4.18-4.14 (m, 2H), 3.99-3.72 (m, 3H), 3.51-3.49 (m, 4H), 3.02 (m, 1H), 2.11 (d, 3H).

82

Example 5

4-[6-(4-Fluoro-phenyl)-5-methoxycarbonyl-6-methyl-2-thiazol-2-yl-3,6-dihydro-pyrimidin-4-ylmethyl]-morpholine-(S)-3-carboxylic acid methyl ester The title compound was prepared in analogy to Example 3 in Scheme 6 by using morpholine-(S)-3-carboxylic acid methyl ester instead of 1-methylamino-cyclopropanecarboxylic acid methyl ester.

Example 6

4-[6-(4-Fluoro-phenyl)-5-methoxycarbonyl-6-methyl-2-thiazol-2-yl-3,6-dihydro-pyrimidin-4-ylmethyl]-morpholine-(S)-3-carboxylic acid The title compound was prepared by from the hydrolysis of Example 5 with LiOH in MeOH as shown in Scheme 6.

Example 7

(S)-4-[6-(4-Fluoro-phenyl)-5-methoxycarbonyl-6-methyl-2-thiazol-2-yl-3,6-dihydro-pyrimidin-4-ylmethyl]-morpholine-(S)-3-carboxylic acid The title compound was prepared according to the synthesis method shown in Scheme 1 and Scheme 3. A detailed synthesis route is provided as shown in Scheme 7.

Scheme 7

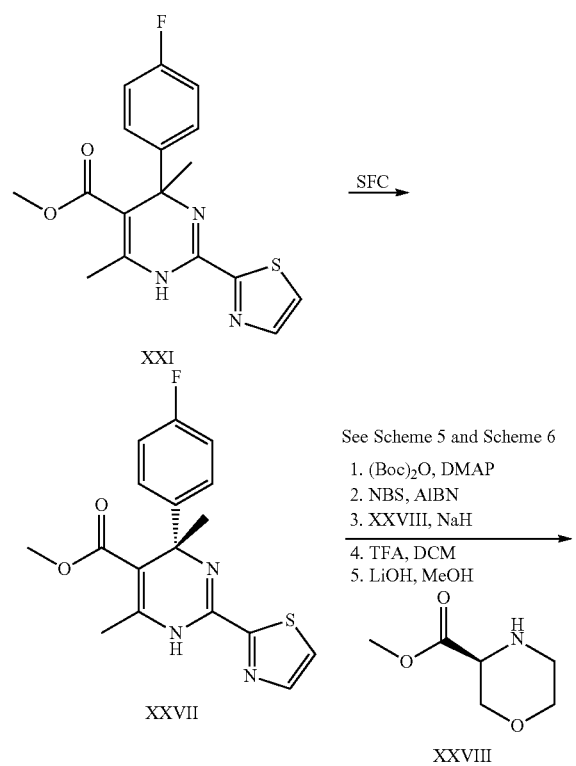

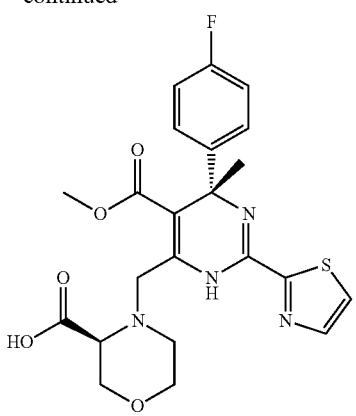

Example 7

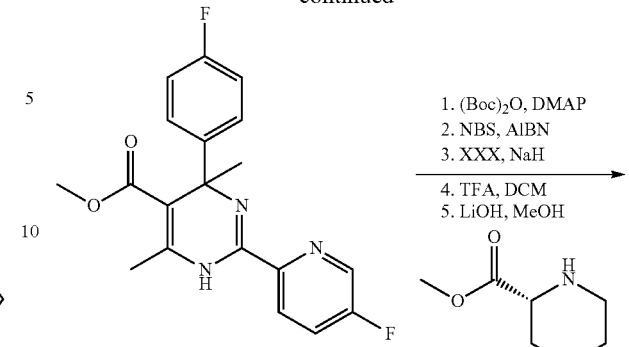

Figure 7:
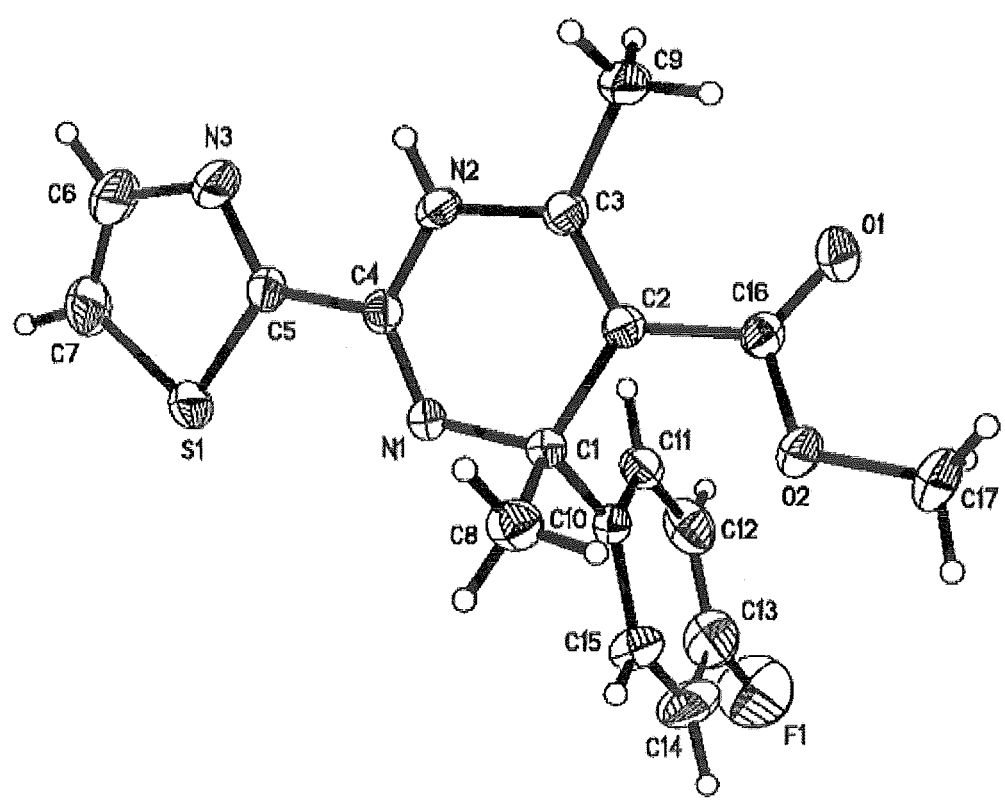

The chiral intermediate compound XXVII was separated from XXI by SFC and the absolute stereochemistry was determined by X-ray diffraction study (please see FIG. 7). The title compound was prepared in analogy to Example 3 in Scheme 6 by using morpholine-(S)-3-carboxylic acid methyl ester XXVIII instead of 1-methylamino-cyclopropanecarboxylic acid methyl ester in the replacement reaction.

Example 8

(S)-4-[6-(4-Fluoro-phenyl)-5-methoxycarbonyl-6-methyl-2-thiazol-2-yl-3,6-dihydro-pyrimidin-4-ylm-ethyl]-morpholine-(R)-3-carboxylic acid The title compound was prepared in analogy to Example 7 in Scheme 7 by using morpholine-(R)-3-carboxylic acid methyl ester instead of 1-methylamino-cyclopropanecarboxylic acid methyl ester.

Example 9

4-[6-(4-Fluoro-phenyl)-2-(5-fluoro-pyridin-2-yl)-5-methoxycarbonyl-6-methyl-3,6-dihydro-pyrimidin-4-ylmethyl]-morpholine-(R)-3-carboxylic acid The title compound was prepared according to the methods shown in Scheme 8.

Scheme 8

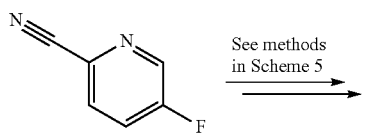

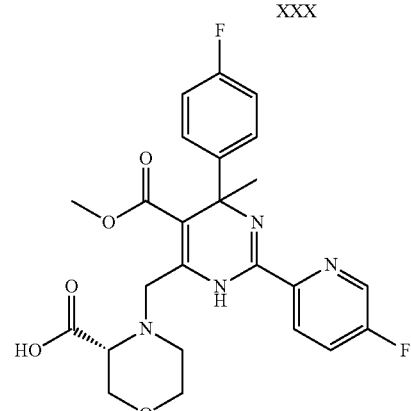

Example 9

5-Fluoro-pyridine-2-carbonitrile was used in the synthesis of Compound XXIX in the same methods as shown in Scheme 5. Following similar procedures to Scheme 5 and Scheme 6, XXIX was converted to Example 9 by using morpholine-(R)-3-carboxylic acid methyl ester XXX in the replacement reaction.

Example 10

4-[6-(4-Fluoro-phenyl)-2-(5-fluoro-pyridin-2-yl)-5-methoxycarbonyl-6-methyl-3,6-dihydro-pyrimidin-4-ylmethyl]-morpholine-(S)-3-carboxylic acid The title compound was prepared in analogy to Example 9 in Scheme 8 by using morpholine-(S)-3-carboxylic acid methyl ester instead of morpholine-(R)-3-carboxylic acid methyl ester in the replacement reaction.

Example 11

6-(2-(S)-Carboxy-4,4-difluoro-pyrrolidin-1-ylm-ethyl)-4-(4-fluoro-phenyl)-4-methyl-2-thiazol-2-yl-1,4-dihydro-pyrimidine-5-carboxylic acid methyl ester The title compound was prepared in analogy to Example 3 in Scheme 6 by using 4,4-difluoro-pyrrolidine-(S)-2-carboxylic acid methyl ester instead of 1-methylamino-cyclopropanecarboxylic acid methyl ester.

Example 12

6-(2-(R)-Carboxy-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 3 in Scheme 6 by using 4,4-difluoro-pyrrolidine-(R)-2-carboxylic acid methyl ester instead of 1-methylamino-cyclopropanecarboxylic acid methyl ester.

Example 13

(S)-6-((S)-2-Carboxy-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using 4,4-difluoro-pyrrolidine-(S)-2-carboxylic acid methyl ester instead of using morpholine-(S)-3-carboxylic acid methyl ester XXVIII in the replacement reaction.

Example 14

(S)-6-((S)-2-Carboxy-4,4-difluoro-pyrrolidin-1-ylmethyl)-4-(3,4-difluoro-phenyl)-4-methyl-2-thiazol-2-yl-1,4-dihydro-pyrimidine-5-carboxylic acid methyl ester The title compound was prepared according to the synthesis method shown in Scheme 1 and Scheme 3. A detailed synthesis route is provided as shown in Scheme 9.

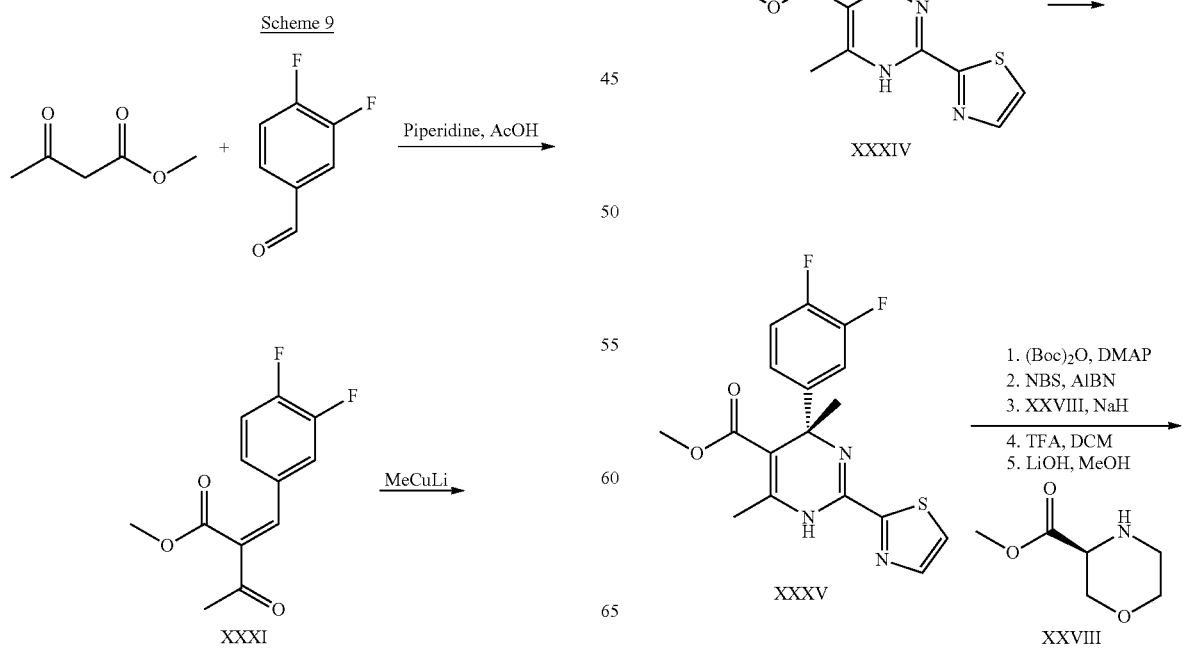

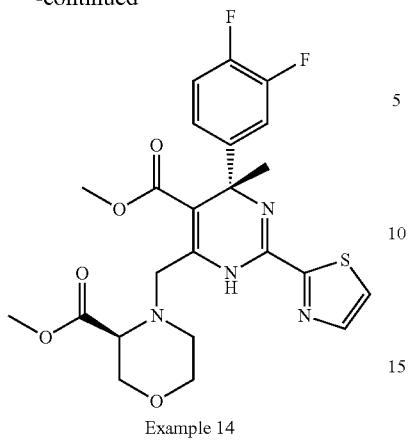

Example 14

A mixture of 3,4-difluoro-benzaldehyde (8.96 g, 63.1 mmol), 3-oxo-butyric acid methyl ester (7.32 g, 63.1 mmol), piperidine (0.27 g, 3.16 mmol) and acetic acid (0.19 g, 3.16 mmol) in anhydrous ethanol (200 mL) was stirred for 12 hours at room temperature. After removal of the solvent, the residue was purified by flash column chromatography (EtOAc:hexane=1:10) to afford the product of 2-[1-(3,4-difluoro-phenyl)-meth-(Z)-ylidene]-3-oxo-butyric acid methyl ester XXXI as yellow solid (13.6 g). Yield: 90%. MS: calc'd (M$^+$+H) 241.0, exp (M$^+$+H) 241.1.

A solution of methyllithium (1.6 M in ether, 48.7 mL, 78 mmol) was added to a suspension of copper(I) iodide (14.9 g, 78 mmol) in 200 mL of anhydrous THF under argon at 0° C. and the mixture was stirred for 1 hour at 0° C. A solution of XXXI (8.0 g, 31.2 mmol) in 50 mL of anhydrous THF was added dropwisely into the mixture at −78° C. After stirring at −78° C. for 1 hour, the reaction mixture was quenched with saturated ammonium chloride solution, extracted with EtOAc, washed with brine and dried over anhydrous sodium sulfate. After removal of organic solvent, the residue was purified by flash column chromatography (EtOAc:hexane=1:10) to afford 6.39 g of XXXII as oil. Yield: 80%. MS: calc'd (M$^+$+H) 257.1.

NaH (60%, 1.10 g, 27.5 mmol) was added into a solution of XXXII (5.0 g, 18.3 mmol) in anhydrous THF (100 mL) under argon. A solution of phenylselenyl chloride (5.3 g, 27.5 mmol) in THF (20 mL) was added into the flask at rt through syringe and the mixture was stirred at rt for 1 h. 60 mL of pentene/ether mixture (v/v=1/1) and 30 mL of saturated NaHCO$_3$ solution were added into the reaction mixture. The organic layer was separated and washed with brine, and treated with H$_2$O$_2$ solution (30%, 4 mL) in DCM (50 mL). The mixture was stirred at rt (for 0.5-2 hours) and diluted with DCM (100 mL). The organic phase was separated, washed with saturated sodium bicarbonate, sodium sulfite, water and brine in sequential and dried over anhydrous sodium sulfate. After removal of organic solvent, the residue was purified by flash column chromatography (EtOAc:hexane=1:10) to afford 3.97 g of XXXIII as yellow oil. MS: calc'd (M$^+$+H) 255.1, exp (M$^+$+H) 255.1

A mixture of XXXIII (2.54 g, 10 mmol), thiazole-2-carboxamidine hydrochloride XIX (1.6 g, 10 mmol) and sodium bicarbonate (1.68 g, 20 mmol) in NMP (15 mL) was stirred for 3 hours at 120° C. After cooling, the mixture was separated between water and ethyl acetate. The organic phase was dried and concentrated. The residue was purified to afford the product of 4-(3,4-difluoro-phenyl)-4,6-dimethyl-2-thiazol-2-yl-1,4-dihydro-pyrimidine-5-carboxylic acid methyl ester XXXIV as yellow solid (2.00 g). Yield: 55%. MS: calc'd (M$^+$+H) 363.1, exp (M$^+$+H) 363.1.

The chiral intermediate XXXV was separated from XXXIV by SFC and the absolute configuration was assigned through comparing its retention time on SFC with that of the stereochemistry known compound XXVII.

The title compound Example 14 was prepared in analogy to Example 7 in Scheme 7 from Compound XXXV.

Example 15

4-[(S)-6-(3,4-Difluoro-phenyl)-5-methoxycarbonyl-6-methyl-2-thiazol-2-yl-3,6-dihydro-pyrimidin-4-ylmethyl]-morpholine-3-carboxylic acid methyl ester The title compound was prepared by the methods shown in Scheme 10 by using XXXIV in the bromination and following replacement reactions, which were carried out in the same procedures as Scheme 5 and Scheme 6.

Scheme 10

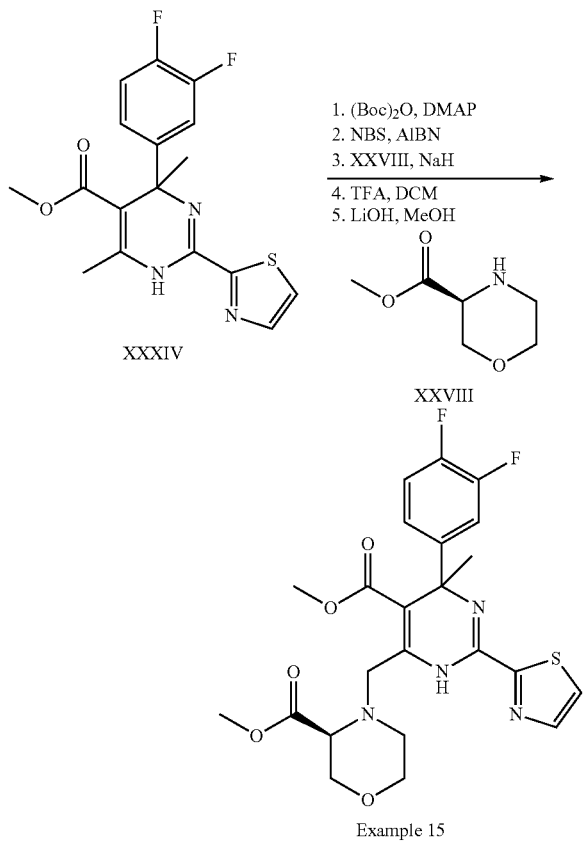

Example 15

Example 16

4-[6-(3,4-Difluoro-phenyl)-5-methoxycarbonyl-6-methyl-2-thiazol-2-yl-3,6-dihydro-pyrimidin-4-ylmethyl]-morpholine-3-carboxylic acid The title compound was obtained by hydrolysis of Example 15 with LiOH in MeOH.

Example 17

6-(4,4-Difluoro-2-methoxycarbonyl-pyrrolidin-1-ylmethyl)-4-(4-fluoro-phenyl)-2-(5-fluoro-pyridin-2-yl)-4-methyl-1,4-dihydro-pyrimidine-5-carboxylic acid methyl ester The title compound was prepared in analogy to Example 9 in Scheme 8 by using 4,4-difluoro-pyrrolidine-(S)-2-carboxylic acid methyl ester instead of morpholine-(R)-3-carboxylic acid methyl ester XXXVIII in the replacement reaction.

Example 18

(S)-6-((S)-2-Carboxy-4,4-difluoro-pyrrolidin-1-ylmethyl)-4-(4-fluoro-phenyl)-2-(5-fluoro-pyridin-2-yl)-4-methyl-1,4-dihydro-pyrimidine-5-carboxylic acid methyl ester The title compound was prepared in the methods as shown in Scheme 11.

Scheme 11

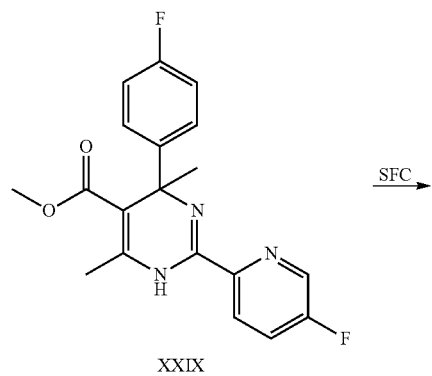

XXIX

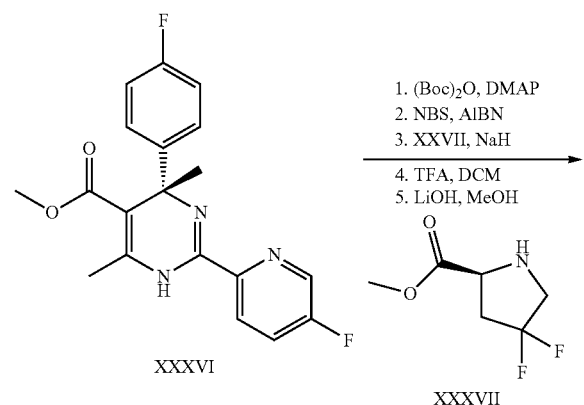

XXXVI 1. (Boc)₂O, DMAP
2. NBS, AIBN
3. XXVII, NaH
4. TFA, DCM
5. LiOH, MeOH

XXXVII

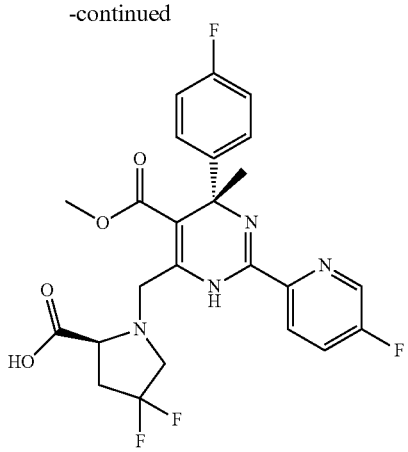

Example 9

Compound XXXVI was obtained by SFC chiral separation of intermediate XXIX and the absolute configuration was assigned through comparing its retention time on SFC with that of the stereochemistry known compound XXVII. Example 9 was prepared from XXXVI by following the procedures in Scheme 5 and Scheme 6, except that 4,4-difluoro-pyrrolidine-(S)-2-carboxylic acid methyl ester XXXVII was used in the replacement reaction.

Example 19

6-((S)-2-Carboxy-4,4-difluoro-pyrrolidin-1-ylmethyl)-4-(4-fluoro-phenyl)-4-methyl-2-(5-methyl-thiazol-2-yl)-1,4-dihydro-pyrimidine-5-carboxylic acid methyl ester The title compound was prepared in the methods as shown in Scheme 12 by using 5-methyl-thiazole-2-carbonitrile in the preparation of ammidine. Compound XXXVIII was obtained by following the procedures in Scheme 5. And 4,4-difluoro-pyrrolidine-(S)-2-carboxylic acid methyl ester XXXVII was used in the preparation of Example 19, in methods similar to Scheme 5 and Scheme 6.

Scheme 12

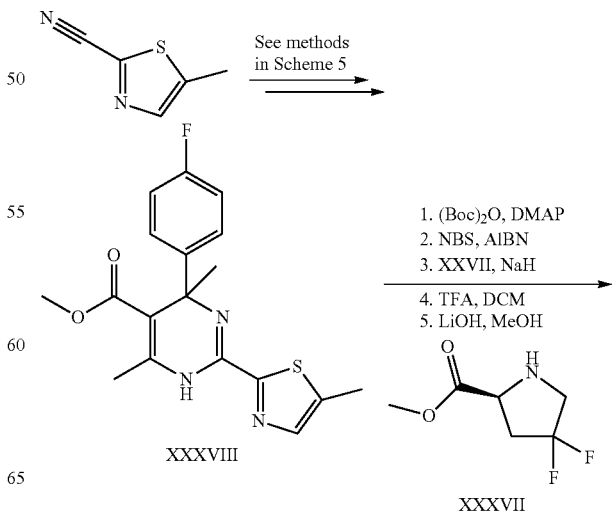

XXXVIII 1. (Boc)₂O, DMAP
2. NBS, AIBN
3. XXVII, NaH
4. TFA, DCM
5. LiOH, MeOH

XXXVII

-continued

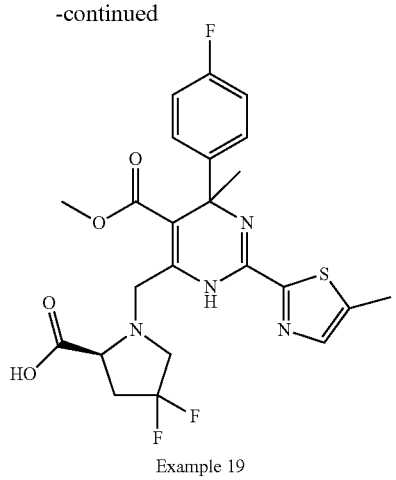
Example 19

Example 20

6-(2-Carboxy-4,4-difluoro-2-methyl-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 3 in Scheme 6 by using 4,4-difluoro-2-methyl-pyrrolidine-2-carboxylic acid methyl ester instead of morpholine-3-carboxylic acid methyl ester.

Example 21

(S)-1-[(S)-5-Cyano-6-(4-fluoro-phenyl)-6-methyl-2-thiazol-2-yl-3,6-dihydro-pyrimidin-4-ylmethyl]-4,4-difluoro-pyrrolidine-2-carboxylic acid The title compound was prepared according to the synthesis method shown in Scheme 2 and Scheme 3. A detailed synthesis route is provided as shown in Scheme 13.

Scheme 13

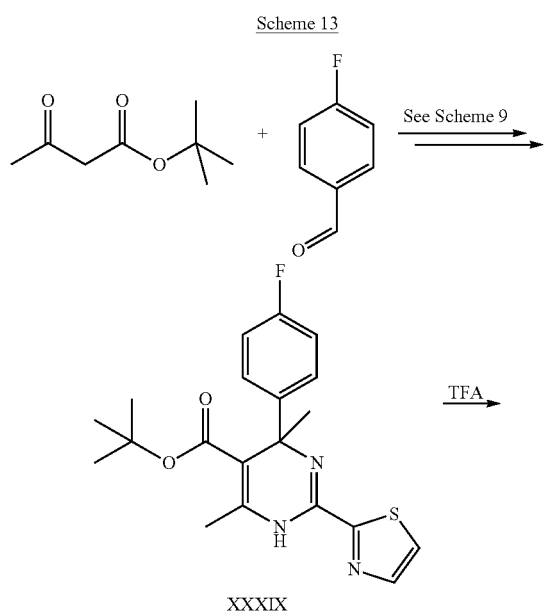

-continued

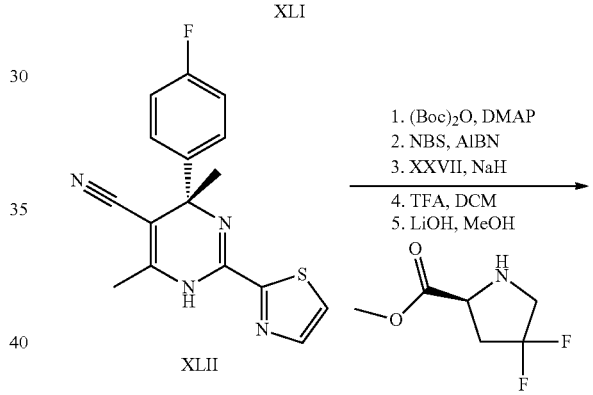

Compound 4-(4-fluoro-phenyl)-4,6-dimethyl-2-thiazol-2-yl-1,4-dihydro-pyrimidine-5-carboxylic acid tert-butyl ester XXXIX was prepared in analogy to XXXIV in Scheme 9 by using 3-oxo-butyric acid tert-butyl ester and 4-fluoro-benzaldehyde instead of 3-oxo-butyric acid methyl ester and 3,4-difluoro-benzaldehyde in the condensation reaction.

To a solution of 4-(4-fluoro-phenyl)-4,6-dimethyl-2-thiazol-2-yl-1,4-dihydro-pyrimidine-5-carboxylic acid tert-butyl ester XXXIX (1.0 g, 2.58 mmol) in DCM (15 mL) was added TFA (2 mL), and the mixture was stirred for 3 hr. After that, the solvent and excess TFA was removed in vacuum. The residue XL was dissolved in DCM (15 mL), to which was added HATU (1.21 g, 3.70 mmol) and NH₃ in dioxane (10 mL, 0.5 M), and the mixture was stirred overnight. The mixture was diluted with DCM (50 mL), and washed with aqueous NaHCO₃ and brine. The organic layer was separated, dried over anhydrous Na₂SO₄ and concentrated to give 0.89 g of 4-(4-fluoro-phenyl)-4,6-dimethyl-2-thiazol-2-yl-1,4-dihydro-pyrimidine-5-carboxylic acid amide as light yellow solid which was directly for next use without purification.

The above crude intermediate (0.89 g) was dissolved in THF (10 mL), TFAA (3 mL) was added and the mixture was stirred for 3 hr. After removal of THF and excess TFAA, the residue was dissolved in MeOH (20 mL). To the solution, K₂CO₃ (2.0 g, 14.5 mmol) was added, and the mixture was stirred at rt for 3 hr. Then the mixture was filtered, the solid was washed with EtOAc (10 mL×2). The combined filtrate was concentrated, the residue was purified by column chromatography (EtOAc/petroleum ether 1/3 to 1/2) to afford XLI as yellow solid (700 mg, totally yield: 87.0%).

The chiral intermediate XLII was separated from XLI by SFC.

The title compound Example 21 was prepared from XLII in analogy to Example 3 in Scheme 6.

Example 22

(S)-4-[5-Cyano-6-(3,4-difluoro-phenyl)-6-methyl-2-thiazol-2-yl-3,6-dihydro-pyrimidin-4-ylmethyl]-morpholine-3-carboxylic acid The title compound was prepared according to the synthesis method shown in Scheme 2 and Scheme 3. A detailed synthesis route is provided as shown in Scheme 14.

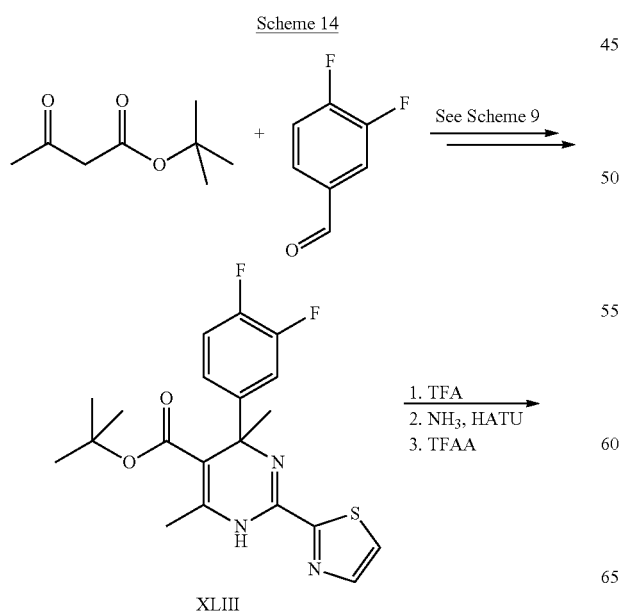

Scheme 14

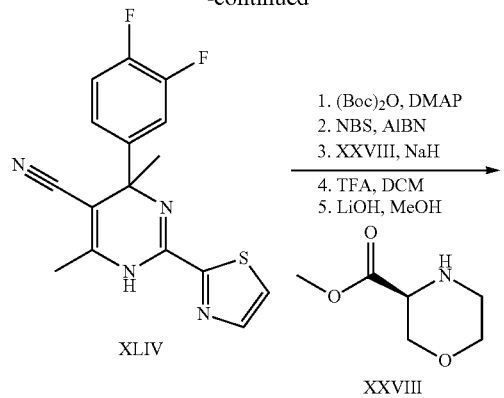

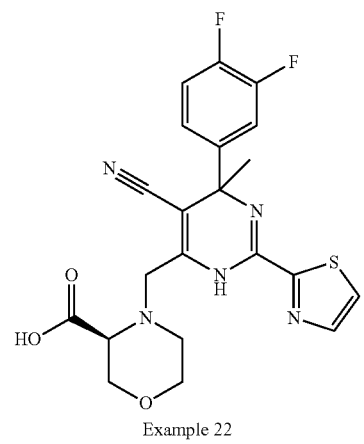

Example 22

Compound 4-(3,4-difluoro-phenyl)-4,6-dimethyl-2-thiazol-2-yl-1,4-dihydro-pyrimidine-5-carboxylic acid tert-butyl ester XLIII was prepared in analogy to XXXIV in Scheme 9 by using 3-oxo-butyric acid tert-butyl ester and 3,4-difluorobenzaldehyde as starting material.

Compound 4-(3,4-difluoro-phenyl)-4,6-dimethyl-2-thiazol-2-yl-1,4-dihydro-pyrimidine-5-carbonitrile XLIV was prepared from tert-butyl ester XLIII in the same method as XLI in Scheme 13.

The title compound Example 22 was prepared in the same method as shown in Scheme 5 and Scheme 6 by using morpholine-(S)-3-carboxylic acid methyl ester XXVIII in the replacement reaction.

Example 23

(S)-[(S)-5-Cyano-6-(3,4-difluoro-phenyl)-6-methyl-2-thiazol-2-yl-3,6-dihydro-pyrimidin-4-ylmethyl]-4,4-difluoro-pyrrolidine-2-carboxylic acid The title compound was prepared according to the synthesis method shown in Scheme 2 and Scheme 3. A detailed synthesis route is provided as shown in Scheme 15.

Scheme 15

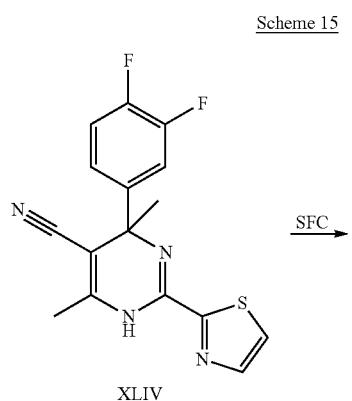

XLIV

SFC →

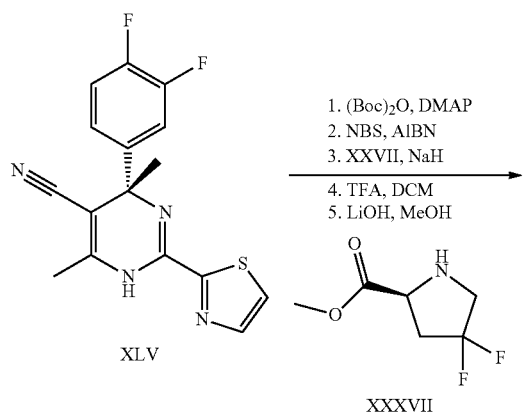

XLV 1. (Boc)₂O, DMAP
2. NBS, AIBN
3. XXVII, NaH
4. TFA, DCM
5. LiOH, MeOH

XXXVII

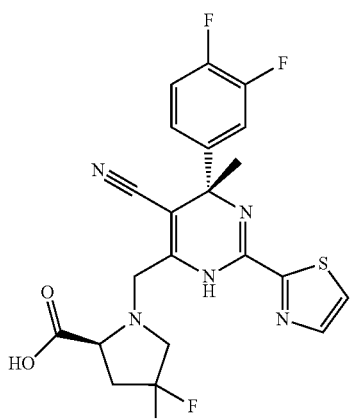

Example 23

Compound XLV was chiral separated from racemate XLIV by SFC and the absolute configuration was assigned through comparing its retention time on SFC with that of the stereochemistry known compound XXVII. The title compound was prepared in the same method as shown in Scheme 5 and Scheme 6 by using XXXVII in the replacement reaction.

Example 24

Preparation of (S)-6-((S)-2-carboxy-4,4-difluoro-pyrrolidin-1-ylmethyl)-4-(3,4-difluoro-phenyl)-4-methyl-2-thiazol-2-yl-1,4-dihydro-pyrimidine-5-carboxylic acid ethyl ester The title compound was prepared in analogy to Example 7 in Scheme 7 by using 4-ethynyl-1,2-difluoro-benzene instead of (S)-morpholine-3-carboxylic acid methyl ester.

Example 25

Preparation of (S)-6-(2-carboxy-5,5-difluoro-piperidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using 5,5-difluoro-piperidine-2-carboxylic acid instead of (S)-morpholine-3-carboxylic acid methyl ester.

Example 26

Preparation of (S)-6-(2-carboxy-4,4-difluoro-piperidin-1-ylmethyl) 4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using 4,4-difluoro-piperidine-2-carboxylic acid instead of (S)-morpholine-3-carboxylic acid methyl ester.

Example 27

Preparation of (S)-6-((S)-2-carboxy-4,4-difluoro-pyrrolidin-1-ylmethyl)-4-(4-fluoro-phenyl)-4-methyl-2-(1-methyl-1H-imidazol-2-yl)-1,4-dihydro-pyrimidine-5-carboxylic acid methyl ester The title compound was prepared in analogy to Example 7 in Scheme 7 by using 1-methyl-1H-imidazole-2-carbonitrile instead of thiazole-2-carbonitrile.

Example 28

Preparation of (R)-6-((S)-2-carboxy-4,4-difluoro-pyrrolidin-1-ylmethyl)-4-(3,4-difluoro-phenyl)-4-methyl-2-thiazol-2-yl-1,4-dihydro-pyrimidine-5-carboxylic acid ethyl ester The title compound was prepared in analogy to Example 7 in Scheme 7 by using 4-ethynyl-1,2-difluoro-benzene instead of 1-ethynyl-4-fluoro-benzene.

Example 29

Preparation of (S)-4-[6-(3,4-difluoro-phenyl)-5-ethoxycarbonyl-6-methyl-2-thiazol-2-yl-3,6-dihydro-pyrimidin-4-ylmethyl]-morpholine-3-carboxylic acid The title compound was prepared in analogy to Example 28 by using (S)-morpholine-3-carboxylic acid instead of (S)-4,4-difluoro-pyrrolidine-2-carboxylic acid.

Example 30

Preparation of (S)-4-[(S)-6-(4-fluoro-phenyl)-5-methoxycarbonyl-6-methyl-2-(1-methyl-1H-imidazol-2-yl)-3,6-dihydro-pyrimidin-4-ylmethyl]-morpholine-3-carboxylic acid The title compound was prepared in analogy to Example 27 by using (S)-morpholine-3-carboxylic acid instead of (S)-4,4-difluoro-pyrrolidine-2-carboxylic acid.

Example 31

Preparation of (R)-6-((S)-2-carboxy-4,4-difluoro-pyrrolidin-1-ylmethyl)-4-(4-fluoro-phenyl)-4-methyl-2-(4-methyl-thiazol-2-yl)-1,4-dihydro-pyrimidine-5-carboxylic acid methyl ester The title compound was prepared in analogy to Example 13 by using 4-methyl-thiazole-2-carbonitrile instead of thiazole-2-carbonitrile.

Example 32

Preparation of (S)-6-((S)-2-carboxy-4,4-difluoro-pyrrolidin-1-ylmethyl)-4-(4-fluoro-phenyl)-4-methyl-2-(4-methyl-thiazol-2-yl)-1,4-dihydro-pyrimidine-5-carboxylic acid methyl ester The title compound was prepared in analogy to Example 13 by using 4-methyl-thiazole-2-carbonitrile instead of thiazole-2-carbonitrile.

Example 33

Preparation of (S)-6-((S)-2-carboxy-4,4-difluoro-pyrrolidin-1-ylmethyl)-2-(5-chloro-thiazol-2-yl)-4-(4-fluoro-phenyl)-4-methyl-1,4-dihydro-pyrimidine-5-carboxylic acid methyl ester The title compound was prepared in analogy to Example 13 by using 5-chloro-thiazole-2-carbonitrile instead of thiazole-2-carbonitrile.

Example 34

Preparation of (S)-6-((2S,4R)-2-Carboxy-4-fluoro-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using (2S,4R)-4-fluoro-pyrrolidine-2-carboxylic acid instead of (S)-morpholine-3-carboxylic acid methyl ester.

Example 35

Preparation of 6-((S)-2-carboxy-4,4-difluoro-pyrrolidin-1-ylmethyl)-4-(4-fluoro-phenyl)-2-isoxazol-3-yl-4-methyl-1,4-dihydro-pyrimidine-5-carboxylic acid methyl ester The title compound was prepared in analogy to Example 11 by using isoxazole-3-carbonitrile instead of thiazole-2-carbonitrile.

Example 36

Preparation of (R)-6-((S)-2-carboxy-4,4-difluoro-2-methyl-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using (S)-4,4-difluoro-2-methyl-pyrrolidine-2-carboxylic acid instead of (S)-morpholine-3-carboxylic acid methyl ester.

Example 37

Preparation of (S)-6-((S)-2-carboxy-4,4-difluoro-pyrrolidin-1-ylmethyl)-4-(4-fluoro-phenyl)-4-methyl-2-(5-methyl-thiazol-2-yl)-1,4-dihydro-pyrimidine-5-carboxylic acid methyl ester The title compound was prepared in analogy to Example 13 by using 5-methyl-thiazole-2-carbonitrile instead of thiazole-2-carbonitrile.

Example 38

Preparation of (S)-6-((S)-2-carboxy-4,4-difluoro-pyrrolidin-1-ylmethyl)-4-(4-fluoro-phenyl)-2-(5-fluoro-thiophen-2-yl)-4-methyl-1,4-dihydro-pyrimidine-5-carboxylic acid methyl ester The title compound was prepared in analogy to Example 13 by using 5-fluoro-thiophene-2-carbonitrile instead of thiazole-2-carbonitrile.

Example 39

Preparation of (S)-6-((2S,4S)-2-carboxy-4-fluoro-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using (2S,4S)-4-fluoro-pyrrolidine-2-carboxylic acid instead of (S)-morpholine-3-carboxylic acid methyl ester. Example 40 Preparation of 6-((S)-2-carboxy-4,4-difluoro-pyrrolidin-1-ylmethyl)-4-(4-fluoro-phenyl)-4-methyl-2-(5-methyl-isoxazol-3-yl)-1,4-dihydro-pyrimidine-5-carboxylic acid methyl ester The title compound was prepared in analogy to Example 11 by using 5-methyl-isoxazole-3-carbonitrile instead of thiazole-2-carbonitrile.

Example 41

Preparation of (S)-6-((S)-2-carboxy-4,4-difluoro-pyrrolidin-1-ylmethyl)-4-(4-fluoro-phenyl)-2-(3-fluoro-thiophen-2-yl)-4-methyl-1,4-dihydro-pyrimidine-5-carboxylic acid methyl ester The title compound was prepared in analogy to Example 13 by using 3-fluoro-thiophene-2-carbonitrile instead of thiazole-2-carbonitrile.

Example 42

Preparation of (R)-6-((S)-2-carboxy-4,4-difluoro-pyrrolidin-1-ylmethyl)-4-(4-fluoro-phenyl)-2-(3-fluoro-thiophen-2-yl)-4-methyl-1,4-dihydro-pyrimidine-5-carboxylic acid methyl ester The title compound was prepared in analogy to Example 13 by using 3-fluoro-thiophene-2-carbonitrile instead of thiazole-2-carbonitrile.

Example 43

Preparation of (S)-6-((S)-2-carboxy-4,4-difluoro-pyrrolidin-1-ylmethyl)-4-(4-fluoro-phenyl)-2-(4-fluoro-thiophen-2-yl)-4-methyl-1,4-dihydro-pyrimidine-5-carboxylic acid methyl ester The title compound was prepared in analogy to Example 13 by using 4-fluoro-thiophene-2-carbonitrile instead of thiazole-2-carbonitrile.

Example 44

Preparation of (S)-6-{[carboxymethyl-(2,2,2-trifluoro-ethyl)-amino]-methyl}-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using (2,2,2-trifluoro-ethylamino)-acetic acid instead of (S)-morpholine-3-carboxylic acid methyl ester.

Example 45

Preparation of (S)-6-((S)-4,4-difluoro-2-methoxycarbonyl-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using (S)-4,4-difluoro-pyrrolidine-2-carboxylic acid methyl ester instead of (S)-morpholine-3-carboxylic acid methyl ester.

Example 46

Preparation of (S)-6-[(S)-2-(2-dimethylamino-ethoxycarbonyl)-4,4-difluoro-pyrrolidin-1-ylmethyl]-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using (S)-4,4-difluoro-pyrrolidine-2-carboxylic acid 2-dimethylamino-ethyl ester instead of (S)-morpholine-3-carboxylic acid methyl ester.

Example 47

Preparation of (S)-6-(2-carbamoyl-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using 4,4-difluoro-pyrrolidine-2-carboxylic acid amide instead of (S)-morpholine-3-carboxylic acid methyl ester.

Example 48

Preparation of (S)-6-((S)-2-carbamoyl-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using (S)-4,4-difluoro-pyrrolidine-2-carboxylic acid amide instead of (S)-morpholine-3-carboxylic acid methyl ester.

Example 49

Preparation of (S)-6-((S)-2-dimethylcarbamoyl-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using (S)-4,4-difluoro-pyrrolidine-2-carboxylic acid dimethylamide instead of (S)-morpholine-3-carboxylic acid methyl ester.

Example 50

Preparation of 6-((S)-4,4-difluoro-2-methylcarbamoyl-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using (S)-4,4-difluoro-pyrrolidine-2-carboxylic acid methylamide instead of (S)-morpholine-3-carboxylic acid methyl ester.

Example 51

Preparation of (S)-6-((S)-4,4-difluoro-2-methanesulfonylaminocarbonyl-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using N—((S)-4,4-difluoro-pyrrolidine-2-carbonyl)-methanesulfonamide instead of (S)-morpholine-3-carboxylic acid methyl ester.

Example 52

Preparation of (S)-6-[(S)-4,4-difluoro-2-(thiazol-2-ylcarbamoyl)-pyrrolidin-1-ylmethyl]-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using (S)-4,4-difluoro-pyrrolidine-2- carboxylic acid thiazol-2-ylamide instead of (S)-morpholine-3-carboxylic acid methyl ester.

Example 53

Preparation of 4-(4-fluoro-phenyl)-6-((R)-3-hydroxymethyl-morpholin-4-ylmethyl)-4-methyl-2-thiazol-2-yl-1,4-dihydro-pyrimidine-5-carboxylic acid methyl ester The title compound was prepared in analogy to Example 7 in Scheme 7 by using (R)-1-morpholin-3-yl-methaol instead of (S)-morpholine-3-carboxylic acid methyl ester.

Example 54

Preparation of (S)-6-[(S)-4,4-difluoro-2-(1-hydroxy-1-methyl-ethyl)-pyrrolidin-1-ylmethyl]-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using 2-((S)-4,4-difluoro-pyrrolidin-2-yl)-propan-2-ol instead of (S)-morpholine-3-carboxylic acid methyl ester.

Example 55

Preparation of (S)-6-((S)-4,4-difluoro-2-hydroxymethyl-pyrrolidin-1-ylmethyl)-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using ((S)-4,4-difluoro-pyrrolidin-2-yl)-methanol instead of (S)-morpholine-3-carboxylic acid methyl ester.

Example 56

Preparation of (S)-6-[4,4-difluoro-2-(3-hydroxy-propyl)-pyrrolidin-1-ylmethyl]-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using 3-(4,4-difluoro-pyrrolidin-2-yl)-propan-1-ol instead of (S)-morpholine-3-carboxylic acid methyl ester.

Example 57

Preparation of (S)-6-[(S)-4,4-difluoro-2-(5-methyl-[1,3,4]oxadiazol-2-yl)-pyrrolidin-1-ylmethyl]-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using 2-((S)-4,4-difluoro-pyrrolidin-2-yl)-5-methyl-[1,3,4]oxadiazole instead of (S)-morpholine-3-carboxylic acid methyl ester.

Example 58

Preparation of (S)-6-[(S)-4,4-difluoro-2-(1H-tetrazol-5-yl)-pyrrolidin-1-ylmethyl]-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using 5-((S)-4,4-difluoro-pyrrolidin-2-yl)-1H-tetrazole instead of (S)-morpholine-3-carboxylic acid methyl ester.

Example 59

Preparation of (S)-6-[(S)-4,4-difluoro-2-(3-methyl-[1,2,4]oxadiazol-5-yl)-pyrrolidin-1-ylmethyl]-4-(4-fluoro-phenyl)-4-methyl-2-thiazol-2-yl-1,4-dihydro-pyrimidine-5-carboxylic acid methyl ester The title compound was prepared in analogy to Example 7 in Scheme 7 by using 5-((S)-4,4-difluoro-pyrrolidin-2-yl)-3-methyl-[1,2,4]oxadiazole instead of (S)-morpholine-3-carboxylicacid methyl ester.

BIOLOGICAL EXAMPLES

Example 60

HBV Inhibition Assays (Biochemical Assay)

Cells and culture conditions: HepDE19 (Haitao Guo et al, Journal of Virology, 81, November 2007, 12472-12484; Richeng Mao et al, Journal of Virology, 85, January 2011, 1048-1057) cells were derived from HepG2 (ATCC, American Type Culture Collection) cells through transfection with pTet-off plasmid (Clontech) that expresses the Tet-responsive transcriptional activator and pTREHBVDE plasmid in which HBV pgRNA expression is controlled by a CMV early promoter with a tetracycline-responsive element. The transfected cells were selected with G418 (also known as Genticin, purchased from Invitrogen). In tetracycline-free medium, cells support high levels of HBV DNA replication and HBV virus secretion. These cells were maintained in Dulbecco's modified Eagle's medium (DMEM)-F12 medium (Invitrogen) supplemented with 10% fetal bovine serum, 100 U/ml penicillin, and 100 µg/ml streptomycin, 0.5 mg/ml of G418 and 1 µg/ml tetracycline.

Anti-HBV activity and cytotoxicity: HepDE19 cells were seeded into 96-well plates ($3\times10^4$ cells/well) with tetracycline-free medium and incubated overnight at 37° C. The test or control compounds were serially half-log diluted with medium and added into the plates (the final concentration of DMSO kept at 0.5% in each well). Five days after compound treatment, cells were washed with PBS and lysed with 50 mM Tris-1 mM EDTA-0.2% CA-630 (pH 8.0) at 37° C. for 20 min. After centrifugation to remove nuclei and other debris, the supernatant was transferred into a new plate and incubated with 2M NaOH/20×SSC (3M NaCl, 0.3M Sodium citrate, pH7.0) at rt for 30 min. Then the samples were transferred to nylon membrane and neutralized with 1M Tris (pH7.4)/2M NaCl. The presence of HBV DNA was detected by dot-blot with DIG-labeled HBV specific DNA probe and quantified by dot density. The compound concentrations that inhibited HBV DNA by 50% ($EC_{50}$) were determined (See Table 1).

To determine if the anti-HBV effect of compound is due to cytotoxicity, HepDE 19 cells (5×10³ cells/well) were seeded into 96-well plates and compounds were treated as described above. Five days after treatment, cell viability was measured by addition of 20 μl of CCK-8 reagent. Four hours after incubation at 37° C., the absorbance at wavelengths of 450 nm and 630 nm ($OD_{450}$ and $OD_{630}$) was recorded by a plate reader. The 50% cytotoxic concentration ($CC_{50}$) of each compounds were determined accordingly.

The compounds of the present invention were tested for their capacity to inhibit a HBV activity and activation as described herein. The Examples were tested in the above assay and found to have $EC_{50}$ of about 0.01 μM to about 50 μM. Particular compounds of formula I were found to have $EC_{50}$ of about 0.41 μM to about 30 μM.

Results of HepDe19 $EC_{50}$ (μM) and $CC_{50}$ (μM) are given in Table 1.

Example A

A compound of formula I can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula I can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

We claim:

1. A method for the treatment of hepatitis B virus infection, which method comprises administering to a patient in need thereof a therapeutically effective amount of a compound of formula (I)

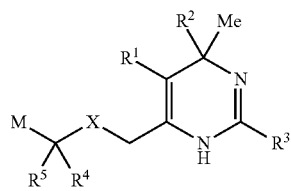

(I)

wherein:

$R^1$ is $C_{1-2}$ alkoxycarbonyl or cyano;

$R^2$ is phenyl, which is substituted by halogen;

$R^3$ is thiazolyl, thienyl, imidazolyl, isoxazolyl or pyridinyl; which is unsubstituted or substituted by halogen or $C_{1-6}$alkyl;

X is oxygen or —$NR^7$;

$R^4$ and $R^5$ are independently selected from hydrogen, $C_{1-6}$alkyl and trifluoro$C_{1-6}$alkyl; or $R^4$ and $R^5$, together with the carbon atom to which they are attached, form a 3 to 7 membered cycloalkyl; or when X is —$NR^7$, one of $R^4$ and $R^5$ is hydrogen or $C_{1-6}$alkyl, and the other of $R^4$ and $R^5$ along with R and the atoms to which $R^4$ or $R^5$ and $R^7$ are attached form a pyrrolidinyl, morpholinyl or piperidinyl ring, which pyrrolidinyl, morpholinyl or piperidinyl ring is unsubstituted or substituted by fluoro;

M is $C_{1-6}$alkoxycarbonyl, carboxy, di-$C_{1-6}$alkylamino$C_{2-6}$alkoxycarbonyl, aminocarbonyl, $C_{1-6}$alkylaminocarbonyl, di-$C_{1-6}$alkylaminocarbonyl, $C_{1-6}$alkylsulfonylaminocarbonyl, 2-thiazolylaminocarbonyl, hydroxy-$C_yH_{2y}$—,

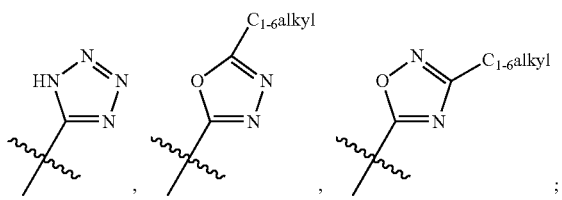

$R^7$ is $C_{1-6}$alkyl or trifluoro$C_{1-6}$alkyl; and y is 1-6;

or a pharmaceutically acceptable salt, or tautomer thereof.

2. The method of claim 1 wherein $R^1$ is $C_{1-2}$alkoxycarbonyl or cyano;

$R^2$ is phenyl, which is once or twice substituted by halogen;

$R^3$ is (i) 2-thiazolyl which is unsubstituted or once substituted by $C_{1-6}$alkyl or halogen, (ii) 2-thienyl, (iii) 2-pyridinyl, which 2-thienyl or 2-pyridinyl are once substituted by halogen, (iv) 2-imidazolyl substituted by one $C_{1-6}$alkyl; or (v) 3-isoxazolyl which is unsubstituted or substituted by one $C_{1-6}$alkyl;

X is oxygen or —$NR^7$;

$R^4$ and $R^5$ are independently selected from hydrogen, $C_{1-6}$alkyl and trifluoro$C_{1-6}$alkyl; or $R^4$ and $R^5$, together with the carbon atom to which they are attached, form a 3 to 7 membered cycloalkyl ring; or when X is —$NR^7$, one of $R^4$ and $R^5$ is hydrogen or $C_{1-6}$alkyl, and the other of $R^4$ and $R^5$ along with R and the atoms to which $R^4$ or $R^5$ and $R^7$ are attached forma morpholinyl, pyrrolidinyl or piperidinyl each substituted by fluoro;

M is $C_{1-6}$alkoxycarbonyl, carboxy, di$C_{1-6}$alkylamino-$C_{2-6}$alkoxycarbonyl, aminocarbonyl, $C_{1-6}$alkylaminocarbonyl, di$C_{1-6}$alkylaminocarbonyl, $C_{1-6}$alkylsulfonylaminocarbonyl, 2-thiazolylaminocarbonyl, hydroxy-$C_yH_{2y}$—,

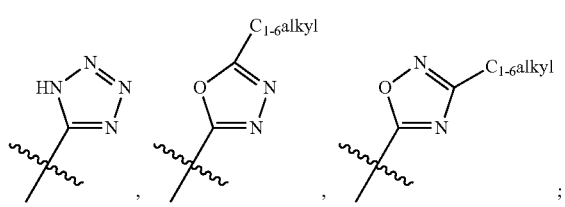

$R^7$ is $C_{1-6}$alkyl or trifluoro$C_{1-6}$alkyl; and
y is 1-6;
or a pharmaceutically acceptable salt, or tautomer thereof.

3. The method of claim 1 wherein
$R^2$ is phenyl substituted by one or two fluorine atoms;
$R^3$ is

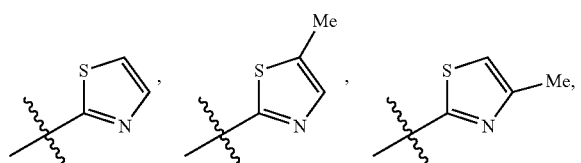

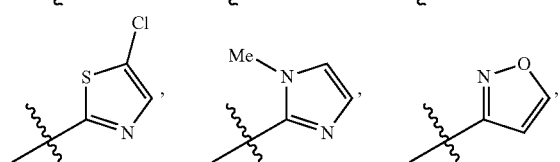

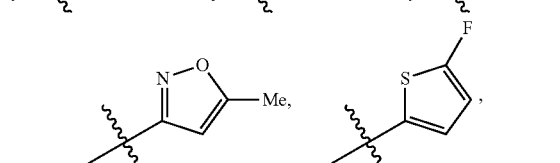

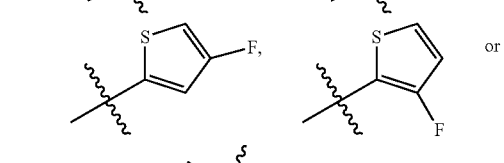

$R^4$ and $R^5$ are independently selected from hydrogen, methyl and trifluoromethyl; or $R^4$ and $R^5$ together with the carbon atom to which they are attached are cyclopropyl; or when X is —NR$^7$, one of $R^4$ and $R^5$ is hydrogen or methyl, and the other of $R^4$ and $R^5$ along with $R^7$ and the atoms to which $R^4$ or $R^5$ and $R^7$ are attached form:

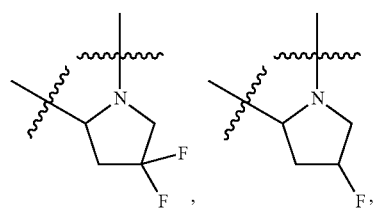

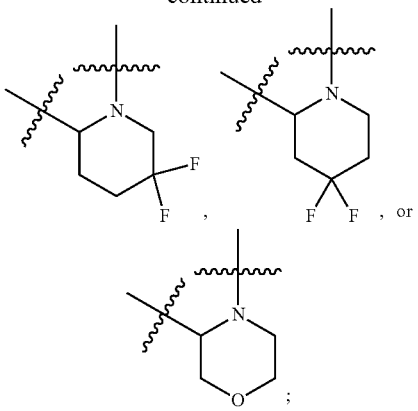

M is methoxycarbondependentl, carboxy, dimethylaminoethoxycarbonyl, aminocarbonyl; or dimethylaminocarbongeth, methylaminocarbonyl, methylsulfonylaminocarbonyl, 2-thiazolylaminocarbonyl, hydroxymethyl, hydroxypropyl, —C(Me)$_2$OH,

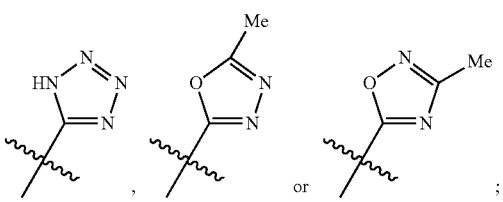 [SMILES: *c1nnn[nH]1 ; *c1nnc(C)o1 ; *c1nc(C)no1]

and
$R^7$ is methyl or trifluoroethyl;
or a pharmaceutically acceptable salt, or tautomer thereof.

4. The method of claim 1 wherein
$R^1$ is $C_{1-2}$alkoxycarbonyl;
$R^2$ is phenyl substituted by one halogen;
$R^3$ is thiazol-2-yl;
X is oxygen;
$R^4$ and $R^5$ are independently selected from hydrogen, $C_{1-6}$alkyl and trifluoro$C_{1-6}$alkyl; and
M is $C_{1-6}$alkoxycarbonyl or carboxy.

5. The method of claim 1 wherein
$R^1$ is methoxycarbonyl;
$R^2$ is 4-fluorophenyl;
$R^3$ is thiazol-2-yl;
X is oxygen;
$R^4$ and $R^5$ are independently selected from hydrogen, methyl and trifluoromethyl; and
M is methoxycarbonyl or carboxy.

6. The method of claim 1 wherein
$R^1$ is $C_{1-2}$alkoxycarbonyl;
$R^2$ is phenyl substituted by one halogen;
$R^3$ is 2-thiazolyl;
X is —N($C_{1-6}$alkyl) or —N(trifluoro$C_{1-6}$alkyl);
$R^4$ is hydrogen;
$R^5$ is hydrogen;
or $R^4$ and $R^5$, together with the carbon atom to which they are attached, form a 3 to 7 membered cycloalkyl; and
M is carboxy.

7. The method of claim 1 wherein
$R^1$ is methoxycarbonyl;
$R^2$ is 4-fluorophenyl;
$R^3$ is thiazol-2-yl;

X is —NCH$_3$ or —NCH$_2$CF$_3$;
R$^4$ is hydrogen;
R$^5$ is hydrogen;
or R$^4$ and R$^5$, together with the carbon atom to which they are attached, form cyclopropyl; and
M is carboxy.

8. The method of claim 1 wherein
R$^1$ is C$_{1-2}$alkoxycarbonyl or cyano;
R$^2$ is phenyl substituted by one or two halogen;
R$^3$ is thiazol-2-yl; 2-pyridin-2-yl substituted by one halogen; or imidazol-2-yl substituted by one C$_{1-6}$alkyl;
X is —NR$^7$;
one of R$^4$ and R$^5$ is hydrogen, and the other of R$^4$ and R$^5$ along with R$^7$ and the atoms to which R$^4$ or R$^5$ and R$^7$ are attached form a morpholinyl;
M is C$_{1-6}$alkoxycarbonyl, carboxy or hydroxy-C$_y$H$_{2y}$—; and
y is 1-6.

9. The method of claim 1 wherein
R$^1$ is methoxycarbonyl, ethoxycarbonyl or cyano;
R$^2$ is 4-fluorophenyl or 3,4-difluorophenyl;
R$^3$ is thiazol-2-yl, 5-fluoro-pyridin-2-yl or 1-methyl-imidazol-2-yl;
one of R$^4$ and R$^5$ is hydrogen, and the other of R$^4$ and R$^5$ along with R$^7$ and the atoms to which R$^4$ or R$^5$ and R$^7$ are attached form:

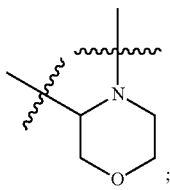 [SMILES: *C1COCCN1*]

and
M is methoxycarbonyl, carboxy or hydroxymethyl-.

10. The method of claim 1 wherein
R$^1$ is C$_{1-2}$alkoxycarbonyl or cyano;
R$^2$ is phenyl substituted by one or two halogen;
R$^3$ is thiazol-2-yl optionally substituted by one C$_{1-6}$alkyl or one halogen; thien-2-yl or -pyridin-2-yl said thien-2-yl or -pyridin-2-yl substituted by one halogen; -imidazol-2-yl, which is substituted by one C$_{1-6}$alkyl; or isoxazol-3-yl optionally substituted by one C$_{1-6}$alkyl;
X is —NR$^7$;
one of R$^4$ and R$^5$ is hydrogen or C$_{1-6}$alkyl, and the other of R$^4$ and R$^5$ along with R$^7$ and the atoms to which R$^4$ or R$^5$ and R$^7$ are attached form a pyrrolidinyl or piperidinyl substituted by fluoro;
M is C$_{1-6}$alkoxycarbonyl, carboxy, di-C$_{1-6}$alkylaminoC$_{2-6}$ alkoxycarbonyl, aminocarbonyl, C$_{1-6}$alkylaminocarbonyl, di-C$_{1-6}$alkylaminocarbonyl, C$_{1-6}$alkylsulfonylaminocarbonyl, 2-thiazolylaminocarbonyl, hydroxy-C$_y$H$_{2y}$—,

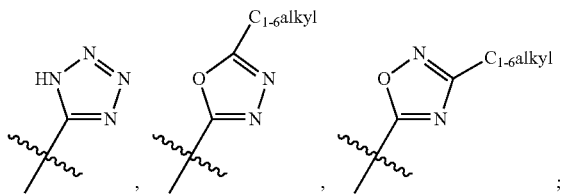

and
y is 1-6.

11. The method of claim 1 wherein
R$^1$ is methoxycarbonyl, ethoxycarbonyl or cyano;
R$^2$ is 4-fluorophenyl or 3,4-difluorophenyl;
R$^3$

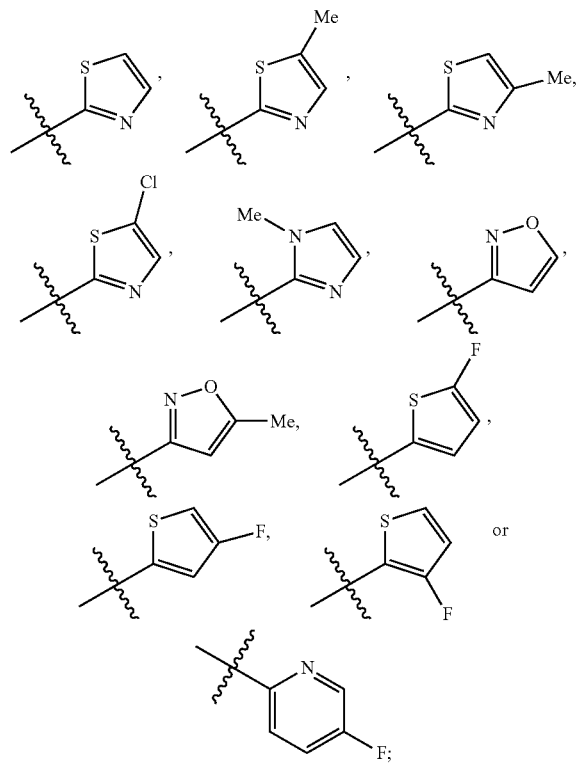

X is —NR$^7$;
one of R$^4$ and R$^5$ is hydrogen or methyl, and the other of R$^4$ and R$^5$ along with R$^7$ and the atoms to which R$^4$ or R$^5$ and R$^7$ are attached form:

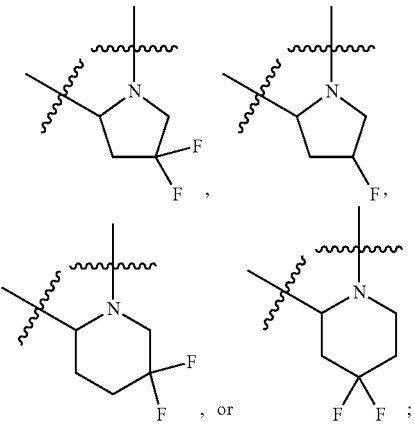

and
M is methoxycarbonyl, carboxy, dimethylaminoethoxycarbonyl, aminocarbonyl, dimethylaminocarbonyl, methylaminocarbonyl, methylsulfonylaminocarbonyl, 2-thiazolylaminocarbonyl, hydroxymethyl, hydroxypropyl, —C(Me)$_2$OH,

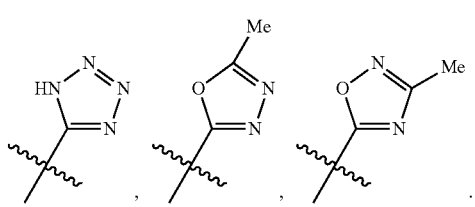 [SMILES: *c1nnn[nH]1 ; *c1nnc(C)o1 ; *c1nc(C)no1]

12. The method of claim 1 where in the compound of formula (I) is a compound of formula (I')

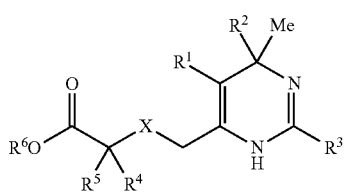

wherein $R^1$ is $C_{1-2}$alkoxycarbonyl or cyano;

$R^2$ is phenyl, which is substituted by halogen;

$R^3$ is 2-thiazolyl which is unsubstituted or substituted by $C_{1-6}$alkyl or 2-pyridinyl, which is substituted by halogen;

X is oxygen or —$NR^7$;

$R^4$ and $R^5$ are independently selected from hydrogen, $C_{1-6}$alkyl and trifluoro$C_{1-6}$alkyl; or $R^4$ and $R^5$, together with the carbon atom to which they are attached, form a 3 to 7 membered cycloalkyl; or when X is —$NR^7$, one of $R^4$ and $R^5$ is hydrogen or $C_{1-6}$alkyl, and the other of $R^4$ and $R^5$ along with R and the atoms to which $R^4$ or $R^5$ and $R^7$ are attached form a morpholinyl; or pyrrolidinyl substituted by fluoro;

$R^6$ is hydrogen or $C_{1-6}$alkyl; and $R^7$ is $C_{1-6}$alkyl;

or a pharmaceutically acceptable salt, or tautomer thereof.

13. The method of claim 12 wherein $R^1$ is methoxycarbonyl or cyano;

$R^2$ is phenyl substituted once or twice by fluoro;

$R^3$ is thiazol-2-yl, 5-methyl-thiazol-2-yl or 5-fluoro-pyridin-2-yl; or;

X is oxygen or —$NR^7$;

$R^4$ and $R^5$ are independently selected from hydrogen, methyl and trifluoromethyl; or $R^4$ and $R^5$ together with the carbon atom to which they are attached form cyclopropyl; or when X is —$NR^7$, one of $R^4$ and $R^5$ is hydrogen or methyl, and the other of $R^4$ and $R^5$ along with $R^7$ and the atoms to which $R^4$ or $R^5$ and $R^7$ are attached form:

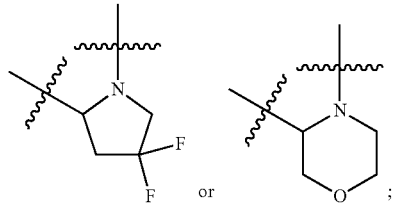 [SMILES: *C1CC(F)(F)CN1* ; *C1COCCN1*]

$R^6$ is hydrogen or methyl; and $R^7$ is methyl;

or a pharmaceutically acceptable salt, or tautomer thereof.

14. The method of claim 12 wherein $R^1$ is $C_{1-2}$alkoxycarbonyl or cyano;

$R^2$ is phenyl which is substituted by halogen;

$R^3$ is thiazol-2-yl or pyridin-2-yl, which is substituted by halogen;

X is —$NR^7$;

one of $R^4$ and $R^5$ is hydrogen or $C_{1-6}$alkyl, and the other of $R^4$ and $R^5$ along with $R^7$ and the atoms to which $R^4$ or $R^5$ and $R^7$ are attached form a morpholinyl; and $R^6$ is hydrogen or $C_{1-6}$alkyl.

15. The method of claim 12 wherein $R^1$ is methoxycarbonyl or cyano;

$R^2$ is 4-fluorophenyl or 3,4-difluorophenyl;

$R^3$ is thiazol-2-yl or 5-fluoro-pyridin-2-yl;

one of $R^4$ and $R^5$ is hydrogen or methyl, and the other of $R^4$ and $R^5$ along with $R^7$ and the atoms to which $R^4$ or $R^5$ and $R^7$ are attached form

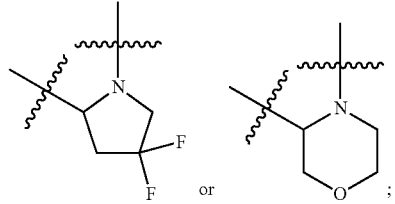 [SMILES: *C1CC(F)(F)CN1* ; *C1COCCN1*]

and $R^6$ is hydrogen or methyl.

16. The method of claim 12 wherein $R^1$ is $C_{1-2}$alkoxycarbonyl or cyano;

$R^2$ is phenyl which is substituted by halogen;

$R^3$ is 2-thiazolyl optionally substituted by $C_{1-6}$alkyl or 2-pyridinyl said pyridinyl substituted by halogen;

X is —$NR^7$;

one of $R^4$ and $R^5$ is hydrogen or $C_{1-6}$alkyl, and the other and the other of $R^4$ and $R^5$ along with $R^7$ and the atoms to which $R^4$ or $R^5$ and $R^7$ are attached form a pyrrolidinyl substituted by fluoro; and $R^6$ is hydrogen or $C_{1-6}$alkyl.

17. The method of claim 12 wherein
R¹ is methoxycarbonyl or cyano;
R² is 4-fluorophenyl or 3,4-difluorophenyl;
R³ is thiazol-2-yl, 5-methyl-thiazol-2-yl or 5-fluoro-pyridin-2-yl;
X is —NR⁷;
one of R⁴ and R⁵ is hydrogen or methyl, and the other of R⁴ and R⁵ along with R⁷ and the atoms to which R⁴ or R⁵ and R⁷ are attached form and
R⁶ is hydrogen or methyl.

18. The method of claim 1 wherein the compound of formula (I) is selected from:
4-(4-fluoro-phenyl)-6-(1-methoxycarbonyl-1-methyl-ethoxymethyl)-4-methyl-2-thiazol-2-yl-1,4-dihydro-pyrimidine-5-carboxylic acid methyl ester; 6-(1-carboxy-2,2,2-trifluoro-ethoxymethyl)-4-(4-fluoro-phenyl)-4-methyl-2-thiazol-2-yl-1,4-dihydro-pyrimidine-5-carboxylic acid methyl ester; 6-{[(1-carboxy-cyclopropyl)-methyl-amino]-methyl}-4-(4-fluoro-phenyl)-4-methyl-2-thiazol-2-yl-1,4-dihydro-pyrimidine-5-carboxylic acid methyl ester; 4-[6-(4-fluoro-phenyl)-5-methoxycarbonyl-6-methyl-2-thiazol-2-yl-3,6-dihydro-pyrimidin-4-ylmethyl]-morpholine-3-carboxylic acid; 4-[6-(4-fluoro-phenyl)-5-methoxycarbonyl-6-methyl-2-thiazol-2-yl-3,6-dihydro-pyrimidin-4-ylmethyl]-morpholine-(S)-3-carboxylic acid methyl ester; 4-[6-(4-fluoro-phenyl)-5-methoxycarbonyl-6-methyl-2-thiazol-2-yl-3,6-dihydro-pyrimidin-4-ylmethyl]-morpholine-(S)-3-carboxylic acid; (S)-4-[6-(4-fluoro-phenyl)-5-methoxycarbonyl-6-methyl-2-thiazol-2-yl-3,6-dihydro-pyrimidin-4-ylmethyl]-morpholine-(S)-3-carboxylic acid; (S)-4-[6-(4-fluoro-phenyl)-5-methoxycarbonyl-6-methyl-2-thiazol-2-yl-3,6-dihydro-pyrimidin-4-ylmethyl]-morpholine-(R)-3-carboxylic acid; 4-[6-(4-fluoro-phenyl)-2-(5-fluoro-pyridin-2-yl)-5-methoxycarbonyl-6-methyl-3,6-dihydro-pyrimidin-4-ylmethyl]-morpholine-(R)-3-carboxylic acid; 4-[6-(4-fluoro-phenyl)-2-(5-fluoro-pyridin-2-yl)-5-methoxycarbonyl-6-methyl-3,6-dihydro-pyrimidin-4-ylmethyl]-morpholine-(S)-3-carboxylic acid; 6-(2-(S)-carboxy-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester; 6-(2-(R)-carboxy-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester; (S)-6-((S)-2-carboxy-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester; (S)-6-((S)-2-carboxy-4,4-difluoro-pyrrolidin-1-ylmethyl)-4-(3,4-difluoro-phenyl)-4-methyl-2-thiazol-2-yl-1,4-dihydro-pyrimidine-5-carboxylic acid methyl ester; 4-[(S)-6-(3,4-difluoro-phenyl)-5-methoxycarbonyl-6-methyl-2-thiazol-2-yl-3,6-dihydro-pyrimidin-4-ylmethyl]-morpholine-3-carboxylic acid methyl ester; 4-[6-(3,4-difluoro-phenyl)-5-methoxycarbonyl-6-methyl-2-thiazol-2-yl-3,6-dihydro-pyrimidin-4-ylmethyl]-morpholine-3-carboxylic acid; 6-(4,4-difluoro-2-methoxycarbonyl-pyrrolidin-1-ylmethyl)-4-(4-fluoro-phenyl)-2-(5-fluoro-pyridin-2-yl)-4-methyl-1,4-dihydro-pyrimidine-5-carboxylic acid methyl ester; 6-(2-carboxy-4,4-difluoro-pyrrolidin-1-ylmethyl)-4-(4-fluoro-phenyl)-2-(5-fluoro-pyridin-2-yl)-4-methyl-1,4-dihydro-pyrimidine-5-carboxylic acid methyl ester; 6-((S)-2-carboxy-4,4-difluoro-pyrrolidin-1-ylmethyl)-4-(4-fluoro-phenyl)-4-methyl-2-(5-methyl-thiazol-2-yl)-1,4-dihydro-pyrimidine-5-carboxylic acid methyl ester; 6-(2-carboxy-4,4-difluoro-2-methyl-pyrrolidin-1-ylmethyl)-4-(4-fluoro-phenyl)-4-methyl-2-thiazol-2-yl-1,4-dihydro-pyrimidine-5-carboxylic acid methyl ester; (S)-1-[(S)-5-cyano-6-(4-fluoro-phenyl)-6-methyl-2-thiazol-2-yl-3,6-dihydro-pyrimidin-4-ylmethyl]-4,4-difluoro-pyrrolidine-2-carboxylic acid; (S)-4-[5-cyano-6-(3,4-difluoro-phenyl)-6-methyl-2-thiazol-2-yl-3,6-dihydro-pyrimidin-4-ylmethyl]-morpholine-3-carboxylic acid; (S)-1-[(S)-5-cyano-6-(3,4-difluoro-phenyl)-6-methyl-2-thiazol-2-yl-3,6-dihydro-pyrimidin-4-ylmethyl]-4,4-difluoro-pyrrolidine-2-carboxylic acid; (S)-6-((S)-2-carboxy-4,4-difluoro-pyrrolidin-1-ylmethyl)-4-(3,4-difluoro-phenyl)-4-methyl-2-thiazol-2-yl-1,4-dihydro-pyrimidine-5-carboxylic acid ethyl ester; (S)-6-(2-carboxy-5,5-difluoro-piperidin-1-ylmethyl)-4-(4-fluoro-phenyl)-4-methyl-2-thiazol-2-yl-1,4-dihydro-pyrimidine-5-carboxylic acid methyl ester; (S)-6-(2-carboxy-4,4-difluoro-piperidin-1-ylmethyl)4-(4-fluoro-phenyl methyl-2-thiazol-2-yl-1,4-dihydro-pyrimidine-5-carboxylic acid methyl ester; (S)-6-((S)-2-carboxy-4,4-difluoro-pyrrolidin-1-ylmethyl)-4-(4-fluoro-phenyl)-4-methyl-2-(1-methyl-1H-imidazol-2-yl)-1,4-dihydro-pyrimidine-5-carboxylic acid methyl ester; (R)-6-((S)-2-carboxy-4,4-difluoro-pyrrolidin-1-ylmethyl)-4-(3,4-difluoro-phenyl)-4-methyl-2-thiazol-2-yl-1,4-dihydro-pyrimidine-5-carboxylic acid ethyl ester; (S)-4-[6-(3,4-difluoro-phenyl)-5-ethoxycarbonyl-6-methyl-2-thiazol-2-yl-3,6-dihydro-pyrimidin-4-ylmethyl]-morpholine-3-carboxylic acid; (S)-4-[(S)-6-(4-fluoro-phenyl)-5-methoxycarbonyl-6-methyl-2-(1-methyl-1H-imidazol-2-yl)-3,6-dihydro-pyrimidin-4-ylmethyl]-morpholine-3-carboxylic acid; (R)-6-((S)-2-carboxy-4,4-difluoro-pyrrolidin-1-ylmethyl)-4-(4-fluoro-phenyl)-4-methyl-2-(4-methyl-thiazol-2-yl)-1,4-dihydro-pyrimidine-5-carboxylic acid methyl ester; (S)-6-((S)-2-carboxy-4,4-difluoro-pyrrolidin-1-ylmethyl)-4-(4-fluoro-phenyl)-4-methyl-2-(4-methyl-thiazol-2-yl)-1,4-dihydro-pyrimidine-5-carboxylic acid methyl ester; (S)-6-((S)-2-carboxy-4,4-difluoro-pyrrolidin-1-ylmethyl)-2-(5-chloro-thiazol-2-yl)-4-(4-fluoro-phenyl)-4-methyl-1,4-dihydro-pyrimidine-5-carboxylic acid methyl ester; (S)-6-((2S,4R)-2-carboxy-4-fluoro-pyrrolidin-1-ylmethyl)-4-(4-fluoro-phenyl)-4-methyl-2-thiazol-2-yl-1,4-dihydro-pyrimidine-5-carboxylic acid methyl ester; 6-((S)-2-carboxy-4,4-difluoro-pyrrolidin-1-ylmethyl)-4-(4-fluoro-phenyl)-2-isoxazol-3-yl-4-methyl-1,4-dihydro-pyrimidine-5-carboxylic acid methyl ester; (R)-6-((S)-2-carboxy-4,4-difluoro-2-methyl-pyrrolidin-1-ylmethyl)-4-(4-fluoro-phenyl)-4-methyl-2-thiazol-2-yl-1,4-dihydro-pyrimidine-5-carboxylic acid methyl ester; (S)-6-((S)-2-carboxy-4,4-difluoro-pyrrolidin-1-ylmethyl)-4-(4-fluoro-phenyl)-4-methyl-2-(5-methyl-thiazol-2-yl)-1,4-dihydro-pyrimidine-5-carboxylic acid methyl ester; (S)-6-((S)-2-carboxy-4,4-difluoro-pyrrolidin-1-ylmethyl)-4-(4-fluoro-phenyl)-2-(5-fluoro-thiophen-2-yl)-4-methyl-1,4-dihydro-pyrimidine-5-carboxylic acid methyl ester; (S)-6-((2S,4S)-2-carboxy-4-fluoro-pyrrolidin-1-ylmethyl)-4-(4-fluoro-phenyl)-4-methyl-2-thiazol-2-yl-1,4-dihydro-pyrimidine-5-carboxylic acid methyl ester; 6-((S)-2-carboxy-4,4-difluoro-pyrrolidin-1-ylmethyl)-4-(4-fluoro-phenyl)-4-methyl-2-(5-methyl-isoxazol-3-yl)-1,4-dihydro-pyrimidine-5-carboxylic acid methyl ester; (S)-6-((S)-2-carboxy-4,4-difluoro-pyrrolidin-1-ylmethyl)-4-(4-fluoro-phenyl)-2-(3-fluoro-thiophen-2-yl)-4-methyl-1,4-dihydro-pyrimidine-5-carboxylic acid methyl ester; (R)-6-((S)-2-carboxy-4,4-difluoro-pyrrolidin-1-ylmethyl)-4-(4-fluoro-phenyl)-2-(3-fluoro-thiophen-2-yl)-4-methyl-1,4-dihydro-pyrimidine-5-carboxylic acid methyl ester; (S)-6-((S)-2-carboxy-4,4-difluoro-pyrrolidin-1-ylmethyl)-4-(4-fluoro-phenyl)-2-(4-fluoro-thiophen-2-yl)-4-methyl-1,4-dihydro-pyrimidine-5-carboxylic acid methyl ester; (S)-6-{[carboxymethyl-(2,2,2-trifluoro-ethyl)-amino]-methyl}-4-(4-fluoro-phenyl)-4-methyl-2-thiazol-2-yl-1,4-dihydro-pyrimidine-5-carboxylic acid methyl ester; (S)-6-((S)-4,4-difluoro-2-methoxycarbonyl-pyrrolidin-1-ylmethyl)-4-(4-fluoro-phenyl)-4-methyl-2-thiazol-2-yl-1,4-dihydro-pyrimidine-5-carboxylic acid methyl ester; (S)-6-[(S)-2-(2-dimethylamino-ethoxycarbonyl)-4,4-difluoro-pyrrolidin-1-ylmethyl]-4-(4-fluoro-phenyl)-4-methyl-2-thiazol-2-yl-1,4-dihydro-pyrimidine-5-carboxylic acid methyl ester; (S)-6-(2-carbamoyl-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester; (S)-6-((S)-2-carbamoyl-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester; (S)-6-((S)-2-dimethylcarbamoyl-4,4-difluoro-pyrrolidin-1-ylmethyl)-4-(4-fluoro-phenyl)-4-methyl-2-thiazol-2-yl-1,4-dihydro-pyrimidine-5-carboxylic acid methyl ester; 6-((S)-4,4-difluoro-2-methylcarbamoyl-pyrrolidin-1-ylmethyl)-4-(4-fluoro-phenyl)-4-methyl-2-thiazol-2-yl-1,4-dihydro-pyrimidine-5-carboxylic acid methyl ester; (S)-6-((S)-4,4-difluoro-2-methane sulfonylaminocarbonyl-pyrrolidin-1-ylmethyl)-4-(4-fluoro-phenyl)-4-methyl-2-thiazol-2-yl-1,4-dihydro-pyrimidine-5-carboxylic acid methyl ester; (S)-6-[(S)-4,4-difluoro-2-(thiazol-2-ylcarbamoyl)-pyrrolidin-1-ylmethyl]-4-(4-fluoro-phenyl)-4-methyl-2-thiazol-2-yl-1,4-dihydro-pyrimidine-5-carboxylic acid methyl ester; 4-(4-fluoro-phenyl)-6-((R)-3-hydroxymethyl-morpholin-4-ylmethyl)-4-methyl-2-thiazol-2-yl-1,4-dihydro-pyrimidine-5-carboxylic acid methyl ester; (S)-6-[(S)-4,4-difluoro-2-(1-hydroxy-1-methyl-ethyl)-pyrrolidin-1-ylmethyl]-4-(4-fluoro-phenyl)-4-methyl-2-thiazol-2-yl-1,4-dihydro-pyrimidine-5-carboxylic acid methyl ester; (S)-6-((S)-4,4-difluoro-2-hydroxymethyl-pyrrolidin-1-ylmethyl)-4-(4-fluoro-phenyl)-4-methyl-2-thiazol-2-yl-1,4-dihydro-pyrimidine-5-carboxylic acid methyl ester; (S)-6-[4,4-difluoro-2-(3-hydroxy-propyl)-pyrrolidin-1-ylmethyl]-4-(4-fluoro-phenyl)-4-methylethy-2-thiazol-2-yl-1,4-dihydro-pyrimidine-5-carboxylic acid methyl ester; (S)-6-[(S)-4,4-difluoro-2-(5-methyl-[1,3,4]oxadiazol-2-yl)-pyrrolidin-1-ylmethyl]-4-(4-fluoro-phenyl)-4-methyl-2-thiazol-2-yl-1,4-dihydro-pyrimidine-5-carboxylic acid methyl ester; (S)-6-[(S)-4,4-difluoro-2-(1H-tetrazol-5-yl)-pyrrolidin-1-ylmethyl]-4-(4-fluoro-phenyl)-4-methyl-2-thiazol-2-yl-1,4-dihydro-pyrimidine-5-carboxylic acid methyl ester; and (S)-6-[(S)-4,4-difluoro-2-(3-methyl-[1,2,4]oxadiazol-5-yl)-pyrrolidin-1-ylmethyl]-4-(4-fluoro-phenyl)-4-methyl-2-thiazol-2-yl-1,4-dihydro-pyrimidine-5-carboxylic acid methyl ester, or a pharmaceutically acceptable salt, or tautomer thereof.

* * * * *